US007553632B2

(12) United States Patent  
Niles et al.

(10) Patent No.: US 7,553,632 B2
(45) Date of Patent: Jun. 30, 2009

(54) LUMINOGENIC AND NONLUMINOGENIC MULTIPLEX ASSAY

(75) Inventors: Andrew Niles, Madison, WI (US); Terry L. Riss, Oregon, WI (US)

(73) Assignee: Promega Corporation, Madison, WI (US)

( * ) Notice: Subject to any disclaimer, the term of this patent is extended or adjusted under 35 U.S.C. 154(b) by 69 days.

(21) Appl. No.: 11/489,978

(22) Filed: Jul. 20, 2006

(65) Prior Publication Data

US 2007/0178545 A1 Aug. 2, 2007

Related U.S. Application Data

(63) Continuation of application No. PCT/US2005/002158, filed on Jan. 24, 2005, which is a continuation-in-part of application No. 10/762,836, filed on Jan. 22, 2004.

(51) Int. Cl.
*C12Q 1/37* (2006.01)
*C12Q 1/02* (2006.01)
*G01N 33/53* (2006.01)

(52) U.S. Cl. ............................ 435/23; 435/29; 435/7.72
(58) Field of Classification Search ........................ None
See application file for complete search history.

(56) References Cited

U.S. PATENT DOCUMENTS

| | | | |
|---|---|---|---|
| 5,035,999 | A | 7/1991 | Geiger et al. |
| 5,098,828 | A | 3/1992 | Geiger et al. |
| 5,314,805 | A | 5/1994 | Haugland et al. |
| 5,698,411 | A | 12/1997 | Lucas et al. |
| 5,744,320 | A | 4/1998 | Sherf et al. |
| 5,976,822 | A | 11/1999 | Landrum et al. |
| 6,335,429 | B1 | 1/2002 | Cai et al. |
| 6,586,196 | B1 | 7/2003 | Bronstein et al. |
| 6,602,657 | B1 | 8/2003 | Bronstein et al. |
| 6,613,541 | B1 | 9/2003 | Vaddi et al. |
| 6,759,207 | B2 | 7/2004 | Weber et al. |
| 6,811,990 | B1 | 11/2004 | Corey et al. |
| 6,890,745 | B1 | 5/2005 | Leng |
| 7,416,854 | B2 | 8/2008 | Riss et al. |
| 2002/0068316 | A1 | 6/2002 | Rust et al. |
| 2002/0119500 | A1 | 8/2002 | Xue et al. |
| 2003/0211560 | A1 | 11/2003 | O'Brien et al. |
| 2004/0171099 | A1 | 9/2004 | Cali et al. |
| 2005/0164321 | A1 | 7/2005 | Riss et al. |
| 2008/0268482 | A1 | 10/2008 | Riss et al. |
| 2009/0017482 | A1 | 1/2009 | Riss et al. |

FOREIGN PATENT DOCUMENTS

| | | |
|---|---|---|
| EP | 1382691 A2 | 1/2004 |
| WO | WO-0036098 A1 | 6/2000 |
| WO | WO-0050630 A2 | 8/2000 |
| WO | WO-01/46694 A2 | 6/2001 |
| WO | WO-0157242 A2 | 8/2001 |
| WO | WO-0200882 A2 | 1/2002 |
| WO | WO-0212547 A1 | 2/2002 |
| WO | WO-03025192 A2 | 3/2003 |
| WO | WO-03066611 A1 | 8/2003 |
| WO | WO-2005073722 A2 | 8/2005 |
| WO | WO-2005073722 A3 | 8/2005 |
| WO | WO-2007027653 A1 | 3/2007 |

OTHER PUBLICATIONS

O'Connell et al. Live/Dead Assay for Cell Viability; AfCS Procedure Protocol PP00000023 (2002) http://wwwsignaling-gateway.org/data/cgi-bin/ProtocolFile.cgi/afcs_PP00000023.pdf?pid=PP00000023 downloaded Nov. 19, 2007.*
Rosser et al. Calpain Activity Increases in Hepatocytes Following Addition of ATP; The Journal of Biological Chemistry, vol. 268, No. 31 (1993) pp. 23593-23600.*
"Partial International Search Report for corresponding PCT Application No. PCT/US2005/002158", (Oct. 12, 2006), 2 pgs.
Grant, S. K., et al., "Development of Novel Assays for Proteolytic Enzymes Using Rhodamine-Based Fluorogenic Substrates", *Journal of Biomolecular Screening*, 7(6), (2002), 531-540.
"Apoptosis Inducers And The Assay of Caspase Activity Biomol", *Fased Journal*, 2(8), Abstract No. T10, Federation of American Studies for Experimental Biology,(Apr. 24, 1998),p. A1488.
"U.S. Appl. No. 10/762,836, Response filed Nov. 2, 2006 Non-Final Office Action mailed Sep. 8, 2006", 15 pgs.
"U.S. Appl. No. 10/762,836 RCE/Preliminary Amendment Filed on Aug. 31, 2007", 10.
"U.S. Appl. No. 10/762,836, Final Office Action mailed Feb. 2, 2007", 8 pgs.
"U.S. Appl. No. 10/762,836, Non-Final Office Action mailed Mar. 21, 2006", 16 pgs.
"U.S. Appl. No. 10/762,836, Non-Final Office Action mailed Sep. 8, 2006", 8 pgs.
"U.S. Appl. No. 10/762,836, Notice of allowance mailed May 31, 2007", 6 pgs.
"U.S. Appl. No. 10/762,836, Response filed Apr. 2, 2007 Final Office Action mailed Feb. 2, 2007", 24 pgs.
"U.S. Appl. No. 10/762,836, Response filed Jun. 21, 2006 Non-Final Office Action mailed Mar. 21, 2006", 23 pgs.
"International Search Report mailed Jun. 14, 2007 in corresponding PCT Application No. PCT/US2005/002158", 8 pgs.
"Written Opinion of the International Searching Authority mailed Jun. 14, 2007 in corresponding PCT Application No. PCT/US2005/002158", 8 pgs.
Adrain, C., et al., "Apoptosis-Associated Release of Smac/DIABLO From Mitochondria Requires Active Caspases and is Blocked by Bcl-2", *The EMBO Journal*, 20(23), (2001),6627-6636.
Berkers, C. R., et al., "Activity Probe for in vivo Profiling of the Specificity of Proteasome Inhibitor Bortezomib", *Nature Methods*, 2(5), (2005),357-362.
Fernandez, Y., et al., "Differential Regulation of Noxa in Normal Melanocytes and Melanoma Cells by Proteasome Inhibition: Therapeutic Implications", *Cancer Research*, 65(14), (2005),6294-6304.

(Continued)

Primary Examiner—Jon P Weber
Assistant Examiner—Paul C. Martin
(74) Attorney, Agent, or Firm—Schwegman, Lundberg & Woessner P.A.

(57) ABSTRACT

A method to detect the presence or amount of at least one molecule for an enzyme-mediated reaction in a multiplex luminogenic/nonluminogenic assay is provided.

19 Claims, 56 Drawing Sheets

OTHER PUBLICATIONS

Karlsson, J. O., et al., "Proteolytic Activity in Intact Sheets of Polarized Epithelial Cells as Determined by a Cell-Permeable Fluorogenic Substrate", *Cell Biology International*,24(4), (2000),235-243.

Kisselev, A. F., et al., "Importance of the Different Proteolytic Sites of the Proteasome and the Efficacy of Inhibitors Varies With Protein Substrate", *The Journal of Biological Chemistry*, 281(13), (Mar. 31, 2006),8582-8590.

Kisselev, A. F., et al., "Monitoring Activity and Inhibition of 26S Proteasomes With Fluorogenic Peptide Substrates", *Methods in Enzymology*, vol. 398, (2005),364-378.

Luker, G. D., et al., "Imaging 26S Proteasome Activity and Inhibition in Living Mice", *Nature Medicine*, 9(7), (2003),969-973.

Monsees, T., et al., "A Novel Bioluminogenic Assay for Alpha-Chymotrysin", *Journal of Bioluminescence And Chemiluninescence*, 10(4), (Jul. 1995),213-218.

Ramsby, M. L., "Differential Detergent Fractionation of Isolated Hepatocytes: Biochemical, Immunochemical and Two-Dimensional Gel Electrophoresis Characterization of Cytoskeletal and Noncytoskeletal Compartments", *Electrophoresis*, 15, (1994),265-277.

Wilkinson, J. C., et al., "Upstream Regulatory Role for XIAP in Receptor-Mediated Apoptosis", *Molecular and Cellular Biology*, 24(16), (2004),7003-7014.

"Apoptosis: Annexin V & Propidium Iodide—Freedom to Discover", *Acumen Bioscience Ltd.*, (Prior to Jan. 20, 2004),2 pgs.

"Beadlyte (r) Multiplex Assay Systems", *Product Guide, Upstate Cell Signalling Solutions*, (2002),12 pgs.

"Caspase-Glo tm 3/7 Assay", *Technical Bulletin No. 323, Promega Corporation*, (May 2003),13 pgs.

"Cell Cytotoxicity—Freedom to Discover", *Acumen Bioscience Ltd.*, (Prior to Jan. 20, 2004),2 pgs.

"Cell Proliferation—Freedom to Discover", *Acumen Bioscience Ltd.*, (Prior to Jan. 22, 2004),2 pgs.

"CellTiter-Blue tm Cell Viability Assay", *Technical Bulletin No. 317, Promega Corporation*, (Dec. 2002),12 pgs.

"CellTiter-Glo tm Luminescent Cell Viability Assay", *Technical Bullentin No. 288, Promega Corporation*, (May 2001),11 pgs.

"CytoTox-One tm Homogeneous Membrane Integrity Assay", *Technical Bulletin No. 306, Promega Corporation*, (May 2003),13 pgs.

"Dual-Light (r) Luminescent Report Gene Assay for Luciferase and Beta-Galactosidase", *Data Sheet, Applied Biosystems*, (2000),2 pgs.

"Multiplex Antibody Kits Custom Software & Hardware for Luminex tm", *MiraiBio Inc.*, (Prior to Jan. 20, 2004)),2 pgs.

Bronstein, I., et al., "Combined Luminescent Assays for Multiple Enzymes", *Bioluminescence and and Chemiluminescence: Molecular Reporting With Photons*, (International Symposium Proceedings),(1997),451-457.

Damour, Marc, et al., "Non-Radioactive Multiplex Kinase Activity Assay Using Beadlyte (r) Suspension Microarrays", (Prior to Jan. 20, 2004),1 pg.

De Jager, Wilco, et al., "Simultaneous Detection of 15 Human Cytokines in a Single Sample of Stimulated Peripheral Blood Mononuclear Cells", *Clinical and Diagnostic Laboratory Immunology*, 10(1), (2003), 133-139.

Dyer, Benjamin, et al., "A Noncommercial Dual Luciferase Enzyme Assay System for Report Gene Analysis", *Analytical Biochemistry*, 282, (2000),158-161.

Farfan, Abigail, et al., "Frequently Asked Questions Cytotox-One tm Homogeneous Membrane Integrity Assay", *Cell Notes, Issue 6*, (2003),19-20.

Gurtu, V., et al., "Fluorometric and Colorimetric Detection of Caspase-Activity Associated with Apoptosis", *Analytical Biochemistry*, 251, (1997),98-102.

Liu, Jingxue, et al., "Visualizing and Quantifying Protein Secretion Using a Renilla Luciferase-GFP Fusion Protein", *Luminescence*, 15, (2000),45-49.

Mandlekar, S., et al., "Activation of Caspase-3 and c-Jun NH2-terminal Kinase-1 Signaling Pathways in Tamoxifen-induced Apoptosis of Human Breast Cancer Cells", *Cancer Research*, 60, (2000),5995-6000.

Martin, Chris S., "Dual Luminescence-Based Reporter Gene Assay for Luciferase and Beta-Galactosidase", *BioTechniques*, 21(3), (1996),520-524.

Nolkrantz, Kerstin, et al., "Functional Screening of Intracellular Proteins in Single Cells and in Patterned Cell Arrays Using Electroporation", *Analytical Chemistry*, 74(16), (2002),4300-4305.

Qazi, Saara, et al., "A Novel Dual Reporter Assay for Studying Intracellular Bacterial Pathogens", *Luminescence*, 17, (Abstract Only), XIIth International Symposium on Bioluminescence and Chemiluminescence,(2002),p. 106.

Sohnlein, Petra, et al., "Fast and Flexible Setup of Homogeneous Protein Assays Employing 6xHis-Tag Technology—High Sensitivy and Signal-to-Noise Ratios", (Qiagen (r) LiquiChip tm),(Published prior to Jan. 20, 2004),13 pgs.

Timiryasova, T. M., et al., "Visualization of Vaccinia Virus Infection Using the Renilla-Luciferase-GFP Fusion Protein", *Bioluminescence and Chemiluminescence*, (11th International Proceedings),(2001),457-460.

Wang, Y., et al., "The Renilla Luciferase-Modified GFP Fusion Protein is Functional in Transformed Cells", *Bioluminescence and Chemiluminescence: Molecular Report with Photons*, (Symposium Proceedings,,(1997),419-422.

Yu, Yong A., et al., "Inducible Gene Expression in Vivo Using a Renilla Luciferase—GFP Fusion Construct", *Bioluminescence and Chemiluminescence*, (11th International Symposium Proceedings),(2000),465-468.

"U.S. Appl. No. 10/762,836 Notice of Allowance mailed Mar. 25, 2008", NOAR,10 pgs.

"U.S. Appl. No. 10/762,836 Notice of Allowance mailed Nov. 7, 2007", 8 pgs.

"U.S. Appl. No. 11/510,278, Response to Restriction Requirement and Preliminary Amendment filed Mar. 3, 2008 in Response to Restriction Requirement mailed Jan. 31, 2008.", 8.

Bond, J. S., et al., "Intracellular Proteases", *Annual Review of Biochemistry*, 56, (1987),333-364.

Constam, D. B., et al., "Purumycin-Sensitive Aminopeptidase", *The Journal of Biological Chemistry*, 270(45), (1995),26931-26939.

Cook, J. A., et al., "Viability Measurements in Mammalian Cell Systems", *Analytical Biochemistry*, 179, (1989),1-7.

Fenteany, G, et al., "Inhibition of proteasome activities and subunit-specific amino-terminal threonine modification by lactacystin", *Science*, 268(5211), (1995),726-731.

Fernandes-Alnemri, T., et al., "In vitro activation of CPP32 and Mch3 by Mch4, a novel human apoptotic cysteine protease containing two FADD-like domains", *Proceedings of National Academy of Science USA*, 93(15), (Jul. 1996),7464-7469.

Haunstetter, A., et al., "Apoptosis: Basic Mechanisms and Implications for Cardiovascular Disease", *Circulation Research*, 82, (1998),1111-1129.

Liu, J., et al., "Visualizing And Quantifying Protein Secretion Using A Renialla Luciferase-GFP Fusion Protein", *Luciferase*, 15(1), (Feb. 2000),45-49.

Masuda-Nishimura, I., et al., "Development of a rapid positive/absent test for coliforms using sensitive bioluminescence assay", *Letters in Applied Microbiology*, 30, (2000),130-135.

Mellgren, R. L., et al., "Specificities of Cell Permeant Peptidyl Inhibitors for the Proteinase Activities of u-Calpain and the 20 S Proteasome", *The Journal of Biological Chemistry*, 272(47),29899-29903.

Miska, Werner, et al., "Synthesis and Characterization of Luciferin Derivatives for Use in Bioluminescence Enhanced Enzyme Immunoassays", *Journal of Clinical Chemistry and Clinical Biochemistry*, 25, (1987),23-30.

Monsees, Thomas, et al., "A Novel Bioluminogenic Assay for a-Chymotrypsin", *Journal of Bioluminescence and Chemiluminescence*, 10, (1995),213-218.

Monsees, Thomas, et al., "Synthesis and Characterization of a Bioluminogenic Substrate for a-Chymotrypsin", *Analytical Biochemistry*, 221, (1994),329-334.

Myers, M. A., "Direct Measurement of Cell Numbers in Microtitre Plate Cultures Using the Fluorescent Dye SYBR Green", *Journal of Immunological Methods*, 212, (1998),99-103.

Nicholson, Donald W., et al., "Identification and inhibition of the ICE/CED-3 protease necessary for mammalian apoptosis", *Nature*, 376, (Jul. 1995),37-43.

O'Connell, et al., "Live/Dead Assay for Cell Viability; AfCS Procedure Protocol PP00000023 (2002)", http://wwwsignaling-gateway.org/data/cgi-bin/ProtocolFile.cgi/afcs_PP00000023.pdf?pid=PP00000023, (2002),1-5 pgs.

Riss, T. L., et al., "Use of Multiple Assay Endpoints to Investigate the Effects of Incubation Time, Dose of Toxin, and Plating in Cell-Based Cytotoxicity Assays", *Assay and Drug Development Technologies*, 2(1), (Abstract Only),(2004),1 pg.

Syntichaki, P., et al., "The Biochemistry of Neuronal Necrosis: Rouge Biology?", *Nature Reviews*, 4, (2003),672-684.

Tewari, Muneesh, et al., "Yama/CPP32b, a Mammalian Homolog of CED-3, Is a CrmA-Inhibitable Protease That Cleaves the Death Substrate Poly(ADP-Ribose) Polymerase", *Cell*, 81, (Jun. 1995),801-809.

Thornberry, Nancy A., et al., "A novel heterodimeric cysteine protease is requried for interleukin-1b processing in monocytes", *Nature*, 356, (Apr. 1992),768-774.

Tran, T. V., et al., "Dipeptidyl Peptidase I: Importance of Progranzyme Activation Sequences, Other Dipeptide Sequences, and the N-Terminal Amino Group of Synthetic Substrates for Enzyme Activity", *Archives of Biochemistry and Biophysics*, 403, (2002),160-170.

"U.S. Appl. No. 11/510,278, Restriction Requirement mailed Jan. 31, 2008", 8 pgs.

"U.S. Appl. No. 11/510,278, Response filed Nov. 26, 2008 to Non-Final Office Action mailed May 30, 2008", 18 pgs.

"U.S. Appl. No. 11/510,278, Non-Final Office Action mailed Jan. 22, 2009", 21 pgs.

"International Application Serial No. PCT/US2005/002158, International Search Report mailed Jun. 14, 2007", 8 pgs.

"International Application Serial No. PCT/US2006/033622, International Search Report mailed Dec. 28, 2006", 6 pgs.

"International Application Serial No. PCT/US2006/033622, Written Opinion mailed Dec. 28, 2006", 7 pgs.

"U.S. Appl. No. 11/510,278, Non-Final Office Action mailed May 30, 2008", 13 pgs.

"European Application Serial No. 06790059.7, Communication mailed Sep. 23, 2008", 2 pgs.

Kisselev, A. F., et al., "The Caspase-Like Sites of Proteasomes, Their Substrate Specificity, New Inhibitors and Substrates, and Allosteric Interactions with the Trypsin-Like Sites", *The Journal of Biological Chemistry*, 278(38), (2003), 35869-35877.

Princiotta, M. F. et al., "Cells Adapted to the Proteasome Inhibitor 4-Hydroxy-5-iodo-3-Nitrophenylacetyl-Leu-Leu-Leucinal-Vinyl Sulfone Require Enzymatically Active Proteasome for Continued Survival", *Proc. Natl. Acad. Sci. USA*, 98(2), (2001), 513-519.

\* cited by examiner

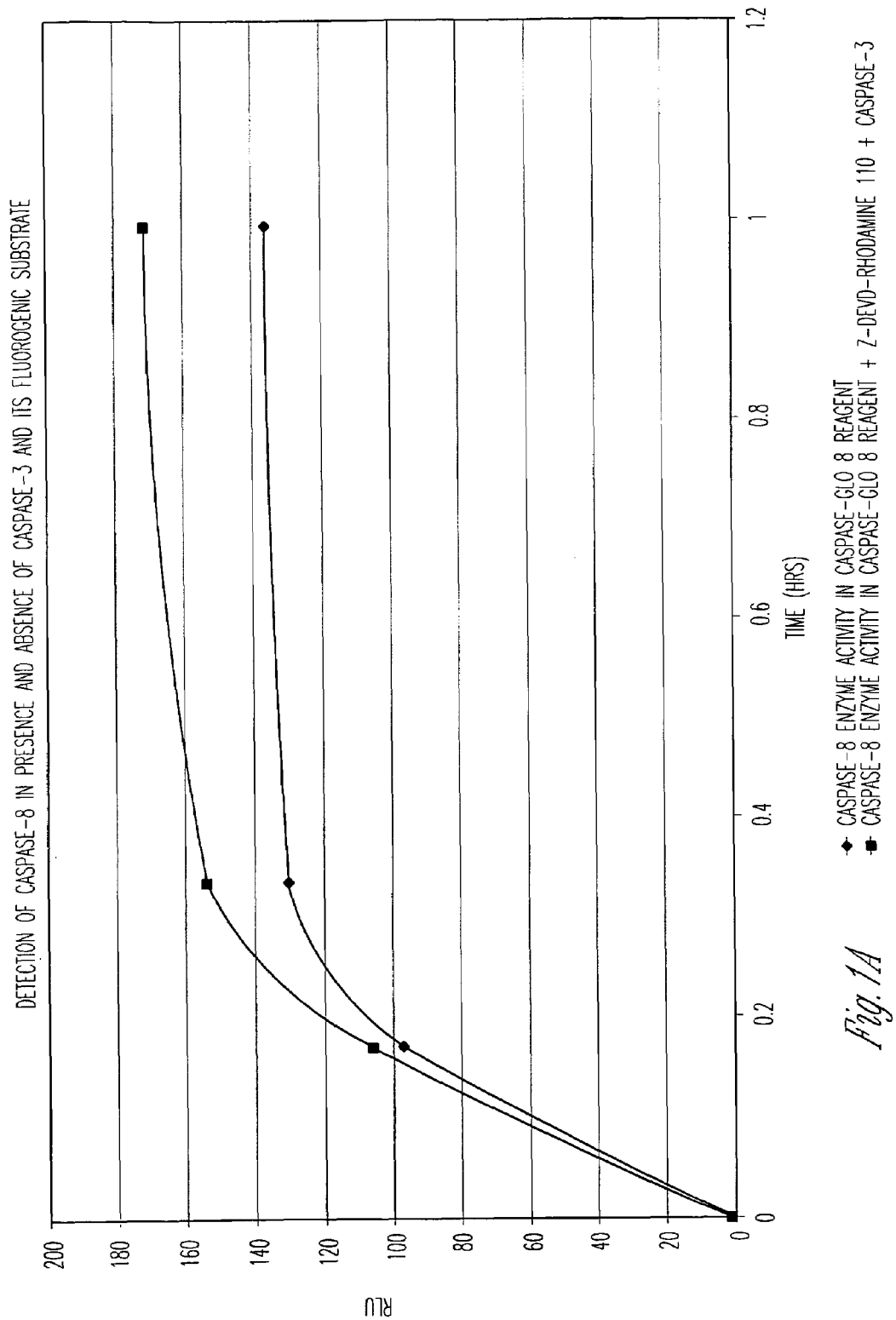

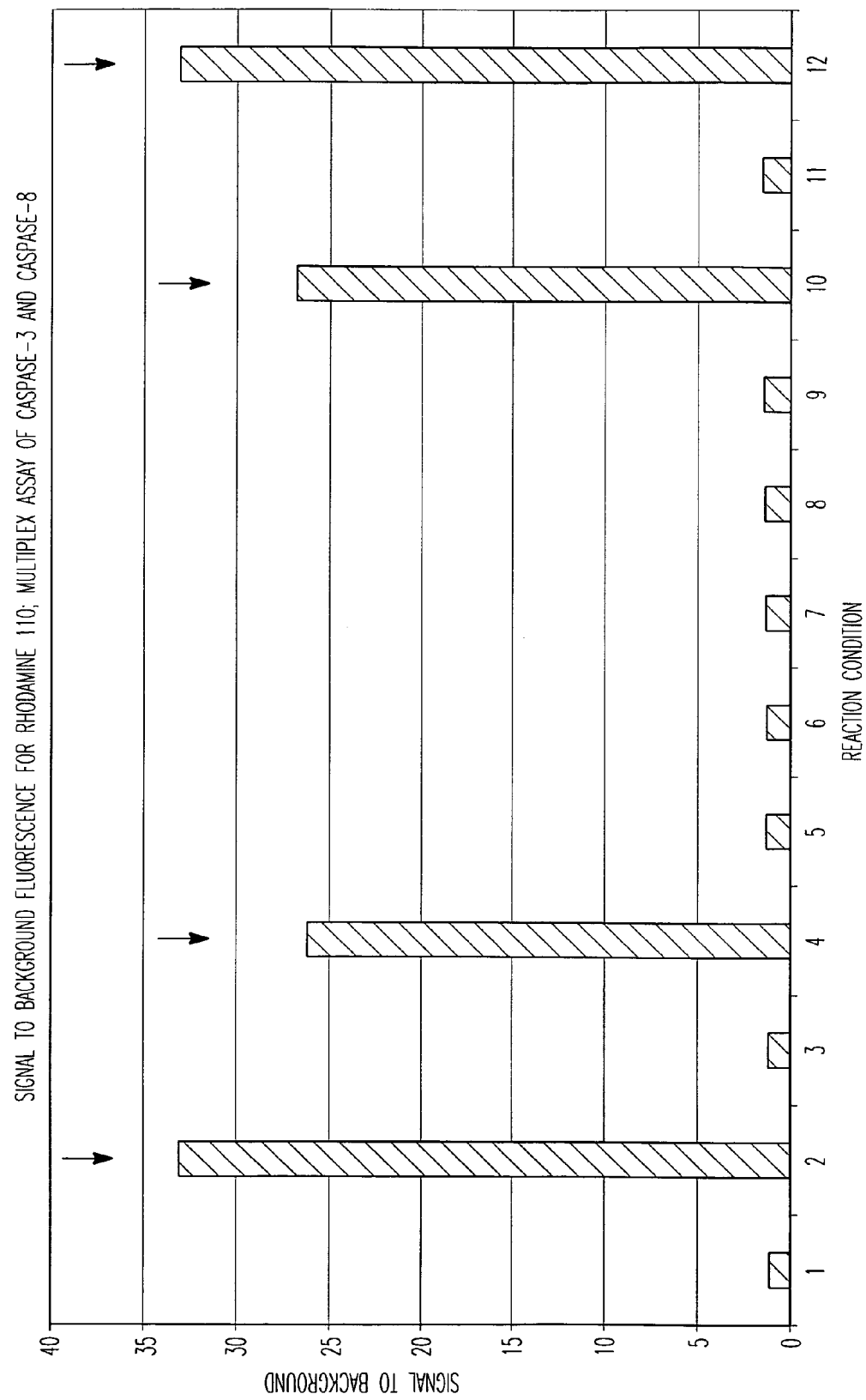

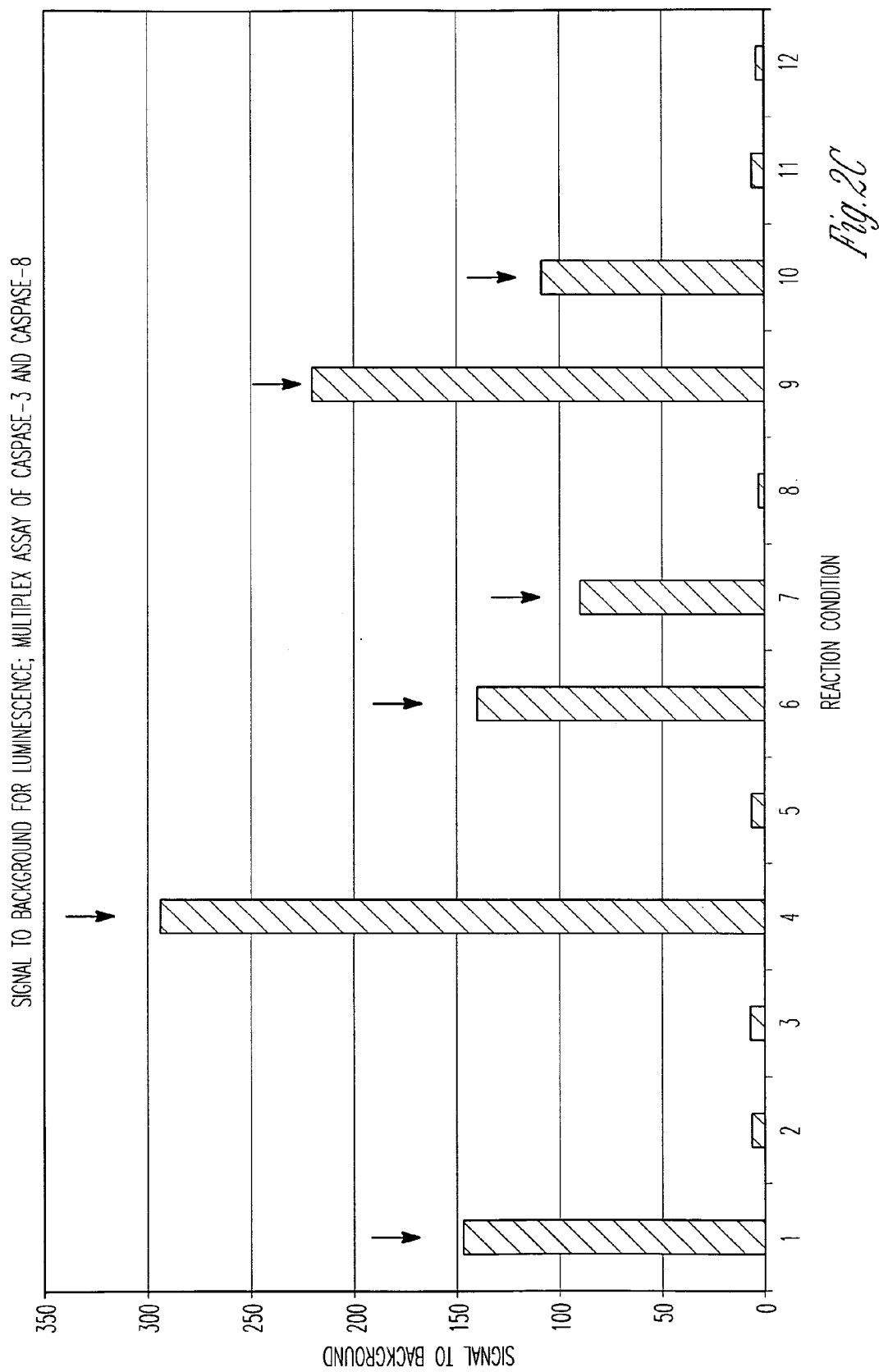

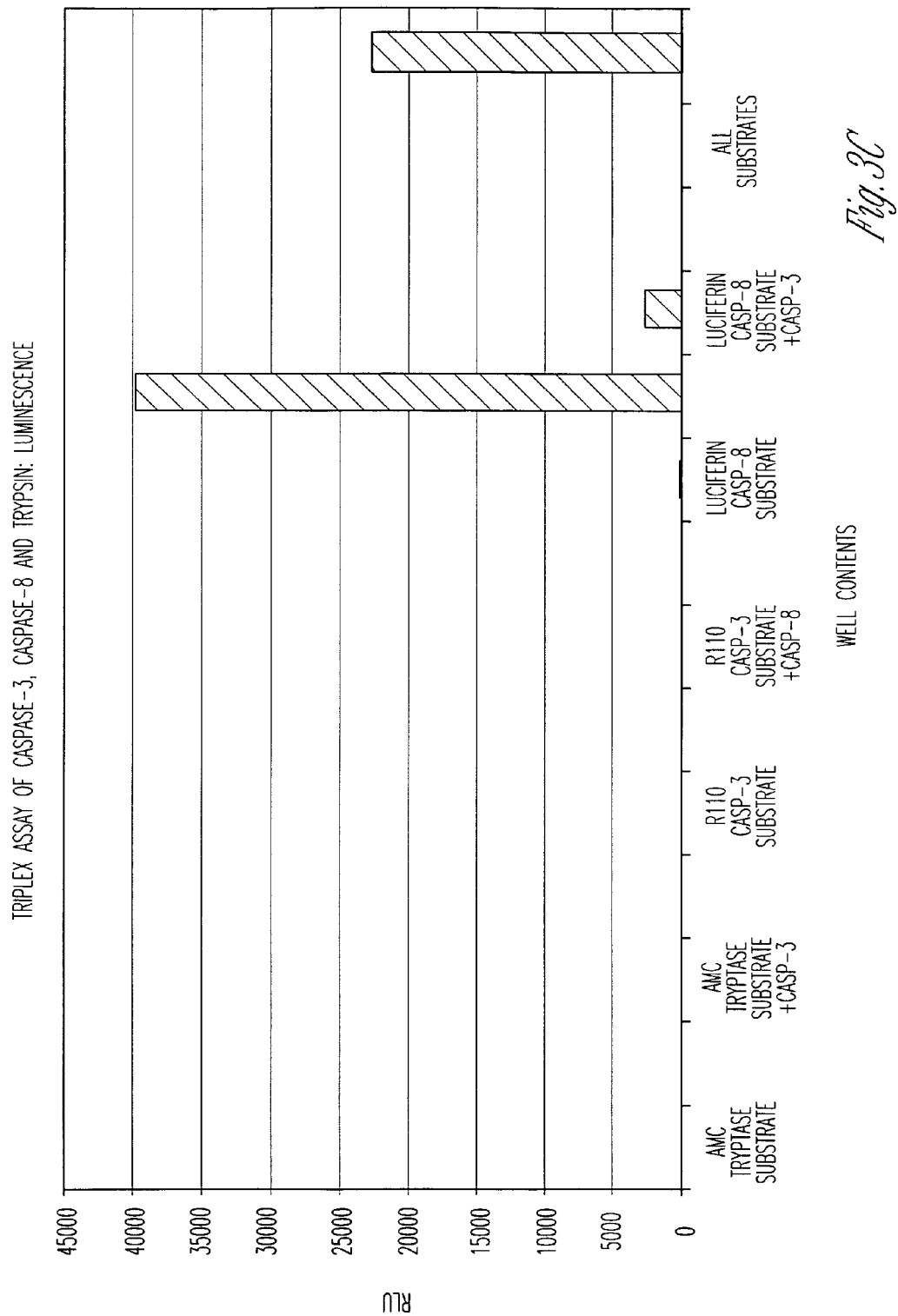

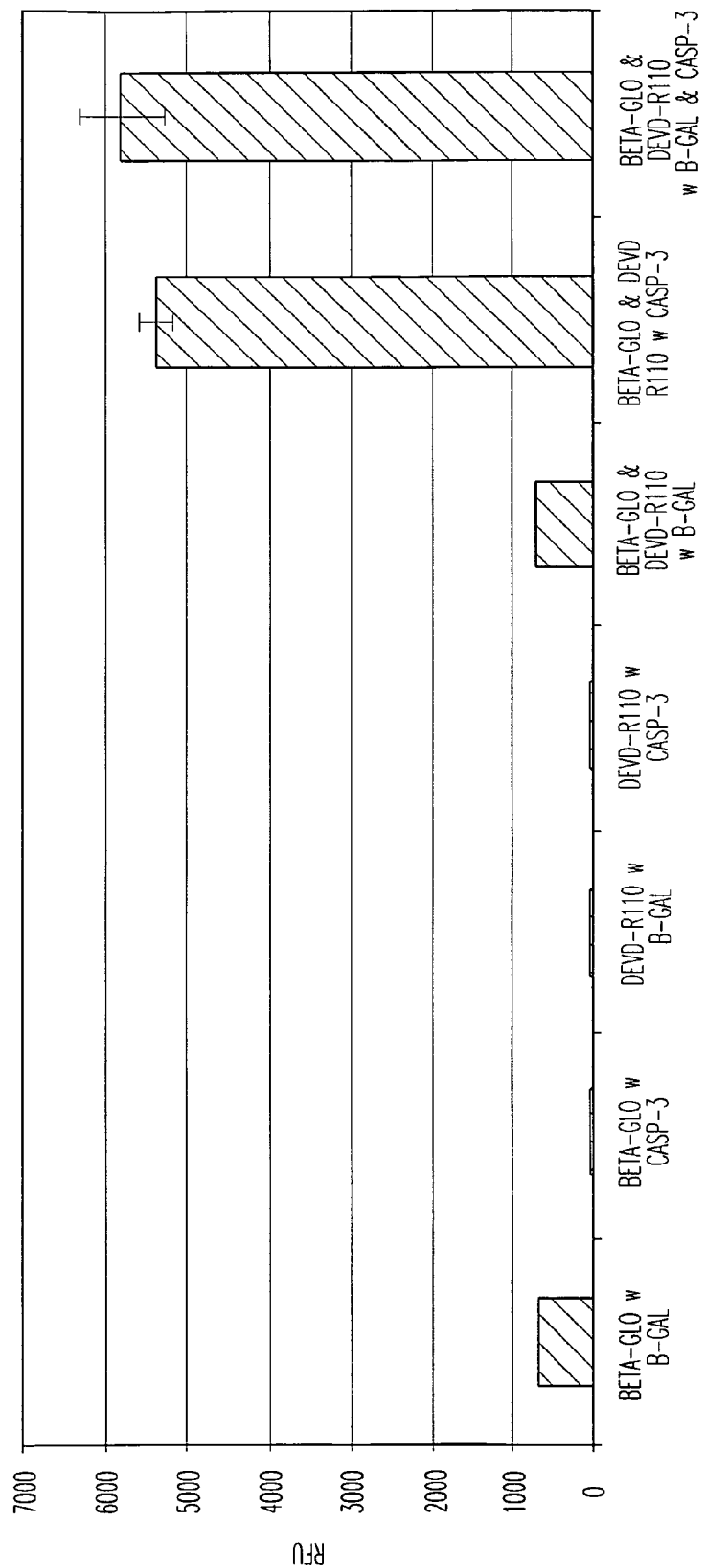

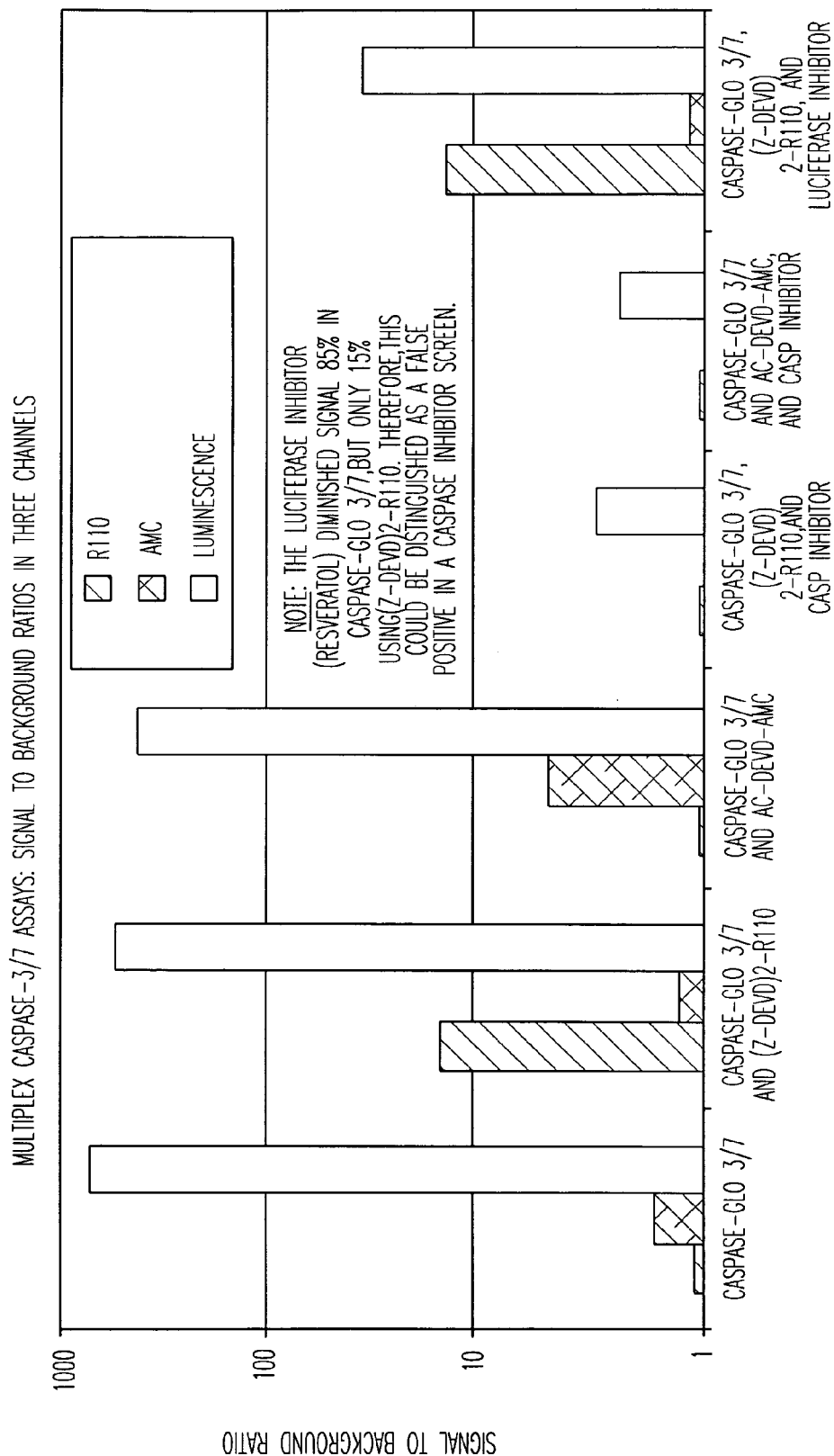

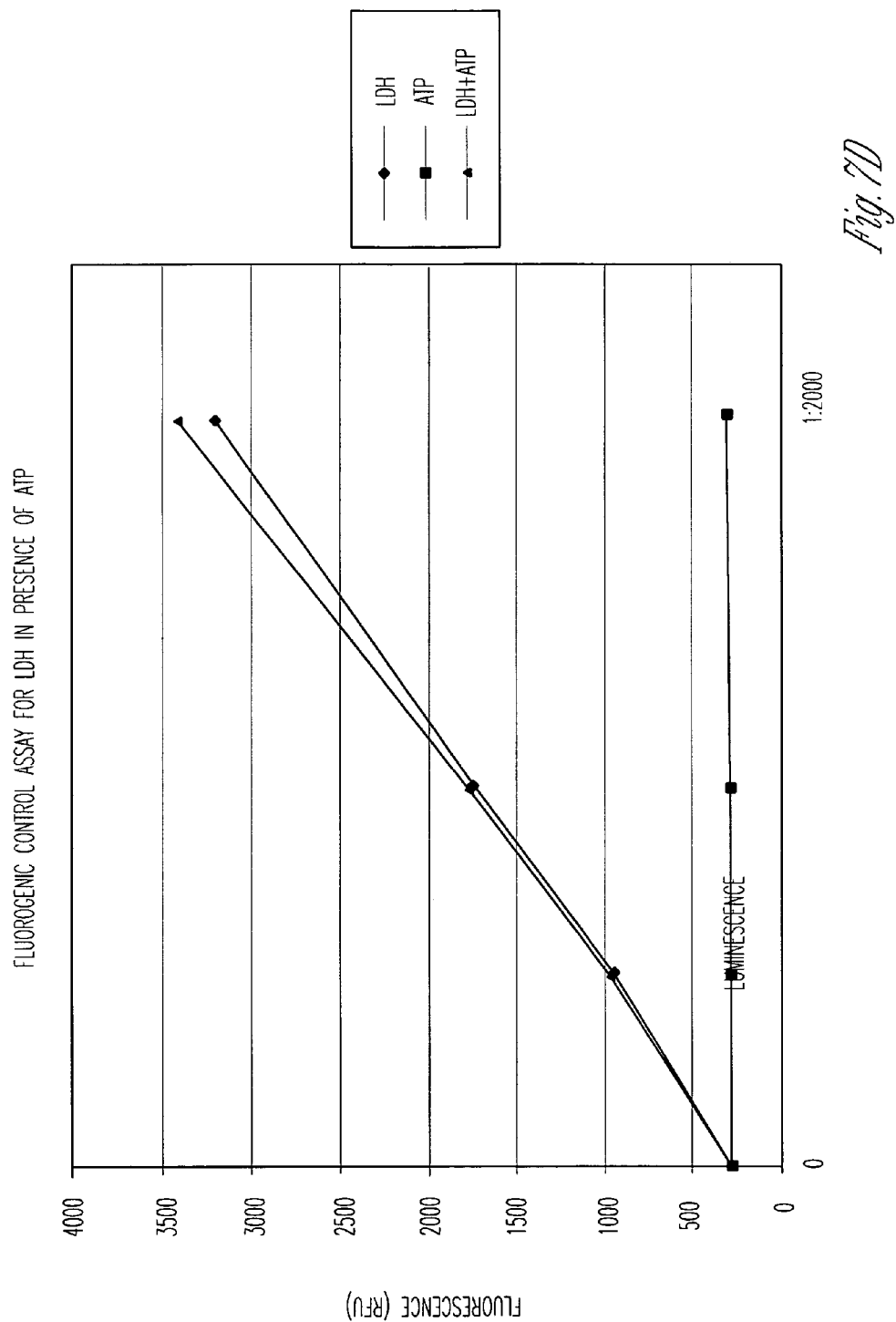

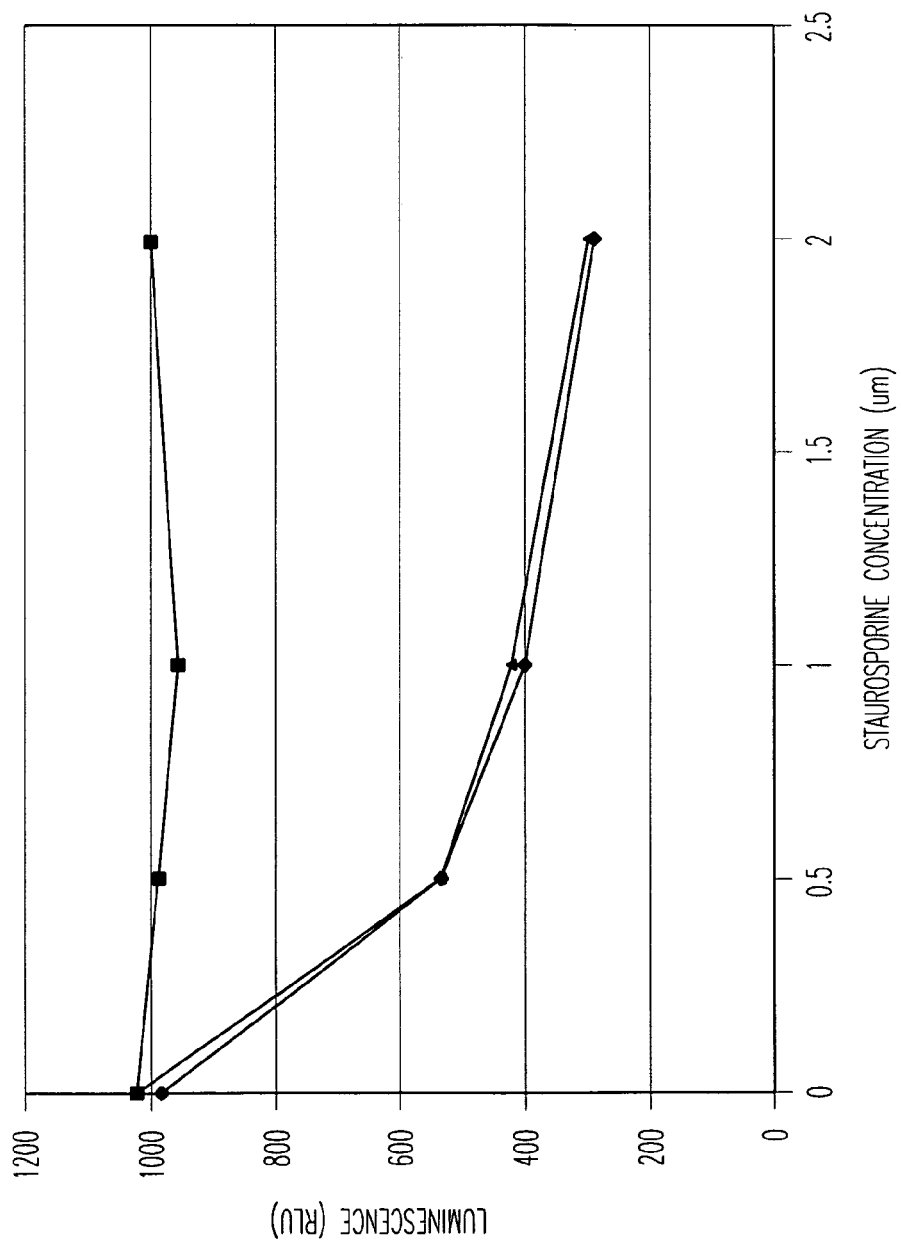

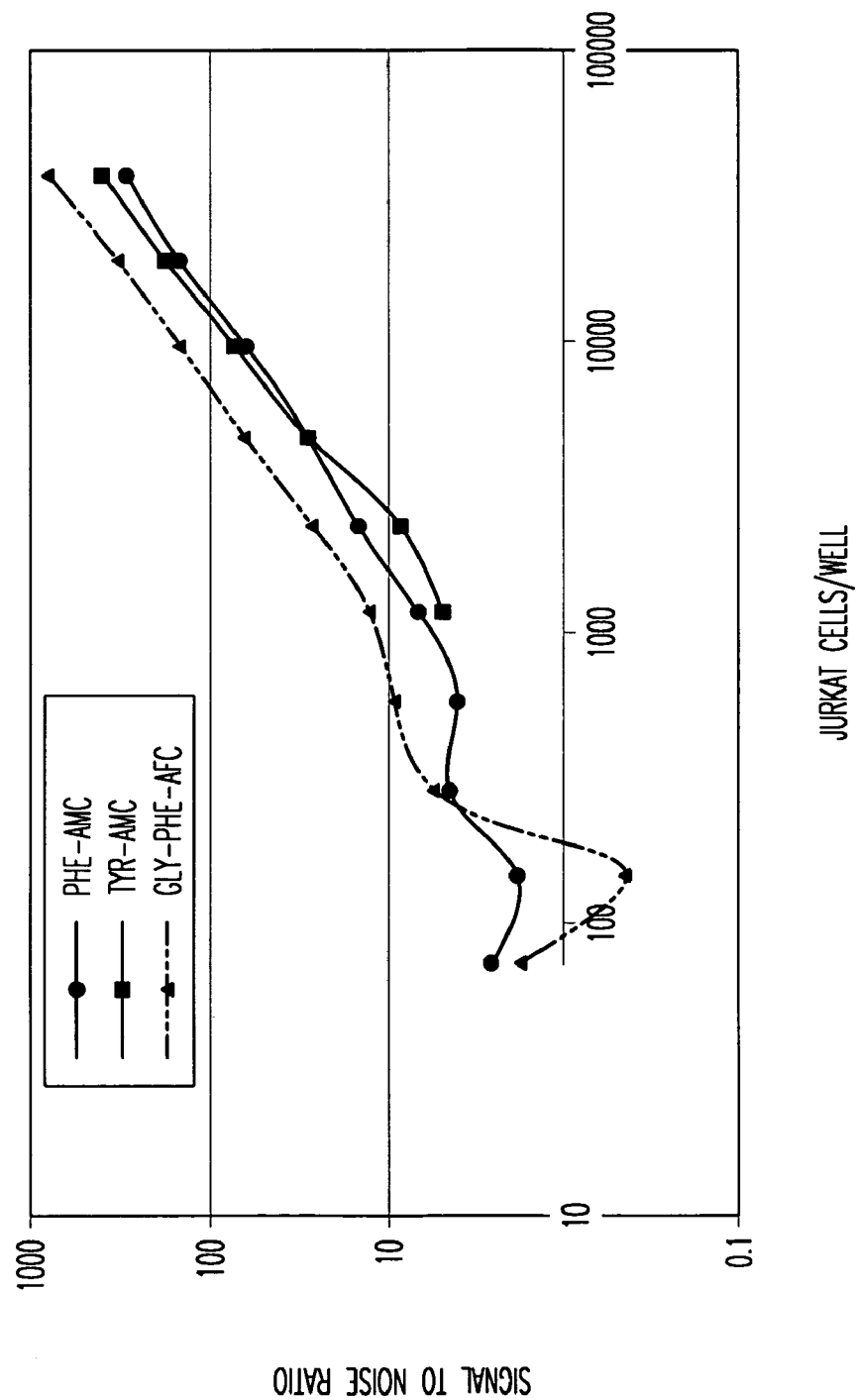

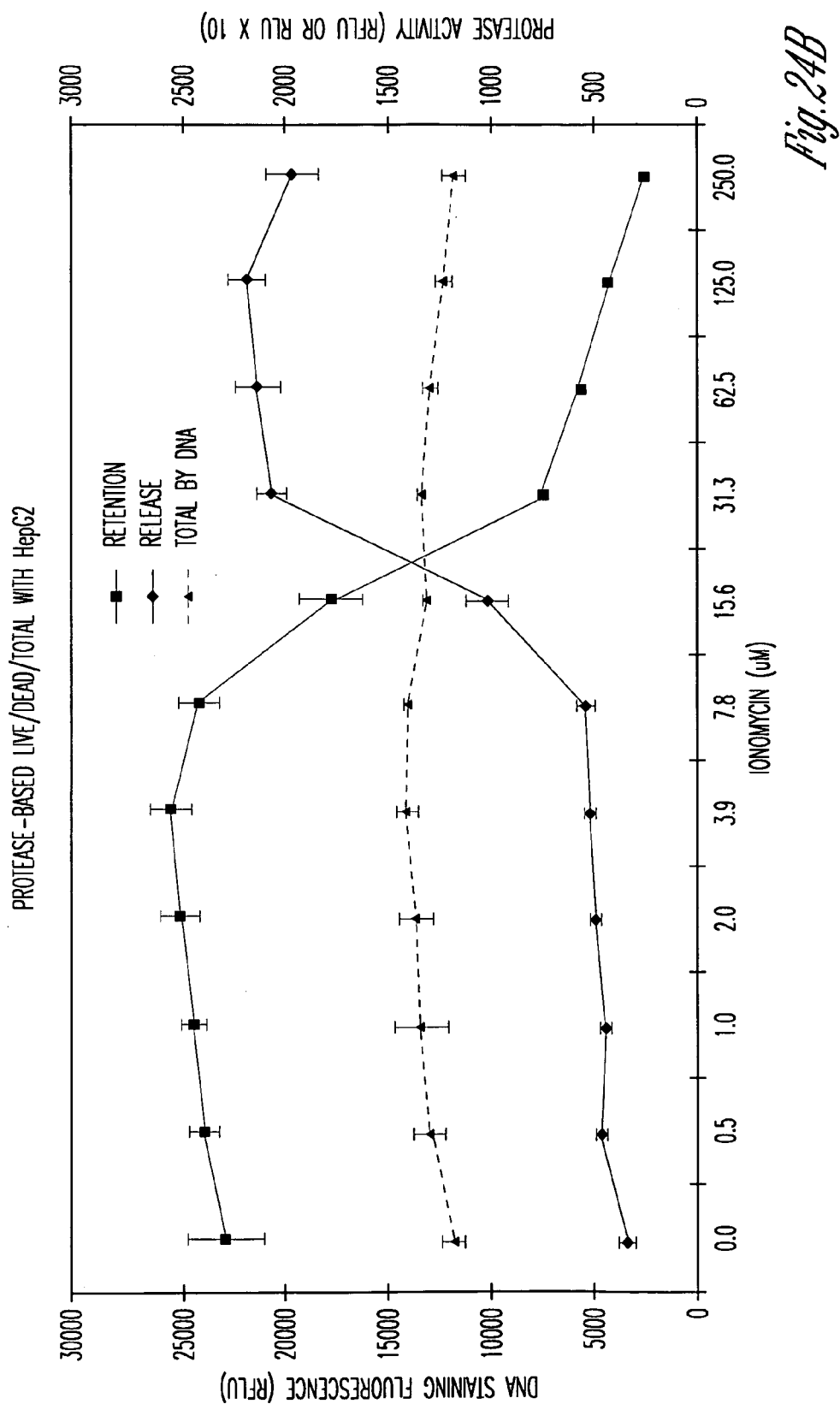

SEQUENCE LISTING

```
<160> NUMBER OF SEQ ID NOS: 34

<210> SEQ ID NO 1
<211> LENGTH: 4
<212> TYPE: PRT
<213> ORGANISM: Artificial Sequence
<220> FEATURE:
<223> OTHER INFORMATION: A synthetic substrate

<400> SEQUENCE: 1

Asp Glu Val Asp
 1

<210> SEQ ID NO 2
<211> LENGTH: 4
<212> TYPE: PRT
<213> ORGANISM: Artificial Sequence
<220> FEATURE:
<223> OTHER INFORMATION: A synthetic substrate

<400> SEQUENCE: 2

Trp Glu His Asp
 1

<210> SEQ ID NO 3
<211> LENGTH: 4
<212> TYPE: PRT
<213> ORGANISM: Artificial Sequence
<220> FEATURE:
<223> OTHER INFORMATION: A synthetic substrate

<400> SEQUENCE: 3

Leu Glu His Asp
 1

<210> SEQ ID NO 4
<211> LENGTH: 4
<212> TYPE: PRT
<213> ORGANISM: Artificial Sequence
<220> FEATURE:
<223> OTHER INFORMATION: A synthetic substrate

<400> SEQUENCE: 4

Val Glu Ile Asp
 1

<210> SEQ ID NO 5
<211> LENGTH: 4
<212> TYPE: PRT
<213> ORGANISM: Artificial Sequence
<220> FEATURE:
<223> OTHER INFORMATION: A synthetic substrate

<400> SEQUENCE: 5

Val Glu Val Asp
 1
```

```
<210> SEQ ID NO 6
<211> LENGTH: 4
<212> TYPE: PRT
<213> ORGANISM: Artificial Sequence
<220> FEATURE:
<223> OTHER INFORMATION: A synthetic substrate

<400> SEQUENCE: 6

Val Glu His Asp
 1

<210> SEQ ID NO 7
<211> LENGTH: 4
<212> TYPE: PRT
<213> ORGANISM: Artificial Sequence
<220> FEATURE:
<223> OTHER INFORMATION: A synthetic substrate

<400> SEQUENCE: 7

Ile Glu Thr Asp
 1

<210> SEQ ID NO 8
<211> LENGTH: 4
<212> TYPE: PRT
<213> ORGANISM: Artificial Sequence
<220> FEATURE:
<223> OTHER INFORMATION: A synthetic substrate

<400> SEQUENCE: 8

Ala Glu Val Asp
 1

<210> SEQ ID NO 9
<211> LENGTH: 4
<212> TYPE: PRT
<213> ORGANISM: Artificial Sequence
<220> FEATURE:
<223> OTHER INFORMATION: A synthetic substrate
<220> FEATURE:
<221> NAME/KEY: SITE
<222> LOCATION: 3
<223> OTHER INFORMATION: Xaa = any amino acid

<400> SEQUENCE: 9

Leu Glu Xaa Asp
 1

<210> SEQ ID NO 10
<211> LENGTH: 4
<212> TYPE: PRT
<213> ORGANISM: Artificial Sequence
<220> FEATURE:
<223> OTHER INFORMATION: A synthetic substrate
<220> FEATURE:
<221> NAME/KEY: SITE
<222> LOCATION: 3
<223> OTHER INFORMATION: Xaa = any amino acid

<400> SEQUENCE: 10

Val Glu Xaa Asp
 1

<210> SEQ ID NO 11
<211> LENGTH: 4
<212> TYPE: PRT
<213> ORGANISM: Artificial Sequence
<220> FEATURE:
<223> OTHER INFORMATION: A synthetic substrate
```

```
<400> SEQUENCE: 11

Ile Glu His Asp
1

<210> SEQ ID NO 12
<211> LENGTH: 4
<212> TYPE: PRT
<213> ORGANISM: Artificial Sequence
<220> FEATURE:
<223> OTHER INFORMATION: A synthetic substrate

<400> SEQUENCE: 12

Pro Glu His Asp
1

<210> SEQ ID NO 13
<211> LENGTH: 4
<212> TYPE: PRT
<213> ORGANISM: Artificial Sequence
<220> FEATURE:
<223> OTHER INFORMATION: A synthetic substrate

<400> SEQUENCE: 13

Glx Glu Val Asp
1

<210> SEQ ID NO 14
<211> LENGTH: 4
<212> TYPE: PRT
<213> ORGANISM: Artificial Sequence
<220> FEATURE:
<223> OTHER INFORMATION: A synthetic substrate

<400> SEQUENCE: 14

Leu Glu Thr Asp
1

<210> SEQ ID NO 15
<211> LENGTH: 4
<212> TYPE: PRT
<213> ORGANISM: Artificial Sequence
<220> FEATURE:
<223> OTHER INFORMATION: A synthetic substrate
<220> FEATURE:
<221> NAME/KEY: SITE
<222> LOCATION: 1
<223> OTHER INFORMATION: Xaa = Z, Y, D, L, V, I, A, W or P
<220> FEATURE:
<221> NAME/KEY: SITE
<222> LOCATION: 2
<223> OTHER INFORMATION: Xaa = V or E
<220> FEATURE:
<221> NAME/KEY: SITE
<222> LOCATION: 3
<223> OTHER INFORMATION: Xaa = any amino acid

<400> SEQUENCE: 15

Xaa Xaa Xaa Asp
1

<210> SEQ ID NO 16
<211> LENGTH: 6
<212> TYPE: PRT
<213> ORGANISM: Artificial Sequence
<220> FEATURE:
<223> OTHER INFORMATION: A synthetic substrate

<400> SEQUENCE: 16
```

```
Ala Ala Phe Ala Ala Phe
 1               5

<210> SEQ ID NO 17

<400> SEQUENCE: 17

000

<210> SEQ ID NO 18
<211> LENGTH: 4
<212> TYPE: PRT
<213> ORGANISM: Artificial Sequence
<220> FEATURE:
<223> OTHER INFORMATION: A synthetic substrate

<400> SEQUENCE: 18

Leu Leu Val Tyr
 1

<210> SEQ ID NO 19
<211> LENGTH: 5
<212> TYPE: PRT
<213> ORGANISM: Artificial Sequence
<220> FEATURE:
<223> OTHER INFORMATION: A synthetic substrate
<220> FEATURE:
<221> NAME/KEY: SITE
<222> LOCATION: 1
<223> OTHER INFORMATION: Xaa = W or L
<220> FEATURE:
<221> NAME/KEY: SITE
<222> LOCATION: 5
<223> OTHER INFORMATION: Xaa = one or more amino acids

<400> SEQUENCE: 19

Xaa Glu His Asp Xaa
 1               5

<210> SEQ ID NO 20
<211> LENGTH: 5
<212> TYPE: PRT
<213> ORGANISM: Artificial Sequence
<220> FEATURE:
<223> OTHER INFORMATION: A synthetic substrate
<220> FEATURE:
<221> NAME/KEY: SITE
<222> LOCATION: 3
<223> OTHER INFORMATION: Xaa = one or more amino acids
<220> FEATURE:
<221> NAME/KEY: SITE
<222> LOCATION: 5
<223> OTHER INFORMATION: Xaa = one or more amino acids

<400> SEQUENCE: 20

Asp Glu Xaa Asp Xaa
 1               5

<210> SEQ ID NO 21
<211> LENGTH: 5
<212> TYPE: PRT
<213> ORGANISM: Artificial Sequence
<220> FEATURE:
<223> OTHER INFORMATION: A synthetic substrate
<220> FEATURE:
<221> NAME/KEY: SITE
<222> LOCATION: 1
<223> OTHER INFORMATION: Xaa = L or V
<220> FEATURE:
<221> NAME/KEY: SITE
```

```
<222> LOCATION: 3
<223> OTHER INFORMATION: Xaa = one or more amino acids
<220> FEATURE:
<221> NAME/KEY: SITE
<222> LOCATION: 5
<223> OTHER INFORMATION: Xaa = one or more amino acids

<400> SEQUENCE: 21

Xaa Glu Xaa Asp Xaa
 1               5

<210> SEQ ID NO 22
<211> LENGTH: 5
<212> TYPE: PRT
<213> ORGANISM: Artificial Sequence
<220> FEATURE:
<223> OTHER INFORMATION: A synthetic substrate
<220> FEATURE:
<221> NAME/KEY: SITE
<222> LOCATION: 5
<223> OTHER INFORMATION: Xaa = one or more amino acids

<400> SEQUENCE: 22

Ile Glu Gly Arg Xaa
 1               5

<210> SEQ ID NO 23
<211> LENGTH: 7
<212> TYPE: PRT
<213> ORGANISM: Artificial Sequence
<220> FEATURE:
<223> OTHER INFORMATION: A synthetic substrate
<220> FEATURE:
<221> NAME/KEY: SITE
<222> LOCATION: 3
<223> OTHER INFORMATION: Xaa = one or more amino acids
<220> FEATURE:
<221> NAME/KEY: SITE
<222> LOCATION: 5
<223> OTHER INFORMATION: Xaa = one or more amino acids
<220> FEATURE:
<221> NAME/KEY: SITE
<222> LOCATION: 7
<223> OTHER INFORMATION: Xaa = S or G

<400> SEQUENCE: 23

Glu Asn Xaa Tyr Xaa Gln Xaa
 1               5

<210> SEQ ID NO 24
<211> LENGTH: 5
<212> TYPE: PRT
<213> ORGANISM: Artificial Sequence
<220> FEATURE:
<223> OTHER INFORMATION: A synthetic substrate
<220> FEATURE:
<221> NAME/KEY: SITE
<222> LOCATION: 5
<223> OTHER INFORMATION: Xaa = one or more amino acids

<400> SEQUENCE: 24

Pro Arg Asn Lys Xaa
 1               5

<210> SEQ ID NO 25
<211> LENGTH: 14
<212> TYPE: PRT
<213> ORGANISM: Artificial Sequence
<220> FEATURE:
<223> OTHER INFORMATION: A synthetic substrate
<220> FEATURE:
```

```
<221> NAME/KEY: SITE
<222> LOCATION: 6
<223> OTHER INFORMATION: Xaa = K or N
<220> FEATURE:
<221> NAME/KEY: SITE
<222> LOCATION: 7
<223> OTHER INFORMATION: Xaa = M or L

<400> SEQUENCE: 25

Glu Ile Ser Glu Val Xaa Xaa Asp Ala Glu Phe Arg His Asp
 1               5                  10

<210> SEQ ID NO 26
<211> LENGTH: 10
<212> TYPE: PRT
<213> ORGANISM: Artificial Sequence
<220> FEATURE:
<223> OTHER INFORMATION: A synthetic substrate

<400> SEQUENCE: 26

Ser Glu Val Asn Leu Asp Ala Glu Phe Arg
 1               5                  10

<210> SEQ ID NO 27
<211> LENGTH: 4
<212> TYPE: PRT
<213> ORGANISM: Artificial Sequence
<220> FEATURE:
<223> OTHER INFORMATION: A synthetic substrate

<400> SEQUENCE: 27

Pro Arg Asn Lys
 1

<210> SEQ ID NO 28
<211> LENGTH: 4
<212> TYPE: PRT
<213> ORGANISM: Artificial Sequence
<220> FEATURE:
<223> OTHER INFORMATION: A synthetic substrate

<400> SEQUENCE: 28

Gly Phe Gly Phe
 1

<210> SEQ ID NO 29
<211> LENGTH: 5
<212> TYPE: PRT
<213> ORGANISM: Artificial Sequence
<220> FEATURE:
<223> OTHER INFORMATION: A synthetic substrate

<400> SEQUENCE: 29

Arg Leu Arg Gly Gly
 1               5

<210> SEQ ID NO 30
<211> LENGTH: 4
<212> TYPE: PRT
<213> ORGANISM: Artificial Sequence
<220> FEATURE:
<223> OTHER INFORMATION: A synthetic substrate

<400> SEQUENCE: 30

Leu Arg Gly Gly
 1
```

-continued

```
<210> SEQ ID NO 31
<211> LENGTH: 8
<212> TYPE: PRT
<213> ORGANISM: Artificial Sequence
<220> FEATURE:
<223> OTHER INFORMATION: A synthetic substrate

<400> SEQUENCE: 31

Arg Pro Phe His Leu Leu Val Tyr
 1               5

<210> SEQ ID NO 32
<211> LENGTH: 4
<212> TYPE: PRT
<213> ORGANISM: Artificial Sequence
<220> FEATURE:
<223> OTHER INFORMATION: A synthetic substrate

<400> SEQUENCE: 32

Glu Ala Ala Phe
 1

<210> SEQ ID NO 33

<400> SEQUENCE: 33

000

<210> SEQ ID NO 34
<211> LENGTH: 9
<212> TYPE: PRT
<213> ORGANISM: Artificial Sequence
<220> FEATURE:
<223> OTHER INFORMATION: A synthetic substrate

<400> SEQUENCE: 34

Ser Arg Pro Phe His Leu Leu Val Tyr
 1               5
```

LUMINOGENIC AND NONLUMINOGENIC MULTIPLEX ASSAY

CROSS-REFERENCE TO RELATED APPLICATIONS

This application is a continuation of PCT Application Ser. No. PCT/US2005/002158, filed Jan. 24, 2005 and published on Aug. 11, 2005 as WO 2005/073722 A2, which is a continuation-in-part of U.S. application Ser. No. 10/762,836, filed Jan. 22, 2004, the disclosure of which is incorporated by reference herein.

BACKGOUND OF THE INVENTION

Luminescence is produced in certain organisms as a result of a luciferase-mediated oxidation reaction. Luciferase genes from a wide variety of vastly different species, particularly the luciferase genes of Photinus pyralis and Photuris pennsylvanica (fireflies of North America), Pyrophorus plagiophthalamus (the Jamaican click beetle), Renilla reniformis (the sea pansy), and several bacteria (e.g., Xenorhabdus luminescens and Vibrio spp), are extremely popular luminescence reporter genes. Firefly luciferase is also a popular reporter for determining ATP concentrations, and, in that role, is widely used to detect biomass. Luminescence is also produced by other enzymes when those enzymes are mixed with certain synthetic substrates, for instance, alkaline phosphatase and adamantyl dioxetane phosphate, or horseradish peroxidase and luminol.

Luciferase genes are widely used as genetic reporters due to the non-radioactive nature, sensitivity, and extreme linear range of luminescence assays. For instance, as few as $10^{-20}$ moles of firefly luciferase can be detected. Consequently, luciferase assays of gene activity are used in virtually every experimental biological system, including both prokaryotic and eukaryotic cell cultures, transgenic plants and animals, and cell-free expression systems. Similarly, luciferase assays used to determine ATP concentration are highly sensitive, enabling detection to below $10^{-16}$ moles.

Luciferases can generate light via the oxidation of enzyme-specific substrates, e.g., luciferins. For firefly luciferase and all other beetle luciferases, light generation occurs in the presence of magnesium ions, oxygen, and ATP. For anthozoan luciferases, including Renilla luciferase, only oxygen is required along with the substrate coelentrazine. Generally, in luminescence assays to determine genetic activity, reaction substrates and other luminescence activating reagents are introduced into a biological system suspected of expressing a reporter enzyme. Resultant luminescence, if any, is then measured using a luminometer or any suitable radiant energy-measuring device. The assay is very rapid and sensitive, and provides gene expression data quickly and easily, without the need for radioactive reagents.

Luciferases are one of a number of reporters, e.g., firefly luciferase, Renilla luciferase, chloramphenicol acetyl transferase (CAT), beta-galactosidase (lacZ), beta-glucuronidase (GUS) and various phosphatases, such as secreted alkaline phosphatase (SEAP) and uteroferrin (Uf; an acid phosphatase), that have been combined and used as co-reporters of genetic activity. A dual enzyme reporter system relates to the use, expression, and measurement of two individual reporter enzymes within a single system. In genetic reporting, dual reporter assays are particularly useful for assays in individual cells or cell populations (such as cells dispersed in culture, segregated tissues, or whole animals) genetically manipulated to simultaneously express two different reporter genes. Most frequently, the activity of one gene reports the impact of the specific experimental conditions, while the activity of the second reporter gene provides an internal control by which all sets of experimental values can be normalized. Dual enzyme reporter technology can also be employed with cell-free reconstituted systems such as cellular lysates derived for the simultaneous translation, or coupled transcription and translation, of independent genetic materials encoding experimental and control reporter enzymes. Immunoassays may, likewise, be designed for dual reporting of both experimental and control values from within a single sample.

The performance of any dual enzyme reporter assay is based on the characteristics of the constituent enzyme chemistries and the ability to correlate their respective resulting data sets. Disparate enzyme kinetics, assay chemistries and incubation requirements of various reporter enzymes can complicate combining two reporter enzymes into an integrated, single tube or well dual reporter assay format. One approach to integration of a dual reporter assay is described in U.S. Pat. No. 5,744,320, which discloses particular general or specific quenching agents for beetle and Renilla luciferase assays and demonstrates an exemplary dual reporter assay for sequentially determining luminescence from firefly luciferase then Renilla luciferase. Similarly, U.S. Pat. No. 6,586,196 discloses several dual reporter assay systems. Like the dual reporter systems disclosed in the '320 patent, luminescence is the measurable product of each of two reactions in the '196 patent. Approaches to multiplexing of reporter assays which incorporate not only different substrates but also different detection technologies are described in Liu et al. (2000) and Qazi et al. (2002). For instance, Liu et al. report luciferase and GFP activity in the same organism, where enzyme activity is determined via luminescence and fluorescence detection, respectively, in a stepwise fashion.

Reporters are also useful to detect the presence or activity of molecules within cells or supernatants. For instance, proteases constitute a large and important group of enzymes involved in diverse physiological processes such as protein turnover in blood coagulation, inflammation, reproduction, fibrinolysis, and the immune response. Numerous disease states are caused by, and can be characterized by, the alterations in the activity of specific proteases and their inhibitors. The ability to measure these proteases in research or in a clinical setting is significant to the investigation, treatment and management of disease states. For example, caspase-3 and caspase-7 are members of the cysteine aspartyl-specific protease (also known as the aspartate specific-cysteine protease, "ASCP") family and play key effector roles in cell death in mammalian cells (Thornberry et al., 1992; Nicholson et al., 1995; Tewari et al., 1995; and Fernandes-Alnemri et al., 1996).

Proteases, however, are not easy to assay with their naturally occurring substrates. Moreover, many currently available synthetic substrates are expensive, insensitive, and non-selective.

Numerous chromogenic and fluorogenic substrates have been used to measure proteases (Monsees et al., 1994; Monsees et al., 1995) and modified luciferins have provided alternatives to fluorescent indicators (U.S. Pat. Nos. 5,035,999 and 5,098,828). Methods for using modified luciferins with a recognition site for a hydrolase as a pro-substrate were first described by Miska and Geiger (1989), where heterogeneous assays were conducted by incubating a modified luciferin with a hydrolase for a specified period of time, then transferring an aliquot of the mixture to a solution containing luciferase. Masuda-Nishimura et al. (2000) reported the use of a single tube (homogeneous) assay which employed a β-galactosidase substrate-modified luciferin.

Fluorescent or luminescent substrates or products of enzyme reactions have been employed in protein assay multiplexing. For example, fluorescent beads having ligands for up to 15 different cytokines were employed to detect two or more different cytokines (DeJager et al., 2003) and fluorescein diphosphate and casein BODIPY-FL were employed to detect alkaline phosphatase and certain proteases (Nolkrantz et al., 2002).

However, what is needed is an improved assay, e.g., a homogeneous assay, to detect two or more proteins using different detection techniques.

SUMMARY OF THE INVENTION

The invention provides multiplexing of nonluminogenic, e.g., fluorescent or colorimetric, and luminogenic assays, e.g., in the same well, to detect the amount (e.g., activity) or presence in a sample of one or more moieties, including cofactors for enzymatic reactions such as ATP, proteins (peptides or polypeptides) that bind to and/or alter the conformation of a molecule, e.g., proteins that modify or cleave a peptide or polypeptide substrate, or a molecule which is bound by and/or altered by a protein. As used herein, a "luminogenic assay" includes a reaction in which a first molecule, e.g., a peptide or polypeptide substrate for a first enzyme, the product of a reaction between the first molecule and an appropriate (first) protein, and/or a product of a reaction between a different protein and the product of the first reaction, is luminogenic. Thus, a luminogenic assay may directly or indirectly detect, e.g., measure, the amount or presence of a cofactor for a reaction, a molecule which is bound by and/or altered by a protein, or the protein. For instance, in one embodiment, a beetle luciferase and an appropriate luciferin substrate may be employed in a luminogenic assay to detect ATP concentration, while in another embodiment a substrate for a luciferase, which is modified to contain a protease recognition site (modified, for example, via a covalent bond), may be employed in a luminogenic assay to detect the protease, i.e., when luciferase is present. Luminogenic assays include chemiluminescent and bioluminescent assays including but not limited to those which employ or detect luciferase, β-galactosidase, β-glucuronidase, β-lactamase, a protease, alkaline phosphatase, or peroxidase, and suitable corresponding substrates, e.g., modified forms of luciferin, coelenterazine, luminol, peptides or polypeptides, dioxetanes, dioxetanones, and related acridinium esters. As used herein, a "luminogenic assay reagent" includes a substrate, as well as a cofactor(s) or other molecule(s) such as a protein, e.g., an enzyme, for a luminogenic reaction. In one embodiment, the luminogenic assay reagent may be Z-DEVD-aminoluciferin (DEVD corresponds to SEQ ID NO:1), Z-LETD-aminoluciferin (LETD corresponds to SEQ ID NO:14), Z-LEHD-aminoluciferin (LEHD corresponds to SEQ ID NO:3), or may be other substrates, e.g., peptide or polypeptide substrates, linked to aminoluciferin, dihydroluciferin, luciferin 6' methylether, or luciferin 6' chloroethylether. A luminogenic assay is one in which a luminogenic reaction yields at least 1%, e.g., at least 10%, more light than a corresponding nonluminogenic assay.

A "nonluminogenic assay" includes a reaction in which a first molecule, e.g., a protein (a peptide or polypeptide), a (first) product of a reaction between the first molecule and a suitable (first) protein (peptide or polypeptide), or a product of a reaction between a different protein and the first product is/are not luminogenic but may be otherwise detectable, e.g., the substrate and/or product(s) are detected using a fluorescent or colorimetric assay, which directly or indirectly measures the amount or presence of a cofactor for the reaction, the molecule or the protein which interacts with the molecule. For instance, a substrate for an enzyme may be modified to contain a fluorophore that emits light of a certain wavelength only after the enzyme reacts with the substrate and the fluorophore is contacted with (exposed to) light of a certain wavelength or range of wavelengths, e.g., (Z-DEVD)$_2$-rhodamine-110 (DEVD corresponds to SEQ ID NO:1) is a substrate for a caspase, and cleavage of that substrate by the caspase may be monitored via fluorescence of rhodamine-110. As used herein, a "fluorogenic assay reagent" includes a substrate, as well as a cofactor(s) or other molecule(s), e.g., a protein, for a fluorogenic reaction. A nonluminogenic assay is one in which a nonluminogenic reaction yields less than about 10%, e.g., less than about 1% or less, the luminescent signal of a corresponding luminogenic assay.

In one embodiment, molecules employed in the assays of the invention, e.g., those which bind and/or are altered by a protein, include ones that are modified to contain a reporter molecule, i.e., a molecule which is detectable or capable of detection, e.g., after one or more subsequent reactions. For example, in one embodiment, a substrate employed in a luminogenic assay of the invention includes a substrate for an enzyme to be detected, which substrate is covalently linked to a substrate for a luminogenic reaction, while in another embodiment a substrate employed in a fluorogenic assay may include a substrate for an enzyme to be detected, which substrate is covalently linked to one or more fluorophores. In some embodiments, the molecule which is bound by and/or altered by a protein does not contain a reporter molecule.

As described herein, the amount or presence of more than one protease in a sample was detected using at least two different substrates, one which had a luminescent readout and one or more of which had a fluorescent readout. For example, detection of a low abundance cellular protease was achieved using a more sensitive luminescent approach, e.g., detection of caspase-8 with the substrate Z-LETD-aminoluciferin (LETD corresponds to SEQ ID NO:14), followed by a detection of another protease using another substrate, for instance, caspase-3 with (Z-DEVD)$_2$-rhodamine-110 (DEVD corresponds to SEQ ID NO:1). This assay thus combines the strengths of both a fluorogenic reagent and the sensitivity of a luciferase-mediated luminescent reaction. Moreover, surprisingly, the presence of a luciferin, a molecule which has fluorescent properties and is often present in relatively large quantities in luminescent assays, did not result in significant interference in combined fluorescent/luminescent assays. Further, surprisingly, two caspases and a luciferase were detected in the same reaction mix, a mix which included a caspase-8 substrate (Z-LETD-aminoluciferin (LETD corresponds to SEQ ID NO:14)) and two caspase-3 substrates, i.e., (Z-DEVD)$_2$-rhodamine-110 (DEVD corresponds to SEQ ID NO:1) and Ac-DEVD-AMC (DEVD corresponds to SEQ ID NO:1). The present invention thus provides more flexibility in molecules to be employed in multiplex assays, e.g., substrates for a luminogenic assay in combination with substrates for a fluorogenic assay. Moreover, if two enzyme-mediated reactions have compatible reagent conditions, the assay can be a one-step assay.

Accordingly, a combined luminogenic/nonluminogenic assay format of the present invention allows multiplexing of assays for one or more peptides or polypeptides, e.g., enzymes, one or more molecules which are bound by and/or altered by the peptide(s) or polypeptide(s), e.g., a peptide or polypeptide substrate for each enzyme, and/or one or more cofactors for each assay, or a combination thereof. Thus, in one embodiment, the invention provides a method to detect the presence or amount of a first molecule for a first enzyme-mediated reaction and the presence or amount of a second molecule for a second enzyme-mediated reaction. The method includes contacting a sample suspected of having the first and/or second molecules with a reaction mixture for the first and second enzyme-mediated reactions which lacks the first and/or second molecules. The presence or amount of the first and the second molecules is then detected. The use of multiplexing which includes a luminescent assay provides increased sensitivity for the molecule detected using the luminescent assay. In one embodiment, a reaction mediated by the first enzyme yields a luminogenic product, whereas a reaction mediated by the second enzyme yields a nonluminogenic product. In one embodiment, a combined luminogenic/fluorogenic assay is provided including one in which one of the assays provides an internal control. The assays described herein may be employed with other assays, including reporter assays, nucleic-acid based assays or immunological-based assays and other unrelated enzyme assays.

The invention also provides a method for measuring the activity or presence of at least one molecule in a sample. The method includes providing a sample that may contain at least one molecule for an enzyme-mediated reaction, e.g., the sample may contain the enzyme, and contacting the sample with a reaction mixture for the enzyme-mediated reaction which lacks the molecule, e.g., the reaction mixture contains a substrate for the enzyme, so as to yield a reaction mixture wherein the presence or amount of the molecule is capable of being detected by a luminogenic assay. In one embodiment, the sample and/or reaction mixture is also contacted with reagents to detect a molecule for a second enzyme-mediated reaction, where the presence or amount of the molecule for the second enzyme-mediated reaction is capable of being detected by a nonluminogenic assay.

In one embodiment, the invention provides a method to detect the presence or amount of a first enzyme and/or a cofactor for a reaction mediated by that enzyme in a sample. The method includes contacting the sample with a first substrate for the first enzyme, a second substrate for a second enzyme, and optionally a third enzyme, to yield a reaction mixture. In one embodiment, at least the first and second enzymes are not the same, e.g., do not substantially recognize the same substrate, i.e., they do not bind to the same substrate, or if they bind to and react with the same substrate, one of the enzymes does not react with a substrate for the other enzyme to the same extent (efficiency), i.e., one of the enzymes does not react substantially with a substrate for the other enzyme when substrates for both enzymes are present. As used herein, an enzyme (first enzyme) which does not react substantially with a substrate for a second enzyme includes an enzyme which, in a reaction having the second enzyme and equal amounts of a substrate for the first enzyme and a substrate for the second enzyme, cross reacts with the substrate for the second enzyme no more than 25%, e.g., cross reacts 15%, 10% or 5% or less, relative to a reaction between the first enzyme and substrate for the first enzyme. The first substrate, a product of a reaction between the first substrate and the first enzyme, and/or a product of a reaction between the third enzyme and the product of the first enzyme and the first substrate, is/are luminogenic. The second substrate, a (second) product of a reaction between the second substrate and the second enzyme, and/or a product of a reaction between another enzyme and the second product, is/are not luminogenic but otherwise detectable. The presence or amount of the first enzyme and/or cofactor is detected or determined. In one embodiment, the presence or amount of the second enzyme and/or a cofactor for the reaction mediated by the second enzyme is also detected or determined. In one embodiment, at least the first and second enzymes are not the same. The enzymes to be detected may be native enzymes or recombinant enzymes, e.g., including fusion proteins. The optional enzyme(s) added to the sample likewise may be native or recombinant enzymes.

In another embodiment, the invention provides a method to detect the presence or amount of a first enzyme and/or a cofactor for a reaction mediated by that enzyme in a sample. The method includes contacting the sample with a first substrate for the first enzyme, a second substrate for a second enzyme, and optionally a third enzyme, to yield a reaction mixture, wherein optionally at least the first and second enzymes are not the same. The first substrate, a product of a reaction between the first substrate and the first enzyme, and/or a product of a reaction between the third enzyme and the product of the first enzyme and the first substrate, is/are not luminogenic but otherwise detectable. The second substrate, a second product of a reaction between the second substrate and the second enzyme, and/or a product of a reaction between another enzyme and the second product, is/are luminogenic. The presence or amount of the first enzyme and/or cofactor is detected or determined. In one embodiment, the presence or amount of the second enzyme is also detected or determined. The enzymes to be detected or employed in the reaction mixture may be native enzymes or recombinant enzymes.

Further provided is a method of assaying an enzyme-mediated luminescence reaction to detect a first enzyme or cofactor for a reaction mediated by that enzyme. The method includes contacting a sample with a first substrate for the first enzyme, a second substrate for a second enzyme, and optionally a third enzyme, to yield a reaction mixture, wherein the first and second enzymes are not the same. The first substrate, a product of the reaction between the first substrate and the first enzyme, and/or a product of the third enzyme and the product of the first enzyme and first substrate, is/are luminogenic. The second substrate, a second product of the reaction between the second substrate and the second enzyme, and/or a product of a reaction between the second product and another enzyme is/are not luminogenic but otherwise detectable. Luminescence is then detected. The method may further include detecting the presence or amount of the second enzyme, e.g., by detecting the presence or amount of the nonluminogenic substrate or product(s). In one embodiment, the second enzyme does not bind to or react with the first substrate, while in another embodiment, the first enzyme does not bind to or react with the second substrate. In one embodiment, at least the first and second enzymes are not the same. The enzymes to be detected or employed in the reaction mixture may be native enzymes or recombinant enzymes.

Also provided is a method of assaying an enzyme-mediated luminescence reaction to detect a first enzyme or cofactor for a reaction mediated by that enzyme. The method includes contacting a sample with a first substrate for the first enzyme, a second substrate for a second enzyme, and a third enzyme, to yield a reaction mixture. The first substrate, a product of the reaction between the first substrate and the first enzyme, and/or a product of the third enzyme and the product of the first enzyme and first substrate, is/are not luminogenic but otherwise detectable. The second substrate, a second product of the reaction between the second substrate and the second enzyme, and/or a product of a reaction between the second product and another enzyme is/are luminogenic. Luminescence is then detected. The method may further include detecting the presence or amount of the first enzyme or product of the first enzyme and first substrate. In one embodiment, the second enzyme does not bind to or react substantially with the first substrate, while in another embodiment, the first enzyme does not bind to or react substantially with the second substrate. In one embodiment, at least the first and second enzymes are not the same. The enzymes to be detected or employed in the reaction mixture may be native enzymes or recombinant enzymes, e.g., including fusion proteins.

Further provided is a method to detect the presence or amount of at least two molecules in a sample. The method includes contacting a sample with a first substrate for a first enzyme, a second substrate for a second enzyme, and optionally a third enzyme, to yield a reaction mixture, wherein at least the first and second enzymes are not the same. A reaction between the first enzyme and the first substrate or the third enzyme and a product of the reaction between the first substrate and the first enzyme yields a luminogenic product. The second substrate, a second product of the reaction between the second substrate and the second enzyme, and/or a product of a reaction between the second product and a different enzyme, is/are not luminogenic. The presence or amount of the first and second enzymes and/or cofactor(s) is then detected. In one embodiment, luminescence is employed to detect the first enzyme and/or cofactor and fluorescence or colorimetry is employed to detect at least one other enzyme and/or cofactor. In one embodiment, substrates for two different enzymes are simultaneously combined with a sample to yield a reaction mixture. A reaction between one of the substrates and one of the enzymes directly or indirectly generates a luminescent signal while a reaction between the other substrate and enzyme directly or indirectly generates a fluorescent signal. Following an incubation period, the fluorescent signal is employed to detect the presence or amount of one enzyme and/or cofactor and the luminescent signal is employed to detect the presence or amount of the other enzyme and/or cofactor. Specific buffer conditions can vary with the enzymes and/or cofactor(s) being detected, and can be determined by one of skill in the art of in vitro assays, e.g., enzyme assays. Alternatively, the assay can be a two-step assay, with reagent adjustment between the first and second assays. For example, reagent adjustment can include addition of a quenching agent for the first reaction, and/or an enhancing agent for the second reaction.

In one embodiment, to detect the first enzyme or cofactor for the first enzyme-mediated reaction and the second enzyme or cofactor for the second enzyme-mediated reaction, the sample is simultaneously contacted with the first substrate and the second substrate. In another embodiment, the sample is contacted with the second substrate before the first substrate, or is contacted with the first substrate before the second substrate. In one embodiment, the third or different enzyme may be added with the one or more substrates, before the one or more substrates or after the one or more substrates.

In one embodiment, to detect the first substrate or cofactor for the first enzyme-mediated reaction and the second substrate or cofactor for the second enzyme-mediated reaction, the sample is simultaneously contacted with the first enzyme and the second enzyme. In another embodiment, the sample is contacted with the second enzyme before the first enzyme, or is contacted with the first enzyme before the second enzyme.

In one embodiment, to detect the first enzyme or cofactor for the first enzyme-mediated reaction and the second substrate or cofactor for the second enzyme-mediated reaction, the sample is simultaneously contacted with the first substrate and the second enzyme. In another embodiment, the sample is contacted with the second enzyme before the first substrate, or is contacted with the first substrate before the second enzyme. In one embodiment, to detect the first substrate or cofactor for the first enzyme-mediated reaction and the second enzyme or cofactor for the second enzyme-mediated reaction, the sample is simultaneously contacted with the first enzyme and the second substrate. In another embodiment, the sample is contacted with the second substrate before the first enzyme, or is contacted with the first enzyme before the second substrate.

The sample employed in the methods of the invention may be a cell lysate, an in vitro transcription/translation reaction, a supernatant of a cell culture, a physiological fluid sample, e.g., a blood, plasma, serum, cerebrospinal fluid, tears or urine sample, and may include intact cells. The cells, cell lysate, or supernatant may be obtained from prokaryotic cells or eukaryotic cells.

The invention also provides for simultaneous or sequential detection of the presence or amount of the first and second proteins, e.g., enzymes, or a cofactor(s) for a reaction mediated by at least one of those proteins, e.g., for concurrent reactions or for sequential reactions optionally without quenching one of the reactions or enhancing/accelerating one of the reactions. In one embodiment, first and second substrates are added to the sample simultaneously and the amount or presence of the first enzyme and/or cofactor is detected before the amount or presence of the second enzyme and/or cofactor is detected. In another embodiment, the first and second substrates are added to the sample simultaneously and the presence or amount of the second enzyme and/or cofactor is detected before the amount or presence of the first enzyme and/or cofactor is detected. Alternatively, the first and second substrates are added to the sample simultaneously and the presence or amount of the first and second enzymes and/or cofactors is detected simultaneously. Preferably, the presence or amount of enzymes and/or cofactors are detected in a single reaction, e.g., all reactions are conducted in a single receptacle, e.g., well.

In another embodiment, the invention provides a method to detect the presence or amount of a molecule for an enzyme-mediated reaction in conjunction with expression of a fluorescent protein, e.g., green fluorescent protein. For example, cells which transiently or stably express a fluorescent protein, or a protein that can be labeled in cells to become fluorescent, such as dehalogenase, can be assayed for the presence or amount of the fluorescent protein via a fluorogenic assay as well as assayed for at least one additional molecule, e.g., an enzyme, substrate or co-factor for a reaction mediated by the enzyme, which molecule is present in or secreted by the cells via a luminogenic assay. In one embodiment, the presence or amount of a different molecule is also detected or determined, for example, in a nonluminogenic assay. The presence or amount of the molecule(s) may then be normalized using data generated from the fluorescent protein.

Thus, the invention provides a method to detect the presence or amount of a molecule for a reaction mediated by a first enzyme. The method includes contacting a sample which comprises cells which express a fluorescent protein with a reaction mixture for the first enzyme which lacks the molecule, and optionally a second enzyme. A reaction mediated by the first enzyme yields a luminogenic product. The presence or amount of the molecule and the presence or amount of the fluorescent protein are then detected.

In one embodiment, for luminogenic and/or fluorogenic assays which yield products with different characteristics, e.g., different colors, further multiplexing (i.e., with other substrates) may be employed. For example, further multiplexing may include using different colors emitted by different luciferase based reactions or substrates or a fluorogenic assay with different excitation/emission spectra.

The invention also provides a method for determining the presence or number of live and/or dead cells in a population of cells, e.g., a cell culture population. The method is based on differential proteolytic activities associated with cell membrane permeability and integrity. Advantages of the method include sensitivity, simplicity, flexibility of assay readout for downstream multiplexed applications and population response normalization. Differential measurement of viability is predicated upon the relative impermeability of one protease substrate and on poor enzyme activity against another protease substrate from a protease released from the cell environment. Substrates useful in this embodiment include substrates for exo- or endo-proteases, including substrates that are blocked at the N- or C-terminus. In one embodiment, at least two different fluorogenic substrates (fluorogenic assay reagents) are employed, one of which is substantially cell impermeant and specific for a protease that is active in an extracellular environment, e.g., a ubiquitous, conserved, released protease. The other substrate is substantially cell permeable and specific for an intracellular protease that is active in a viable cell but substantially inactive when present in an extracellular environment. Substantially cell impermeant protease substrates are those which are not detectable in viable cells during a period of time generally employed to measure an endpoint in an assay for dead cells, e.g., at times less than 5, 4, 3, 2 or 1.5 hours, after addition of the protease substrate to a sample. Substantially cell permeant protease substrates are those which enter viable cells during a period of time generally employed to measure an endpoint in an assay for live cells, e.g., at times greater than 5, 15, 30, 60, or 120 minutes or more, after substrate addition to a sample. A protease which is substantially inactive under some conditions is one having less than about 10% the optimal activity of that protease. In one embodiment, the substantially cell impermeant fluorogenic substrate includes a tri- or tetra-peptide substrate. In one embodiment, the substantially cell permeable fluorogenic substrate includes an amino acid, or a di-or tri-peptide substrate. The sample is contacted with the two substrates, which sample is optionally treated with one or more test conditions or agents in an amount not intended to result in cell lysis or produce a cell lysate (generally "nondestructive"). The fluorophores in the two fluorogenic substrates have different spectra, and the relative fluorescent light units (RFLU) obtained from a sample contacted with the fluorogenic substrates allows for the determination of live and dead cells in the sample.

In another embodiment, a fluorogenic protease substrate and a luminogenic protease substrate are employed to detect or determine the presence or amount of live and dead cells in a sample. One substrate is substantially cell impermeant and specific for a protease that is active in an extracellular environment, and the other substrate is substantially cell permeable and specific for an intracellular protease that is active in a viable cell but substantially inactive when present in an extracellular environment. In one embodiment, the substantially cell impermeant protease substrate includes a tri- or tetra-peptide substrate. In one embodiment, the substantially cell permeable protease substrate includes an amino acid, or a di-or tri-peptide substrate. The sample is contacted with the two substrates, e.g., in the absence of conditions that result in cell lysis, and detection of the fluorogenic and luminogenic products resulting from protease cleavage (RFLU and RLU) allows for the determination of live and dead cells in the sample. For instance, a luciferase detection reagent that does not cause cell lysis may be added to wells contacted with a luminogenic substrate.

The spectrally distinct signals of released and retained protease activity can be measured, e.g., using a fluorometer or fluorometer/luminometer instrument. Such measures are inversely proportional, and as such, complimentary. Viability and cytotoxicity assays may be used in normalizing, controlling, and improving data.

As described herein, Ala-Ala-Phe-AMC (released protease substrate) and Gly-Phe-AFC (live cell retained protease) were combined with % mixes of live cells and cell lysates. Cell viability was compromised by freeze/thaw cycling, detergent treatments as well as by agents that induce apoptosis (e.g., staurosporine, rTRAIL, and anti-Fas mAb). Furthermore, these measures of cell viability were also multiplexed to either other cell viability measures (CellTiter-Glo™, CellTiter-Blue™, or CytoTox-ONE™) or to specific measures of apoptotic cytotoxicity (Caspase-Glo™ 3/7, -8, -9 or Apo-ONE™). As also described herein, other substrates, e.g., other fluorogenic substrates such as those containing rhodamine 110 or luminogenic substrates such as aminoluciferin based substrates, may be used in protease release and/or protease retention assays.

Accordingly, the use of the live and/or dead cell assays described herein provides for inverse and complimentary measures of cell health, and can be employed to detect the effect of alterations in conditions, for instance, treatment with a compound, without the need for a lysis step. Moreover, because the substrate(s) have negligible or no intrinsic color, there is no signal quenching effect observable in the paired endpoint assay. Further, both protease release and retention activity components have practical sensitivities (detection of <2-5% difference in viability in 10,000 cells/well), which sensitivities can be achieved in as few as 15 minutes. In addition, the substrate(s) may be admixed into cell wells without dramatically altering the well volume, which increases the flexibility of next step endpoint chemistries. For instance, the use of a live/dead assay coupled with a dsDNA intercalator or other suitable endpoint, may be employed to detect or determine the % of dead cells versus control, the % of live cells versus control, the number of total cells versus control, and/or the mechanism of cell death (caspase activation) or other endpoint reporter assay determinations.

Thus, the invention provides for individual nondestructive fluorogenic or nondestructive luminogenic protease based assays, or multiplexing of nondestructive fluorogenic and/or nondestructive luminogenic protease based live/dead cell assays, or combinations of nondestructive fluorogenic protease based assays, with other assays, e.g., in the same well. In one embodiment, the proteases to be detected or determined in the live/dead cell assay are not the same, e.g., do not substantially recognize the same substrate, i.e., they do not bind to the same substrate, or if they bind to and react with the same substrate, one of the proteases does not react with a substrate for the other protease to the same extent (efficiency), i.e., one of the proteases does not react substantially with a substrate for the other protease when substrates for both proteases are present.

The invention thus provides a method to detect live and/or dead cells in a sample. The method includes contacting a sample with a substrate for a first protease and a substrate for a second protease. A reaction with one of the substrates mediated by one of the proteases yields a fluorogenic product and a reaction with the other substrate mediated by the other protease yields a luminogenic or a fluorogenic product. One of the substrates is substantially cell permeant and the other substrate is substantially cell impermeant. Fluorescence and/or luminescence in the sample is then detected and determined, which in turn detects or determines the number or presence of live and/or dead cells in the sample.

In one embodiment, substrates for two different proteases are simultaneously combined with a sample. In another embodiment, the sample is contacted with the second substrate before the first substrate, or is contacted with the first substrate before the second substrate. In one embodiment, the assay can be a two-step assay, optionally with reagent adjustment between the first and second assays. The invention also provides for simultaneous or sequential detection of the presence or amount of the first and second proteases. In one embodiment, first and second substrates are added to the sample simultaneously and the amount or presence of one protease is detected before the amount or presence of the other protease is detected. Alternatively, the first and second substrates are added to the sample simultaneously and the presence or amount of the first and second proteases is detected simultaneously. Preferably, the presence or amount of proteases are detected in a single reaction, e.g., all reactions are conducted in a single receptacle, e.g., well.

The invention provides a method to detect live cells in a sample. The method includes contacting a sample with a fluorogenic substantially cell permeable substrate for a protease associated with a proteasome, an aminopeptidase or a cathepsin, and detecting or determining fluorescence in the sample, thereby detecting or determining the number or presence of live cells in the sample.

Also provided is a method to detect dead cells in a sample. The method includes contacting a sample with a fluorogenic or luminogenic cell impermeable substrate a tripeptidyl peptidase, calpain or chymotrypsin, and detecting or determining fluorescence or luminescence in the sample, thereby detecting or determining the number or presence of dead cells in the sample.

Also provided are kits which include one or more reagents for use in the assays of the invention. In one embodiment, the invention provides kits useful for detecting live and/or dead cell in a sample. For example, the invention provides a kit which includes a composition having a first fluorogenic or luminogenic substantially cell impermeant substrate for a first protease and a second fluorogenic substantially cell permeable substrate for a second protease; and instructions for directing the user on the use of the composition to detect live and/or dead cells in a sample. In one embodiment, the composition is a solution, e.g., a solution in which the substrates are present at 0.005 to about 1.0 M, e.g., 0.05 to about 0.2 M in a solvent, e.g., an organic solvent. In another embodiment, the invention includes a kit comprising a composition comprising Ala-Ala-Phe-AMC, (Ala-Ala-Phe)$_2$-R110, Ala-Ala-Phe-aminoluciferin, Gly-Phe-AFC, Gly-Phe-AMC, Gly-Gly-Leu-AMC, or any combination thereof. In one embodiment the composition is a solution, e.g., a solution in which the substrates are present at 0.005 to about 1.0 M, e.g., 0.05 to about 0.2 M.

The assay also has use as a drug discovery tool. Many drug-testing compounds have fluorescent properties that may interfere with a fluorescent/luminescent multiplex assay. The present invention provides assays to detect false results. As described herein, the same consensus substrate sequence for caspase-3 was linked to different reporter molecules with distinct spectral readouts, e.g., two with a fluorescent readout and one with a luminescent readout. Caspase-3 and luciferase were assayed in the presence and the absence of a caspase-3 inhibitor or a luciferase inhibitor. The data showed that there was very little interference between the three reporter molecules, and that luciferase could be used in a normalizing assay to control for false results.

Thus, the presence or amount of a modulator, for instance, an inhibitor, of an enzyme may be detected using a multiplex assay of the invention, e.g., a combined fluorogenic/luminogenic assay. In one embodiment, the method includes providing a reaction mixture comprising a nonluminogenic substrate for a first enzyme, a second substrate for the first enzyme, a second enzyme for a luminogenic assay, and a test agent. A reaction between the nonluminogenic substrate and the first enzyme but not the second substrate and the first enzyme yields a nonluminogenic product, and a reaction between the second substrate and the first enzyme yields a substrate for the second enzyme, e.g., a substrate for a luciferase. A reaction between the substrate for the second enzyme and the second enzyme yields a luminogenic product. The presence or amount of the luminogenic product and the nonluminogenic product is compared in test and control reactions. Comparison of the two results indicates the effect of the modulator on the enzyme for the luminogenic assay, which can eliminate false results.

BRIEF DESCRIPTION OF THE DRAWINGS

FIG. 1A-B. Multiplex assay measuring the enzyme activities of caspase-3 and caspase-8 in the presence of both luminogenic and fluorogenic assay reagents. A) Relative light units (RLU) versus time (SEQ ID NO:1). B) Relative fluorescence units (RFU) over time (SEQ ID NOs:1 and 14).

FIGS. 2A-C. Multiplex assay of caspase-3 and caspase-8. A) Signal to background fluorescence for AMC. B) Signal to background fluorescence for rhodamine-110. C) Signal to background luminescence.

FIGS. 3A-C. Triplex assay measuring the activities of caspase-3, caspase-8, and trypsin. A) RFU for rhodamine-110; B) RFU for AMC; C) RLU.

FIGS. 4A-D. Multiplex assay measuring a protease (caspase-3) and a non-protease (β-galactosidase) enzyme. A) and C), RLU at ½ hour and 18 hours, respectively (SEQ ID NO:1). B) and D) RFU at 2 hours and 18 hours, respectively (SEQ ID NO:1).

FIG. 6. Signal to background ratios in three channels; rhodamine-110, AMC and luminescence, in a caspase-3 assay (SEQ ID NO:1).

FIGS. 7A-D. Multiplex fluorogenic and luminogenic assays measuring lactate dehydrogenase (LDH) activity and adenosine triphosphate (ATP). A) and C) RLU versus ATP concentration. B) and D) RFU versus LDH dilution.

FIG. 19A. Plot of RFLU versus number of Jurkat cells treated with three different protease retention assay reagents.

FIG. 24B. Protease based live/dead assay with Hep2G cells treated with ionomycin and stained with PicoGreen™.

DETAILED DESCRIPTION OF THE INVENTION

Figure 1B:
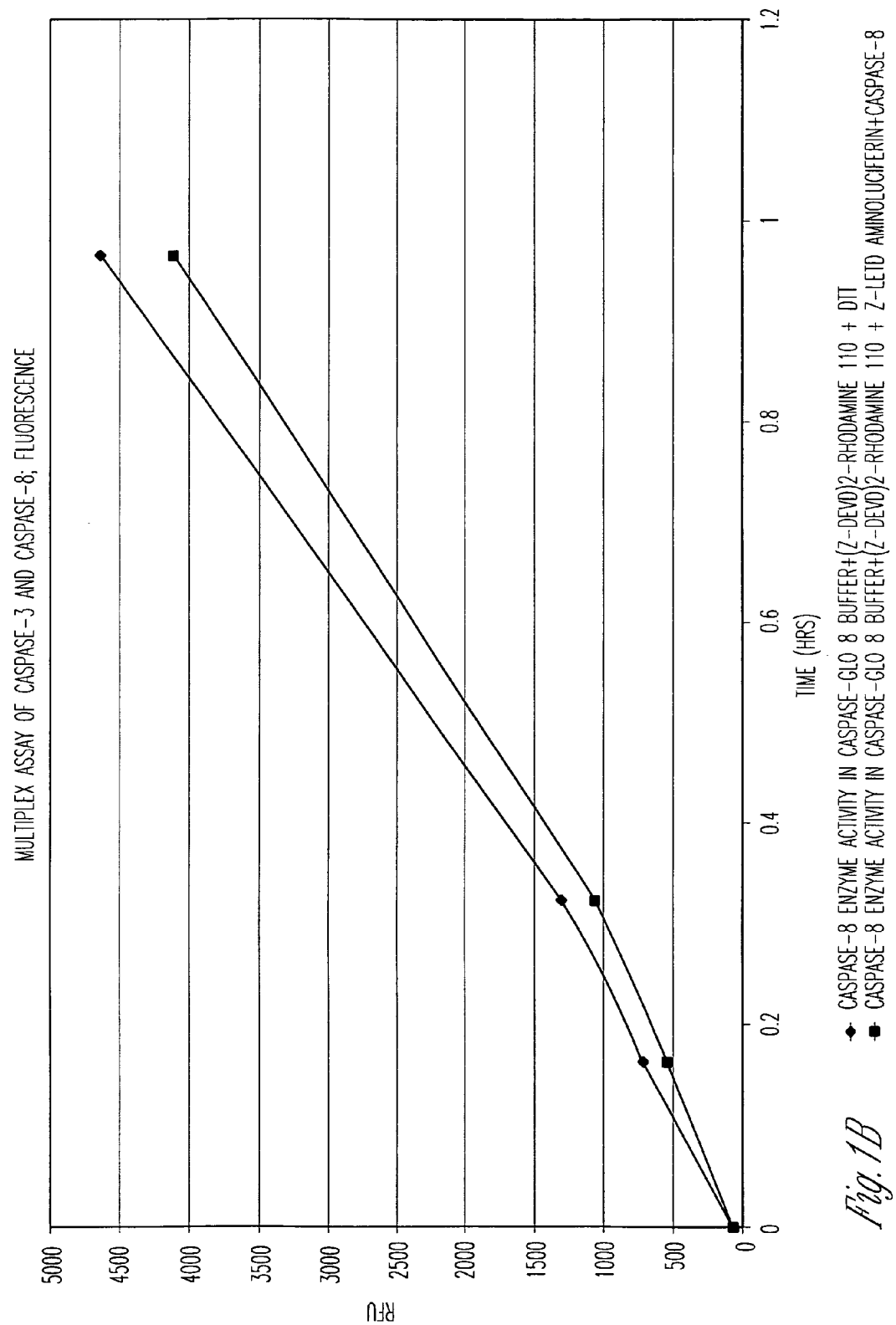

The invention provides a multiplexed assay method in which at least two different molecules which bind to and/or are altered by a protein (e.g., peptide or polypeptide) are provided either simultaneously or sequentially in a reaction mixture to detect one or more moieties including proteins (peptides or polypeptides), e.g., enzymes, or substrates or cofactors for reactions. For instance, one or more enzyme-mediated reactions are performed under conditions effective to convert at least one enzyme substrate to a product of a reaction between the substrate and the enzyme. Preferably, each molecule in the reaction mixture, e.g., substrate, or product in the reaction has a different characteristic from other molecule(s) or product(s), and, in one embodiment, at least one molecule includes a reporter molecule capable of directly or indirectly producing a detectable signal. The resulting signal is related to the presence or amount of the molecule to be detected. In one embodiment, the method includes performing two or more enzyme reactions in the presence of at least two different enzyme substrates under conditions effective to convert each substrate to a corresponding product, where at least the substrate or product of each reaction, and/or a product of a reaction between one of the products and a third, e.g., different, enzyme, has a different detectable characteristic, e.g., a different optical characteristic, from the other substrate(s) and/or product(s). After performing the reactions, either simultaneously or sequentially, the presence or amount of one or more substrates or one or more products of the reaction(s) is/are detected or determined. From this, the presence or amount of the corresponding enzyme(s) and/or cofactors can be determined.

Thus, two general types of multiplexed assays are contemplated. In the first, multiple moieties, e.g., one or more enzymes, one or more substrates and/or one or more cofactors for an enzyme-mediated reaction, are assayed in the same reaction mixture. Each enzyme is capable of converting at least one of the substrates to a corresponding product, where the substrate(s) and/or corresponding product(s), or product(s) of a reaction between one of the corresponding products and another enzyme, have different detectable characteristics that allow the substrates and/or the products to be individually detected when present in the same reaction mixture. The order of adding the molecules for the assays of the present invention can vary. Thus, individual reactions may be initiated and/or conducted simultaneously or sequentially. If initiated and conducted sequentially, the different detectable characteristics may require different detection methods, and/or adjustments to reaction conditions, e.g., reagent concentration, temperatures or additional reagents, may be performed. For instance, a quenching agent or enhancing agent may be added between reactions (see, e.g., U.S. Pat. Nos. 5,774,320 and 6,586,196, the disclosures of which are specifically incorporated by reference herein). In one preferred embodiment, the two or more reactions are carried out simultaneously in a single reaction mixture, where each of the enzymes is effective to convert one of the substrates in the reaction mixture to a product. This embodiment may be used, for example, to determine the presence or amount of at least two different enzymes and/or cofactors in a cell, cell lysate or cell supernatant. In addition, the reaction may contain one or more test agents, e.g., enzyme inhibitors or activators, and/or different concentrations of inhibitors, activators, or substrates.

Optionally, the assays are employed as a homogeneous assay, e.g., the one or more substrates and additional components are mixed prior to adding the mixture to the sample. Results may be read without additional transfer of reagents.

In a second assay type, two or more enzyme-mediated reactions are carried out in tandem. The separate reactions may be performed at the same time or at different times. The reactions may contain one or more of the same or different enzymes, one or more of the same or different test agents, e.g., enzyme inhibitors or activators, and/or different concentrations of inhibitors, activators, or substrates. In one embodiment, each reaction mixture contains at least two substrates capable of being converted to a product, where the substrate(s) and/or corresponding product(s), and/or a product(s) of a reaction between the product of one of the enzyme/substrate pairs and a different enzyme, have different detectable characteristics.

The assays of the present invention thus allow the detection of multiple enzymes or cofactors in a sample, e.g., a sample which includes eukaryotic cells, e.g., yeast, avian, plant, insect or mammalian cells, including but not limited to human, simian, murine, canine, bovine, equine, feline, ovine, caprine or swine cells, or prokaryotic cells, or cells from two or more different organisms, or cell lysates or supernatants thereof. The cells may not have been genetically modified via recombinant techniques (nonrecombinant cells), or may be recombinant cells which are transiently transfected with recombinant DNA and/or the genome of which is stably augmented with a recombinant DNA, or which genome has been modified to disrupt a gene, e.g., disrupt a promoter, intron or open reading frame, or replace one DNA fragment with another. The recombinant DNA or replacement DNA fragment may encode a molecule to be detected by the methods of the invention, a moiety which alters the level or activity of the molecule to be detected, and/or a gene product unrelated to the molecule or moiety that alters the level or activity of the molecule.

In one embodiment, the methods according to the present invention provide a rapid, highly sensitive method for simultaneously or sequentially detecting multiple moieties including enzymes in a single sample such as an aliquot of cells or a lysate thereof. In one embodiment, the method includes quantifying the presence or amount (activity) of a first enzyme, substrate or cofactor in a luminogenic assay and quantifying the presence or amount of a second enzyme, substrate or cofactor in a nonluminogenic assay, such as a fluorogenic assay. In one embodiment, reagents, e.g., substrates, for each reaction may be added together or sequentially. In another embodiment, the method includes quantifying the presence or amount of a first enzyme, substrate or cofactor in a fluorogenic assay and quantifying the presence or amount of a second enzyme, substrate or cofactor in a luminogenic assay. Thus, in another embodiment, the method includes quantifying the presence or amount of a cofactor in a luminogenic assay and quantifying a different molecule in a nonluminogenic assay. In yet another embodiment, the method includes quantifying the presence or amount of a cofactor in a nonluminogenic assay and quantifying a different molecule in a luminogenic assay. The intensity of the luminogenic or nonluminogenic signal is a function of the presence or amount of the respective molecule.

The invention further provides individual and multiplexed assay methods in which one or more substrates for one or more exo- and/or endo-proteases are provided to a sample, such as one not subjected to cell lysis, which substrates are useful to detect or determine the number or presence of live and/or dead cells in the sample.

In one embodiment, the present invention relates to a method of measuring the presence or amount of one or more enzymes in a single aliquot of cells or a lysate thereof. In one embodiment, at least one of the enzymes is an endogenous enzyme, For example, in one embodiment, the present invention provides an improved, sensitive method for monitoring the activity of at least one protease and optionally another enzyme in preparations comprising the protease and the other enzyme, including purified preparations from either prokaryotic or eukaryotic cells, cell lysates or supernatants of cells such as cultured eukaryotic cells, e.g., mammalian cells. For enzymes present in different cellular locations, such as a secreted and an intracellular protease, a substrate for each enzyme can be added to a well with intact cells. The presence or amount of the secreted protease may be detected prior to detection of the intracellular protease, such as after cell lysis, e.g., where the detection of the intracellular protease is in the same receptacle, for instance, same well, as that for the secreted protease. In one embodiment, a non-cell permeant substrate for an intracellular protease and a substrate for a secreted or released protease are added to a sample comprising cells and the cells are then optionally lysed. Detection of the secreted or released protease may be before cell lysis or after cell lysis. In another embodiment, a non-cell permeant substrate for an intracellular enzyme or a secreted or released protease, and a cell permanent substrate for a second intracellular enzyme are added to a sample comprising cells. The presence of the second intracellular enzyme and the secreted or released protease may be detected without lysis. In yet another embodiment, a triplex assay is performed to detect a secreted or released protease, an intracellular enzyme (by employing either a cell permeant substrate or non-cell permeant substrate) and another molecule such as DNA or ATP, or a second enzyme, e.g., an intracellular enzyme (by employing either a cell permeant substrate or a non-cell permeant substrate). In one embodiment, the secreted or released protein is detected using fluorescence, luminescence or spectrophotometry.

The present methods can be employed to detect any molecule including any enzyme or any set of enzymes. The enzymes employed in the methods, either enzymes to be detected or enzymes which are useful to detect a substrate or cofactor, can be selected from any combination of enzymes including recombinant and endogenous (native) enzymes. In one embodiment, all of the enzymes to be detected are endogenous enzymes. In another embodiment, two enzymes to be detected are endogenous enzymes and another enzyme is a recombinant enzyme. In another embodiment, one enzyme is an endogenous enzyme and another enzyme is a recombinant enzyme. Other combinations apparent to one of ordinary skill in the art can be used in the present assays and methods according to the teachings herein. The enzymes include but are not limited to proteases, phosphatases, peroxidases, sulfatases, peptidases, and glycosidases. The enzymes may be from different groups based on the nature of the catalyzed reaction, groups including but not limited to hydrolases, oxidoreductases, lyases, transferases, isomerases, ligases, or synthases, or they may be from the same group so long as at least one of the enzymes has a partially overlapping or preferably a substantially different substrate specificity relative to at least one of the other enzymes. Of particular interest are classes of enzymes that have physiological significance. These enzymes include protein kinases, peptidases, esterases, protein phosphatases, isomerases, glycosylases, synthetases, proteases, dehydrogenases, oxidases, reductases, methylases and the like. Enzymes of interest include those involved in making or hydrolyzing esters, both organic and inorganic, glycosylating, and hydrolyzing amides. In any class, there may be further subdivisions, as in the kinases, where the kinase may be specific for phosphorylation of serine, threonine and/or tyrosine residues in peptides and proteins. Thus, the enzymes may be, for example, kinases from different functional groups of kinases, including cyclic nucleotide-regulated protein kinases, protein kinase C, kinases regulated by $Ca^{2+}$/CaM, cyclin-dependent kinases, ERK/MAP kinases, and protein-tyrosine kinases. The kinase may be a protein kinase enzyme in a signaling pathway, effective to phosphorylate an oligopeptide substrate, such as ERK kinase, S6 kinase, IR kinase, P38 kinase, and Abl kinase. For these, the substrates can include an oligopeptide substrate. Other kinases of interest may include, for example, Src kinase, JNK, MAP kinase, cyclin-dependent kinases, P53 kinases, platelet-derived growth factor receptor, epidermal growth factor receptor, and MEK.

In particular, enzymes that are useful in the present invention include any protein that exhibits enzymatic activity, e.g., lipases, phospholipases, sulphatases, ureases, peptidases, proteases and esterases, including acid phosphatases, glucosidases, glucuronidases, galactosidases, carboxylesterases, and luciferases. In one embodiment, one of the enzymes is a hydrolytic enzyme. In another embodiment, at least two of the enzymes are hydrolytic enzymes. Examples of hydrolytic enzymes include alkaline and acid phosphatases, esterases, decarboxylases, phospholipase D, P-xylosidase, β-D-fucosidase, thioglucosidase, β-D-galactosidase, α-D-galactosidase, α-D-glucosidase, β-D-glucosidase, β-glucuronidase, α-D-mannosidase, β-mannosidase, β-D-fructofuranosidase, and β-D-glucosiduronase.

A substrate or cofactor for any particular enzyme-mediated reaction is known to those of skill in the art. Exemplary cleavage sites for some proteases are set forth in Table 1.

TABLE 1

| Protease | Cut Site(s) |
|---|---|
| Aminopeptidase M | Hydrolysis from free N-terminus |
| Carboxypeptidase Y | Hydrolysis from C-terminus |
| Caspase-1,4,5 | W/LEHD-X (SEQ ID NO: 19) |
| Caspase-2,3,7 | DEXD-X (SEQ ID NO: 20) |
| Caspase-6,8,9 | L/VEXD-X (SEQ ID NO: 21) |
| Chymotrypsin | Y-X, F-X, T-X, (L-X, M-X, A-X, E-X) |
| Factor Xa | IEGR-X (SEQ ID NO: 22) |
| Pepsin | F-Z, M-Z, L-Z, W-Z (where Z is a hydrophobic residue) but will cleave others |
| TEV | E(N)XYXQ-S/G (SEQ ID NO: 23) |
| Thrombin | R-X |
| Trypsin | R-X, K-X |
| Tryptase | PRNK-X (SEQ ID NO: 24) |
| β-secretase | EISEVK/NM/L-DAEFRHD (SEQ ID NO: 25), e.g., SEVNL-DAEFR (SEQ ID NO: 26) |

X is one or more amino acids

For alkaline phosphatase, it is preferable that the substrate includes a phosphate-containing dioxetane, such as 3-(2'-spiroadamantane)-4-methoxy-4-(3"-phosphoryloxy)phenyl-1,2-dioxetane, disodium salt, or disodium 3-(4-methoxyspiro[1,2-dioxetane-3,2'(5'-chloro)-tricyclo-[3.3.1.1$^{3,7}$]decan]-4-yl]phenyl phosphate, or disodium 2-chloro-5-(4-methoxyspiro{1,2-dioxetane-3,2'-($^{5'}$-chloro)-tricyclo{3.3.1.13,7]decan}-4-yl)-1-phenyl phosphate or disodium 2-chloro-5-($^{4}$-methoxyspiro{1,2-dioxetane-3,2'-tricyclo[3.3.1.13,7]decan}-4-yl)-1-phenzyl phosphate (AMPPD, CSPD, CDP-Star® and ADP-Star™, respectively).

For β-galactosidase, the substrate preferably includes a dioxetane containing galactosidase-cleavable or galactopyranoside groups. The luminescence in the assay results from the enzymatic cleavage of the sugar moiety from the dioxetane substrate. Examples of such substrates include 3-(2'-spiroadamantane)-4-methoxy-4-(3"-β-D-galactopyranosyl)phenyl-1,2-dioxetane(AMPGD), 3-(4-methoxyspiro[1,2-dioxetane-3,2'-(5'-chloro)tricyclo[3.3.1.1$^{3,7}$]-decan]-4-yl-phenyl-β-D-galactopyranoside (Galacton®), 5-chloro-3-(methoxyspiro[1,2-dioxetane-3,2'-(5'-chloro)tricyclo[3.3.1.1$^{3,7}$]decan-4-yl-phenyl-β-D-galactopyranoside (Galacton-Plus®), and 2-chloro-5-(4-methoxyspiro[1,2-dioxetane-3,2'(5'-chloro)-tricyclo-[3.3.1.1$^{3,7}$]decan]-4-yl)phenyl β-D-galactopyranoside (Galacton-Star®).

In assays for β-glucuronidase and β-glucosidase, the substrate includes a dioxetane containing β-glucuronidase-cleavable groups such as a glucuronide, e.g., sodium 3-(4-methoxyspiro{1,2-dioxetane-3,2'-(5'-chloro)-tricyclo[3.3.1.1$^{3,7}$]decan}-4-yl)phenyl-β-D-glucuronate (Glucuron™). In assays for a carboxyl esterase, the substrate includes a suitable ester group bound to the dioxetane. In assays for proteases and phospholipases, the substrate includes a suitable enzyme-cleavable group bound to the dioxetane.

Preferably, the substrates for each enzyme in the assay are different. For assays which include one dioxane containing substrate, the substrate optionally contains a substituted or unsubstituted adamantyl group, a Y group which may be substituted or unsubstituted and an enzyme cleavable group. Examples of preferred dioxetanes include those mentioned above, e.g., those referred to as Galacton®, Galacton-Plus®, CDP-Star®, Glucuron™, AMPPD, Galacton-Star®, and ADP-Star™, as well as 3-(4-methoxyspiro{1,2-dioxetane-3, 2'-(5'-chloro)-tricyclo[3.3.1.1$^{3,7}$]decan}-4-yl)phenyl-β-D-glucopyranoside (Glucon™), CSPD, disodium 3-chloro-5-(4-methoxyspiro{1,2-dioxetane-3,2'(5'-chloro)-tricyclo-[3.3.1.1$^{3,7}$]decan)-4-yl)-1-phenyl phosphate (CDP).

Preferably, a substrate for at least one enzyme to be detected is modified to contain a reporter molecule. A reporter molecule is any molecule that allows a substrate linked to that molecule, a product resulting from a reaction between the enzyme and the substrate, or a product of a reaction between that product and another enzyme, to be differentially detected, preferably quantitatively. Reporter molecules include but are not limited to optic molecules such as fluorophores, an absorptive colored particle or a dye, radiolabels, enzymes such as a catalytic moiety that is effective to catalyze a detectable reaction in the presence of suitable reaction components, a subunit or fragment of an enzyme that is functional when associated with other subunit(s) or fragment(s), or a substrate for a subsequent reaction, e.g., one in which the product of that reaction is detectable. As used herein, a "fluorophore" includes a molecule which is capable of absorbing energy at a wavelength range and releasing energy at a wavelength range other than the absorbance range. The term "excitation wavelength" refers to the range of wavelengths at which a fluorophore absorbs energy. The term "emission wavelength" refers to the range of wavelengths that the fluorophore releases energy or fluoresces.

In one embodiment, the reporter molecule fluoresces. One group of fluorescers is the xanthene dyes, which include the fluoresceins, rosamines and rhodamines. These compounds are commercially available with substituents on the phenyl group, which can be used as the site for bonding or as the bonding functionality. For example, amino and isothiocyanate substituted fluorescein compounds are available.

Another group of fluorescent compounds are the naphthylamines, having an amino group in the alpha or beta position, usually alpha position. Included among the naphthylamino compounds are 1-dimethylaminonaphthyl-5-sulfonate, 1-anilino-8-napththalene sulfonate and 2-p-toluidinyl-6-naphthalene sulfonate. Some naphthalene compounds are found to have some non-specific binding to protein, so that their use requires employing an assay medium where the amount of protein is minimized. Other fluorescers are multidentate ligands that include nitrogen-containing macrocycles, which have conjugated ring systems with pi-electrons. These macrocycles may be optionally substituted, including substitution on bridging carbons or on nitrogens. Suitable macrocycles include derivatives of porphyrins, azaporphyrins, corrins, sapphyrins and porphycenes and other like macrocycles, which contain electrons that are extensively delocalized. The azaporphyrin derivatives include phthalocyanine, benzotriazaporphyrin and naphthalocyanine and their derivatives.

In some instances fluorescent fusion proteins may be employed, e.g., a green, red or blue fluorescent protein or other fluorescent protein fused to a polypeptide substrate. In other embodiments, a fluorescent protein may itself be a substrate for a hydrolytic enzyme. A "fluorescent protein" is a full-length fluorescent protein or a fluorescent fragment thereof.

A non-limiting list of chemical fluorophores of use in the invention, along with their excitation and emission wavelengths, is shown in Table 2. Excitation and emission values can change depending on reaction conditions, such as pH, buffer system, or solvent.

TABLE 2

| Fluorophore | Excitation (nm) | Emission (nm) |
|---|---|---|
| Fluorescein (FITC) | 495 | 525 |
| Hoechst 33258 | 360 | 470 |
| R-Phycoerythrin (PE) | 488 | 578 |
| Rhodamine (TRITC) | 552 | 570 |
| Quantum Red ™ | 488 | 670 |
| TEXAS RED ™ | 596 | 620 |
| Cy3 | 552 | 570 |
| Rhodamine-110 | 499 | 521 |
| AFC | 380 | 500 |
| AMC | 342 | 441 |
| Resorufin | 571 | 585 |
| BODIPY FL | 504 | 512 |
| BODIPY TR | 591 | 620 |

In one embodiment, one of the enzymes is detected using a substrate which includes an amino-modified luciferin or a carboxy protected derivative thereof, which modification includes a substrate for the enzyme. In one embodiment, the modification is one or more amino acid residues which include a recognition site for a protease. In one embodiment, the substrate is covalently linked to the amino group of aminoluciferin or a carboxy-modified derivative thereof via a peptide bond. In one embodiment, the N-terminus of a peptide or protein substrate is modified to prevent degradation by aminopeptidases, e.g., using an amino-terminal protecting group. In the absence of the appropriate enzyme or cofactor, a mixture including such a substrate and luciferase generates minimal light as minimal aminoluciferin is present. In the presence of the appropriate enzyme, the bond linking the substrate and aminoluciferin can be cleaved by the enzyme to yield aminoluciferin, a substrate for luciferase. Thus, in the presence of luciferase, for instance, a native, recombinant or mutant luciferase, and any cofactors and appropriate reaction conditions, light is generated, which is proportional to the presence or activity of the enzyme.

In one embodiment, one of the enzymes is detected using a substrate which includes a fluorophore. In one embodiment, the substrate includes one or more amino acid residues which include a recognition site for a protease. In one embodiment, the substrate is covalently linked to one or more fluorophores. In the absence of the appropriate enzyme or cofactor, a mixture including such a substrate generates minimal light at the emission wavelength as the fluorescent properties of the fluorophore are quenched, e.g., by the proximity of the quenching group such that the properties of a substrate-fluorophore conjugate are changed, resulting in altered, e.g., reduced, fluorescent properties for the conjugate relative to the fluorophore alone. In the presence of the appropriate enzyme, cleavage of the conjugate yields the fluorophore. In another embodiment, prior to cleavage, the conjugate is fluorescent but after cleavage with the enzyme, the product(s) have altered spectra.

In one embodiment, the conditions for at least two of the reactions are compatible. For instance, the conditions for at least 2 enzymes, and preferably the conditions for 3 or more enzymes, e.g., 4 or more enzymes, are compatible. A group of similar enzymes will generally have compatible reaction conditions, such as pH and ionic strength, however, cofactor requirements, metal ion requirements, and the like, involving assay components having relatively low mass concentrations, e.g., cofactors, need not be common. Common conditions include conditions such that each of the enzymes provides a measurable rate during the course of the reaction and will generally be that each of the enzymes has at least about 10%, usually at least about 20%, preferably at least about 50%, of its maximum turnover rate for the particular substrate, without significant interference from the components added for the other enzyme(s).

Alternatively, the conditions for one reaction may not be compatible with another reaction although substrates for both reactions are present. In such embodiments, one enzyme is active but cannot react with its substrate. In one embodiment, for example, where conditions for two reactions are not compatible, individual enzyme-assay reactions are carried out sequentially and/or in separate reaction mixtures. Following the enzyme assay, the reaction mixture (or a portion thereof) may be combined with another reaction. Each individual reaction mixture may contain one or more enzymes and one or more substrates. In its simplest form, a single enzyme to be assayed and a single substrate for that enzyme are in each reaction mixture. The set of substrates employed in the reaction has the same general properties as that required in the single-reaction multiplexed assay. That is, each substrate and/or corresponding product have unique characteristics, allowing them to be distinguished from one another.

The order of detection of molecules in the reactions can vary. In one embodiment, regardless of whether reactions are initiated at the same time or not, the molecule detected by a luminogenic assay is detected, then the molecule detected by the nonluminogenic assay is detected. Alternatively, regardless of whether reactions are initiated at the same time or not, the molecule detected by the nonluminogenic assay is detected, then the molecule detected by the luminogenic assay is detected. In other embodiments, the presence or amount of two or more molecules is detected essentially simultaneously. In one embodiment, the presence or activity of one molecule to be detected is substantially decreased prior to detecting the presence or activity of the second molecule, e.g., by waiting until the first signal has diminished, e.g., by at least 50%, or by adding a quenching agent for the first reaction. Thus, in some embodiments, one or more of the reactions are terminated, e.g., by inhibiting an enzyme for the reaction, prior to detection. Preferably, the signal produced by one assay does not substantially interfere with the quantification of the signal produced by at least one other assay.

The present invention also provides kits for detecting the presence or activity of one or more peptides or proteins, molecules which bind to and/or are altered by the peptides or proteins, or cofactors in a sample such as a sample including intact cells, a cell lysate, e.g., a lysate which is at least partially purified, or a cellular supernatant. Such a kit includes at least one reagent for quantifying at least one of the peptides and/or proteins, molecules bound by and/or altered by the peptides and/or proteins, or cofactors, such as a substrate for at least one enzyme.

The invention will be further described by the following non-limiting examples. For all examples, suitable control reactions are readily designed by those skilled in the art.

EXAMPLE I

Fluorescent/Luminescent Multiplex Assays

A. Measurement of Caspase-3 and Caspase-8 in a Single Well, Multiplex Assay

Caspase-Glo™ 8 Reagent (Caspase-Glo™ 8 Assay System, Promega, Corp.) was evaluated for its ability to allow multiplexing of homogeneous luminogenic caspase-8 and nonluminogenic caspase-3 enzyme assays. Caspase-Glo™ 8 Reagent is comprised of Caspase-Glo™ 8 Buffer and the luminogenic substrate Z-LETD-aminoluciferin (LETD corresponds to SEQ ID NO:14). For the luminogenic assays in FIG. 1A, either Caspase-Glo™ 8 Reagent (diamonds) or Caspase-Glo™ 8 Reagent also containing 50 µM of the fluorogenic substrate for caspase-3, (Z-DEVD)$_2$-rhodamine-110 (squares) (DEVD corresponds to SEQ ID NO:1), was used to demonstrate the feasibility of a multiplexed luminogenic and nonluminogenic assay. For the fluorogenic assay in FIG. 1B, Caspase-Glo™ 8 Buffer containing either 50 µM (Z-DEVD)$_2$-rhodamine-110 (DEVD corresponds to SEQ ID NO:1) and 10 mM DTT (diamonds) or 50 µM (Z-DEVD)$_2$-rhodamine-110 (DEVD corresponds to SEQ ID NO:1) and Z-LETD-aminoluciferin (squares) (LETD corresponds to SEQ ID NO:14) were used.

Dilutions of caspase-8 enzyme, caspase-3 enzyme, and combined caspase-8 and caspase-3 enzymes (Biomol Research Laboratories) were prepared in RPMI 1640 (Sigma Corporation) to a final concentration of 100 units/ml. 100 µl of caspase-8 dilutions, a mixture of caspase-8 and caspase-3 dilutions, or caspase-3 dilutions, were added to separate wells of a 96-well plate. 100 µl of Caspase-Glo™ 8 Reagent with or without 50 µM (Z-DEVD)$_2$-rhodamine-110 (DEVD corresponds to SEQ ID NO:1) (FIG. 1A), or 100 µl of Caspase-Glo™ 8 Buffer supplemented with (Z-DEVD)$_2$-rhodamine 110 (DEVD corresponds to SEQ ID NO:1) and DTT with or without Z-LETD-aminoluciferin (LETD corresponds to SEQ ID NO:14) (FIG. 1B) were added to reach a final volume of 200 µl/well. The reaction plate was incubated at room temperature for at least ten minutes on a plate shaker.

After incubation, relative luminescence was determined using a DYNEX Laboratories MLX™ plate luminometer, and relative fluorescence was measured with a CYTOFLUOR™ II Fluorescent plate reader outfitted with a $485_{EX}/530_{EM}$ filter set.

Results

The simultaneous measurement of fluorescence and luminescence for two protease enzymes in a single well is shown in FIG. 1. As seen in FIG. 1A, the presence of caspase-3 and its fluorogenic substrate, (Z-DEVD)$_2$-rhodamine-110 (DEVD corresponds to SEQ ID NO:1), in a luminogenic assay for caspase-8 (squares) does not greatly alter the luminescent reaction. Similarly, as seen in FIG. 1B, the presence of caspase-8 and its luminogenic substrate Z-LETD-aminoluciferin (LETD corresponds to SEQ ID NO:14) in a fluorogenic assay for caspase-3 (squares) does not impact the fluorogenic assay for caspase-3.

B. Background Determinations for a Caspase-3 and Caspase-8 Multiplex Assay

Various concentrations of luminogenic and fluorogenic reagents, including caspase enzymes and substrates thereof, and buffer components were combined to establish each constituent's contribution to fluorescence and/or luminescence. The fluorogenic substrate (Z-DEVD)$_2$-rhodamine-110 (DEVD corresponds to SEQ ID NO:1) reports caspase-3 activity in the rhodamine channel ($485_{EX}/520_{EM}$) and the fluorogenic substrate Ac-DEVD-AMC (DEVD corresponds to SEQ ID NO:1) reports the caspase-3 activity in the AMC channel ($360_{EX}/460_{EM}$), while the substrate Z-LETD-aminoluciferin (LETD corresponds to SEQ ID NO:14) reports caspase-8 activity during luminescence measurement. Table III describes the amount of each component (µl) for twelve different reaction conditions resulting in a total volume of around 500 µl of master mix, or 100 µl of master mix/reaction (n=4) for each reaction condition. For the 'caspase added' row, the number in this row defines the type of caspase added in overabundance and does not describe a volume.

TABLE 3

| Component | 1 | 2 | 3 | 4 | 5 | 6 | 7 | 8 | 9 | 10 | 11 | 12 |
|---|---|---|---|---|---|---|---|---|---|---|---|---|
| Caspase-Glo ™ 8 Buffer | 400 | 400 | 400 | 400 | 400 | 400 | 400 | 400 | 400 | 400 | 400 | 495 |
| Caspase-Glo ™ 8 lyophilized substrate reconstituted in 1 ml of water | 100 | na | na | 100 | 100 | 100 | 100 | 100 | 100 | 100 | 100 | na |
| 5 mM (Z-DEVD)$_2$-rhodamine-110 (DEVD corresponds to SEQ ID NO: 1) | na | 5 | na | 5 | 5 | na | na | na | 5 | 5 | na | 5 |
| 5 mM Ac-DEVD-AMC (DEVD corresponds to SEQ ID NO: 1) | na | na | 5 | na | na | 5 | na | na | na | na | na | na |
| DMSO | 5 | na | na | na | na | na | 5 | 5 | na | na | 5 | na |
| 100 mM Hepes | na | 80 | 80 | na | na | na | na | na | na | na | na | na |
| 1 M DTT | na | 20 | 20 | na | na | na | na | na | na | na | na | na |
| Caspase-3 inhibitor (in excess) | na | na | na | na | Yes | na | na | Yes | na | na | Yes | na |
| Caspase added | 8 | 3 | 3 | 8&3 | 8&3 | 8&3 | 3 | 3 | 8 | 3 | 8 | 3 |

1. Caspase-8 luc control
2. Caspase-3 rhodamine-110 control
3. Caspase-3 AMC control
4. Multiplex control with rhodamine-110
5. Multiplex control with rhodamine-110 + inhibitor
6. Multiplex control with AMC
7. Capase-3 with aminoluciferin mix
8. Caspase-3 with aminoluciferin mix + inhibitor
9. Caspase-8 with rhodamine-110
10. Caspase-3 with aminoluciferin mix
11. Caspase-8 with aminoluciferin mix + inhibitor
12. Caspase-3 with rhodamine-110 without aminoluciferin mix The components from Table III were added to replicate wells and reactions were incubated at room temperature for two hours. The buffer employed was that from the Caspase-Glo™ 8 Assay System. DMSO was obtained from Sigma-Aldrich and the DTT was obtained from Amresco. The substrates and inhibitors were obtained from Promega Corp.

Relative luminescence was determined using a DYNEX Laboratories MLX™ plate luminometer. Fluorescence was determined using a CYTOFLUOR™ II Fluorescent plate reader outfitted with a $485_{EX}/530_{EM}$ filter set for rhodamine-110 and then $360_{EX}/460_{EM}$ for the AMC channel.

Results

Figure 2A:
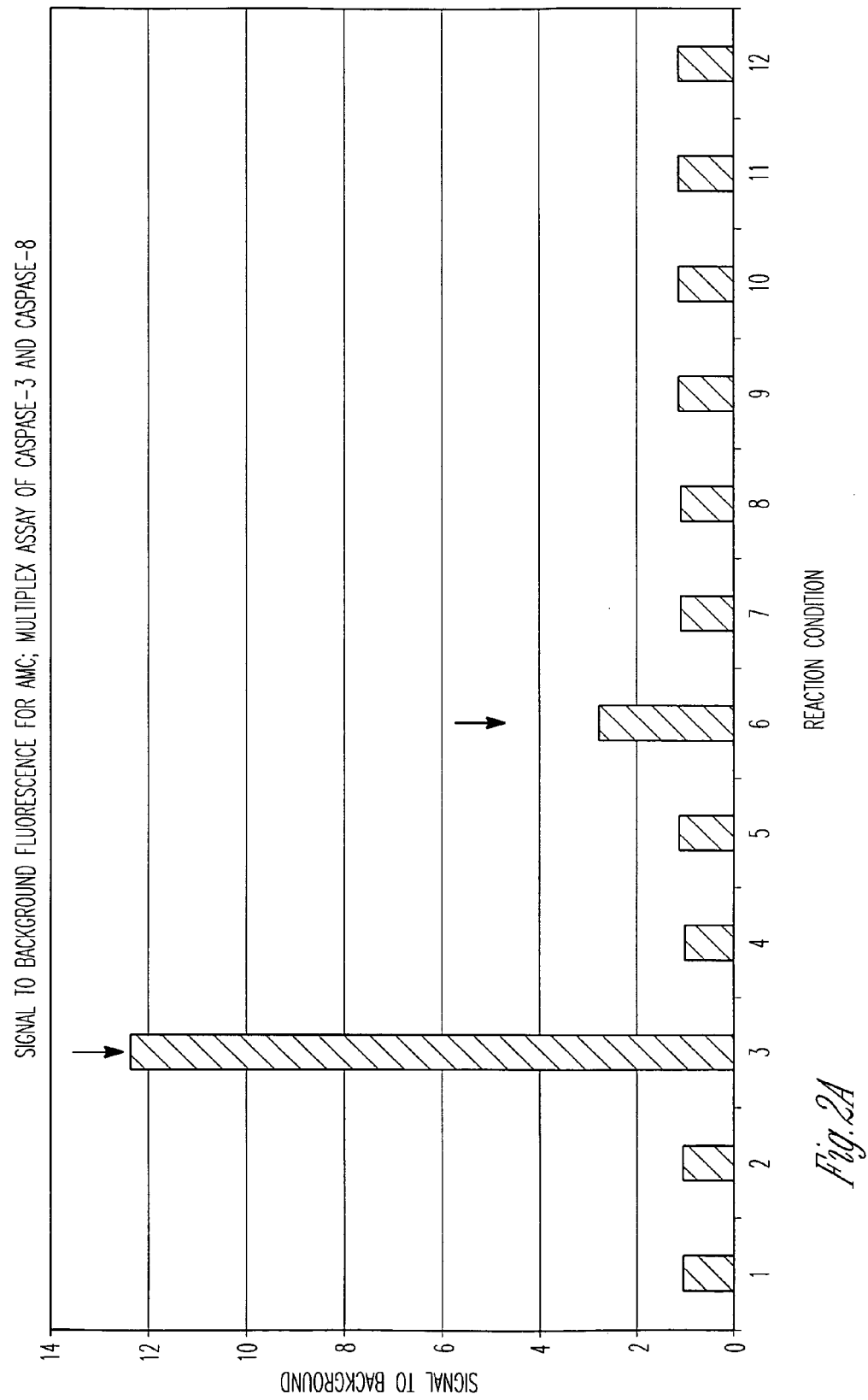

For FIGS. 2A, B, and C, all carats represent where either fluorescence or luminescence indicating enzyme activity was expected. FIG. 2A shows the signal for AMC fluorescence in each reaction. Fluorescence above background was only present where the appropriate substrate/enzyme combination of Ac-DEVD-AMC (DEVD corresponds to SEQ ID NO:1) and caspase-3 was present (reaction conditions 3 and 6). FIG. 2B shows the signal for rhodamine-110 fluorescence in each reaction. Fluorescence above background was present where the substrate/enzyme combination of $(Z-DEVD)_2$-rhodamine-110/caspase-3 (DEVD corresponds to SEQ ID NO:1) was present (reaction conditions 2, 4, 10, and 12), except when a caspase-3 inhibitor was present (reaction condition 5). For luminescence signal above background (FIG. 2C), those reactions with the appropriate substrate/enzyme combination of Z-LETD-aminoluciferin/caspase-8 (LETD corresponds to SEQ ID NO:14) showed signal above background (reaction conditions 1, 4, 6, 7, 9, and 10), except those reaction conditions where a caspase inhibitor was present (reaction conditions 5, 8, and 11). The data thus demonstrate that there was negligible contribution of reaction components to background fluorescence and luminescence measurements under these conditions.

C. Measurement of Caspase-3, Caspase-8, and Trypsin in a Single Well, Triplex Assay Dilutions of detectable levels of caspase-8 (150 units/ml, Biomol Research Laboratories), caspase-3 (Pharmingen Corp.), trypsin (Sigma Corp.), and a combination of all three enzymes, were prepared in Dulbecco's phosphate buffered saline (Sigma Corp.). 100 µl of each enzyme dilution were added to the wells of a 96-well plate and 100 µl of each substrate, either singly or in combination as appropriate, were added to the corresponding wells: substrate $(Z-DEVD)_2$-rhodamine-110 (DEVD corresponds to SEQ ID NO:1) for caspase-3, substrate Z-PRNK-AMC (PRNK corresponds to SEQ ID NO:27) for trypsin (as described in U.S. patent application Ser. No. 09/955,639 as a substrate for beta-tryptases but with a recognized lesser utility for trypsin, incorporated herein in its entirety), and substrate Z-LETD-aminoluciferin (LETD corresponds to SEQ ID NO:14) for caspase-8. When Caspase-Glo™ 8 Buffer was employed with a substrate for a fluorogenic assay, 10 mM DTT was included. Plates were incubated for at least ten minutes at room temperature on a plate shaker.

Following incubation, relative luminescence for caspase-8 activity was measured using BMG Fluorostar (BMG Labtechnologies Ltd.). Relative fluorescence was determined using the Labsystems FLUOROSKAN ASCENT™ plate reader. For caspase-3 activity, a filter set of $485_{EX}/527_{EM}$ was utilized. For trypsin activity, a filter set of $360_{EX}/460_{EM}$ was used.

Results

Figure 3A:
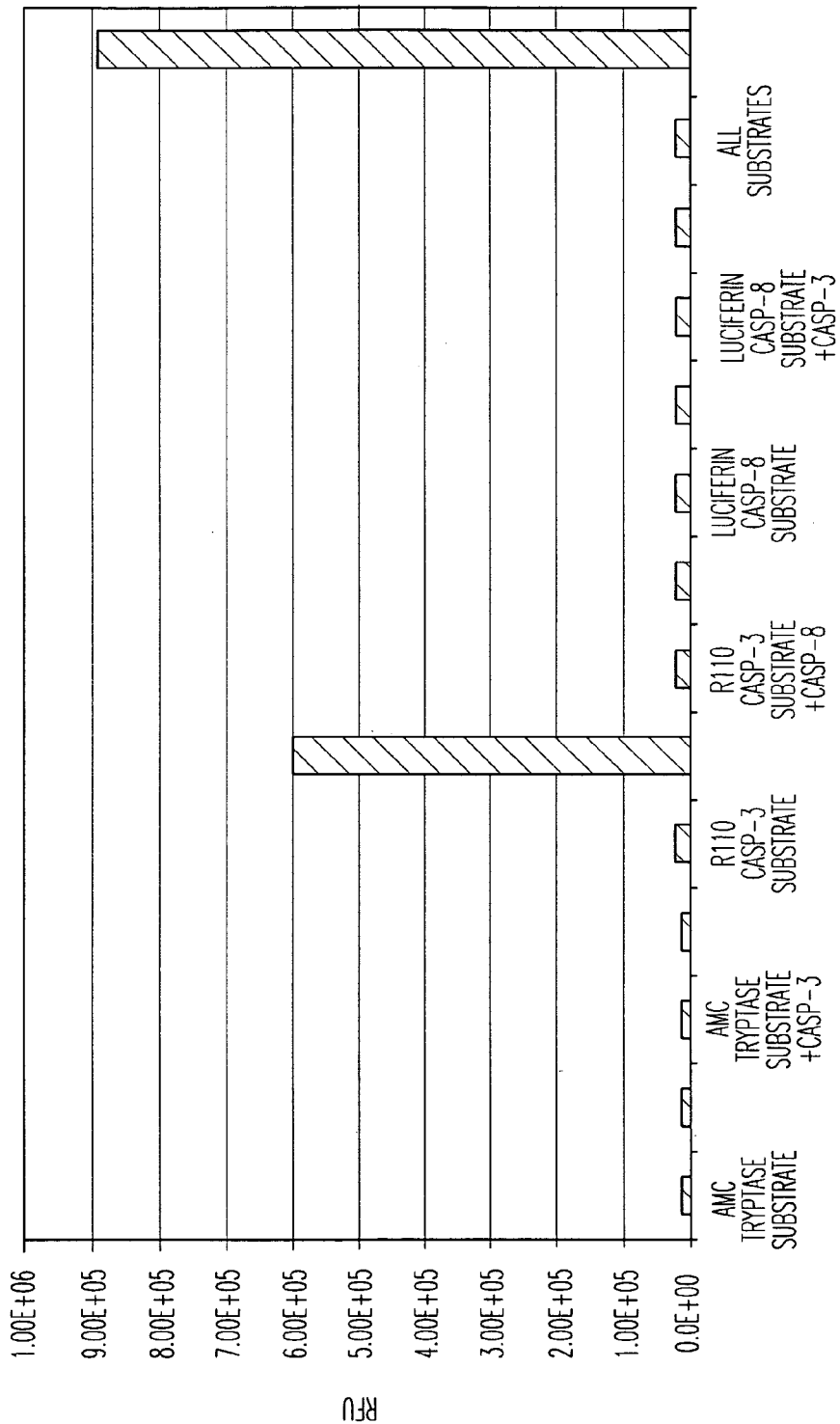
Figure 3B:
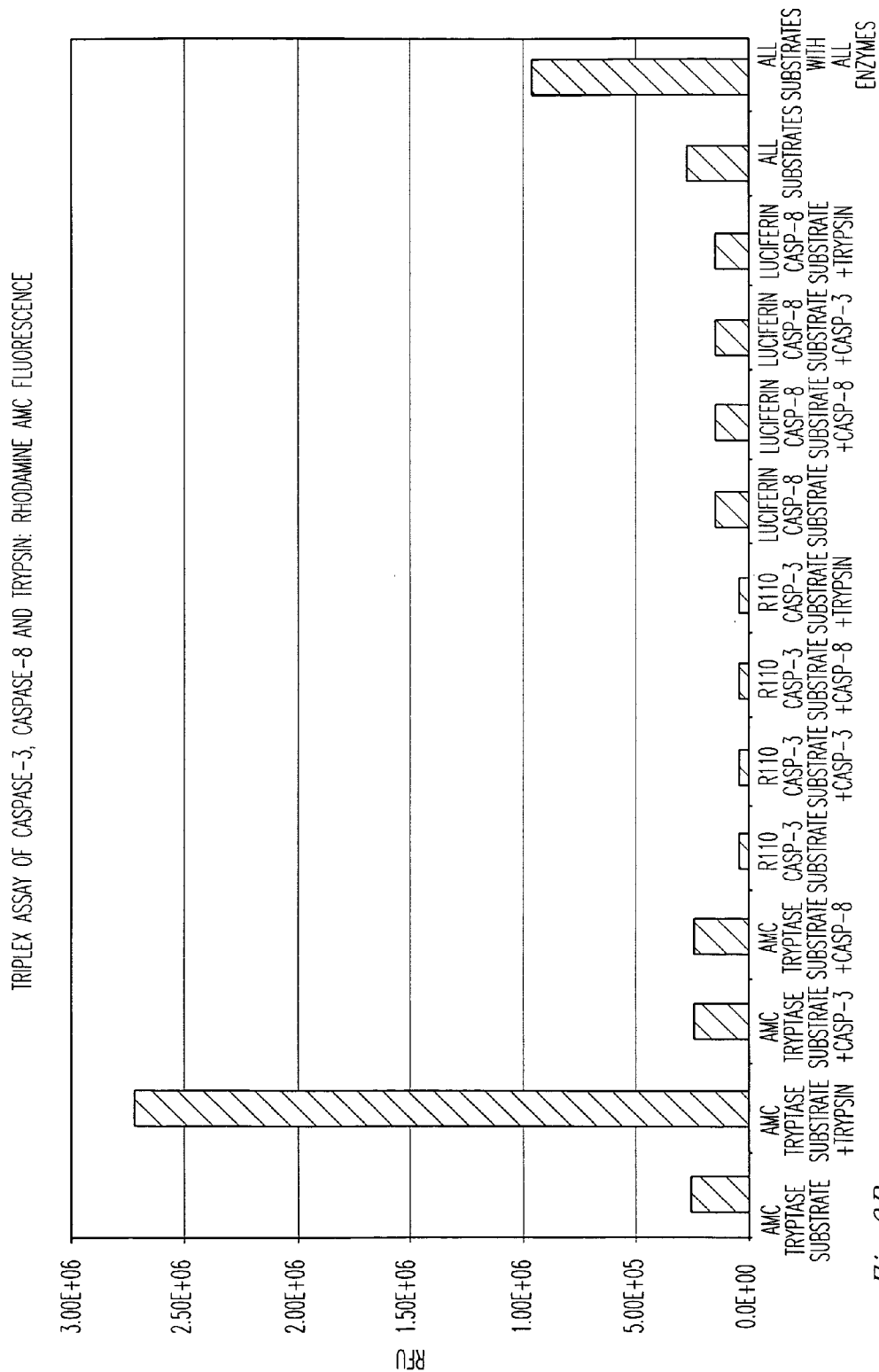

As shown in FIG. 3A, the conditions employed to detect caspase-3 in a reaction with three different substrates and corresponding enzymes combined (the triplex assay) yielded relatively high fluorescence over that of the control conditions. When comparing the activity of caspase-3 in the triplex assay (all substrates with all enzymes) to that of caspase-3 alone, caspase-3 activity was greater than background when caspase-3 was in the same reaction with the other triplex enzyme reactions. Similar results were seen for trypsin (FIG. 3B) and caspase-8 (FIG. 3C), albeit not to the same extent as with caspase-3.

D. Measurement of Caspase-3 and β-Galactosidase in a Single Well, Multiplex Format Reagents were prepared by reconstituting Beta-Glo® lyophilized substrate with Beta-Glo® Buffer (Beta-Glo® Assay System, Promega Corp.), or adding $(Z-DEVD)_2$-rhodamine-110 (DEVD corresponds to SEQ ID NO:1) (50 µM) to Beta-Glo® Buffer, or reconstituting Beta-Glo® lyophilized substrate with Beta-Glo® Buffer and adding $(Z-DEVD)_2$-rhodamine-110 (DEVD corresponds to SEQ ID NO:1) (50 µM). Caspase-3 (2 µl/ml, Pharmingen Corp), or β-galactosidase (0.1 µl/ml), or caspase-3 and β-galactosidase, were diluted in RPMI 1640 and 100 µl were added to wells of a 96-well white plate. 100 µl of the appropriate reagent were added to wells of a 96-well plate and the plates were incubated at room temperature. Luminescence was measured using a DYNEX Laboratories MLX™ plate luminometer at 30 minutes. Fluorescence was measured 2 hours post incubation on a CYTOFLUOR™ II Fluorescent plate reader with a filter set of $485_{EX}/530_{EM}$. All measurements were repeated at 18 hours with different gain settings on the CYTOFLUOR™ II fluorometer to compensate for increased fluorescence.

Figure 4A:
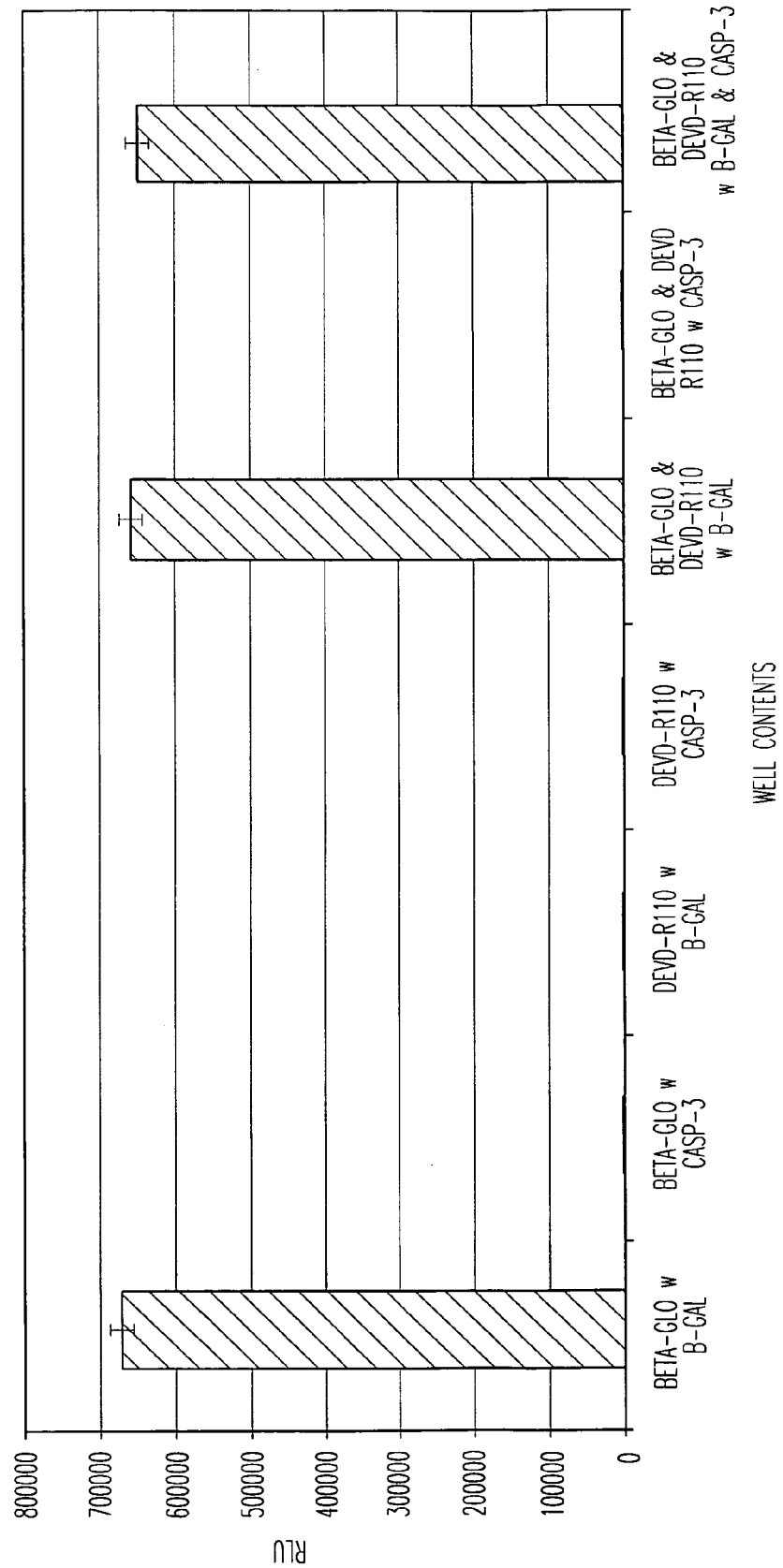
Figure 4B:
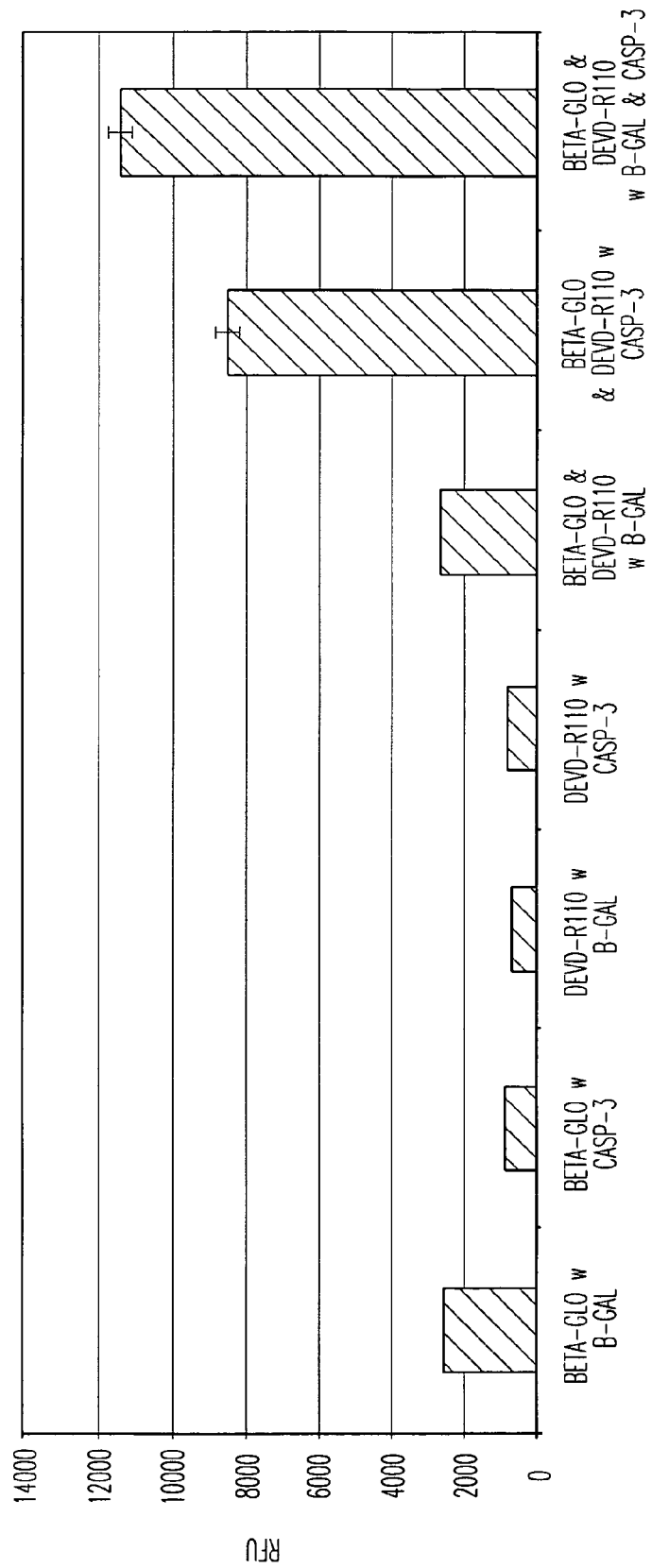
Figure 4C:
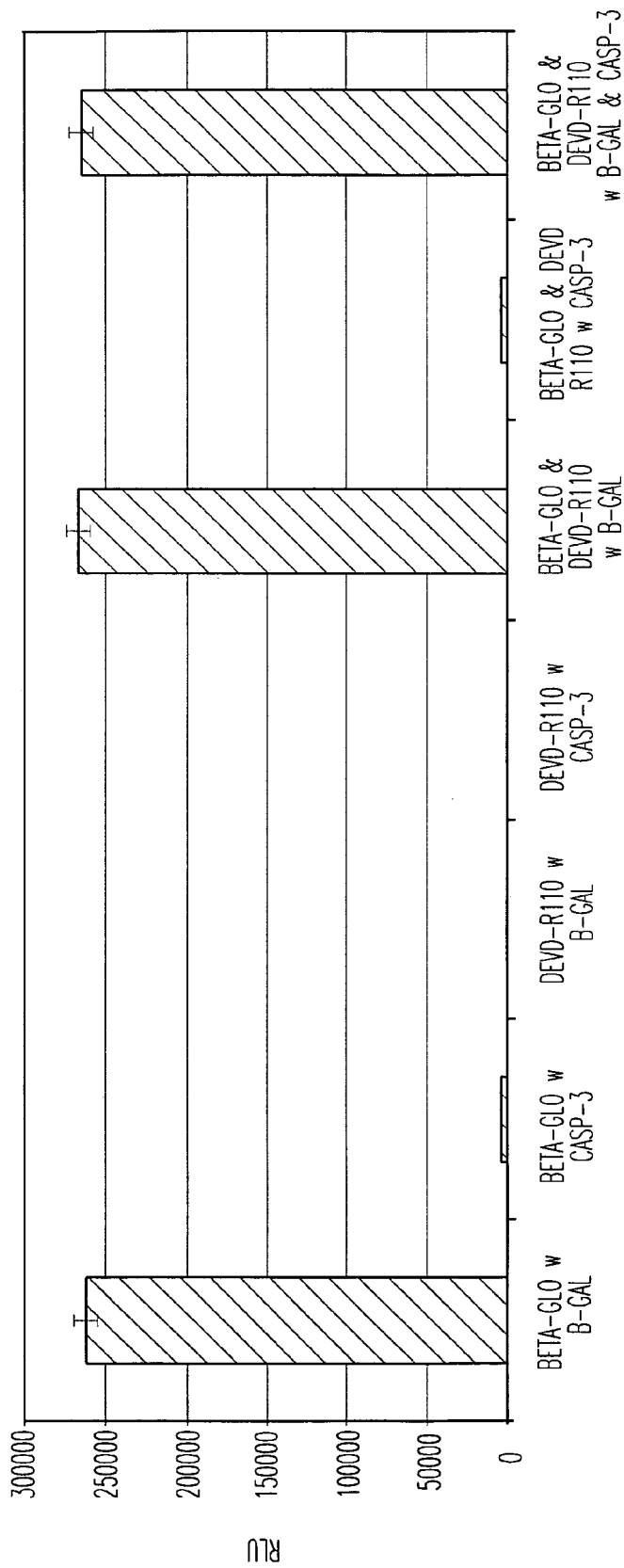

FIGS. 4A and C demonstrate the luminogenic assay for β-galactosidase is functional in the presence of the fluorogenic reagent to measure caspase-3. FIGS. 4B and D demonstrate the fluorogenic assay to measure caspase-3 is functional in the presence of the luminogenic reagent to measure β-galactosidase. As seen in FIGS. 4B and 4D, there was a minor contribution of the luminogenic reagent components to background fluorescence. However, there was almost no contribution of the fluorogenic reagent components to luminescence (FIGS. 4A and 4C).

E. Spectral Scans of Substrates for Luminogenic Assays

Luciferin, aminoluciferin, and Z-LETD-aminoluciferin (LETD corresponds to SEQ ID NO:14), were diluted to approximately 2 µM in a buffer containing 0.1 M Tris pH 7.3, 2 mM EDTA, and 10 mM $MgSO_4$. Samples were scanned on a SPEX FLUOROLOG™-2 spectrometer with 1.25 mm excitation and emission slit filter present, at 1 nm wavelength interval and 0.2 second integration time. All scans were performed using a quartz cuvette.

Results

Figure 5A:
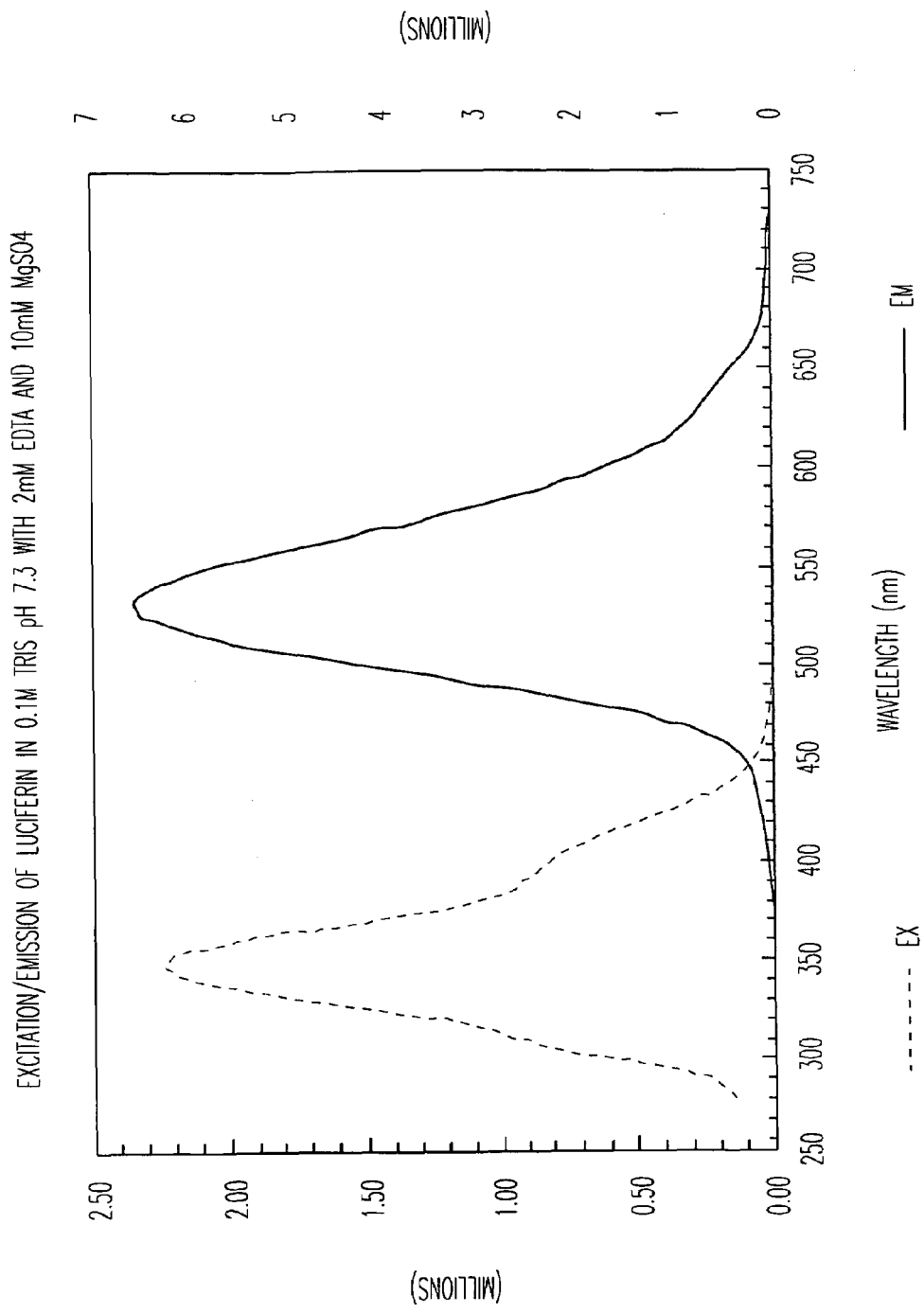
FIGS. 5A-C. Excitation and emission spectra of luciferin (A), aminoluciferin (B) and Z-LETD-aminoluciferin (LETD corresponds to SEQ ID NO:14) (C).
Figure 5B:
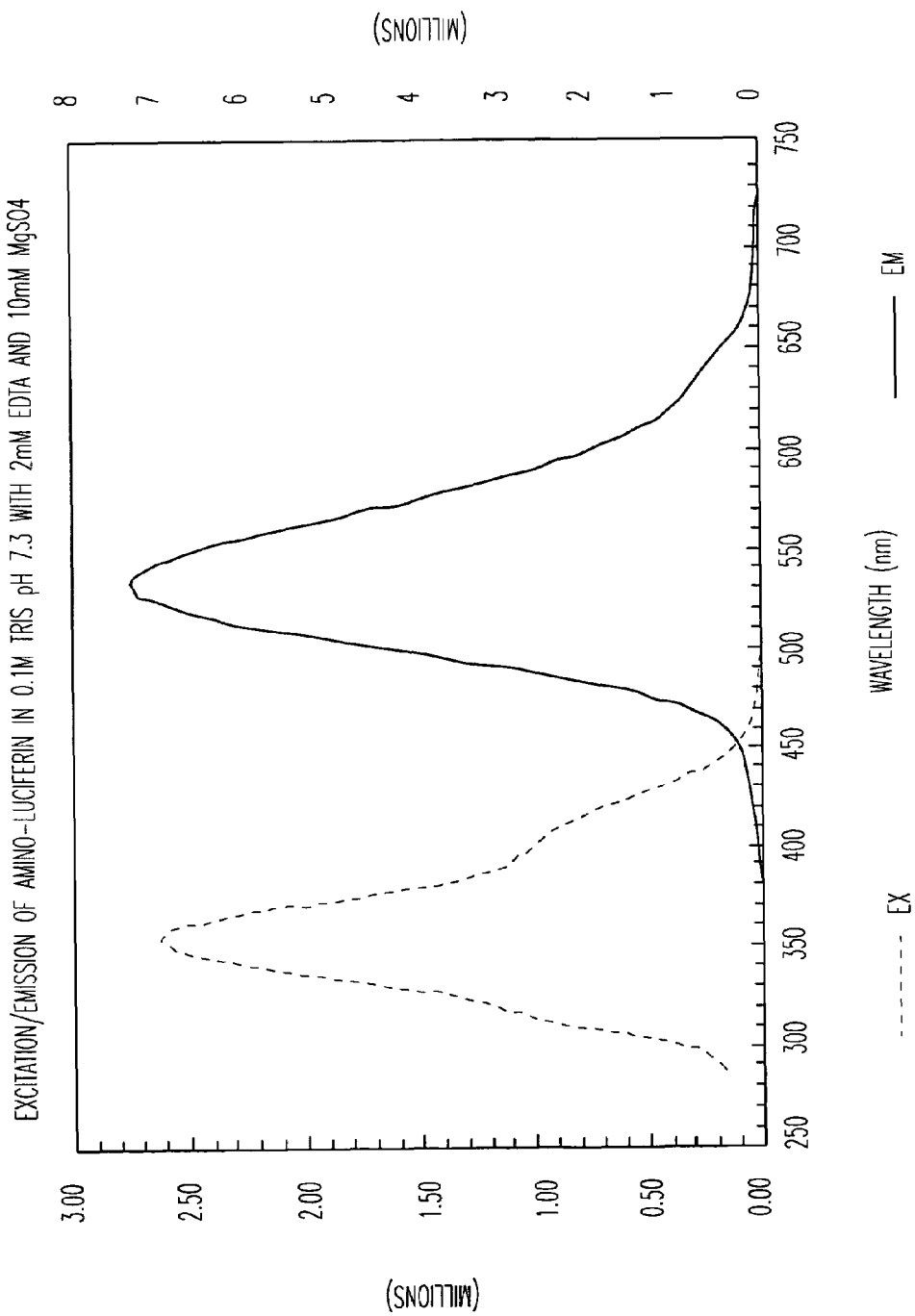
Figure 5C:
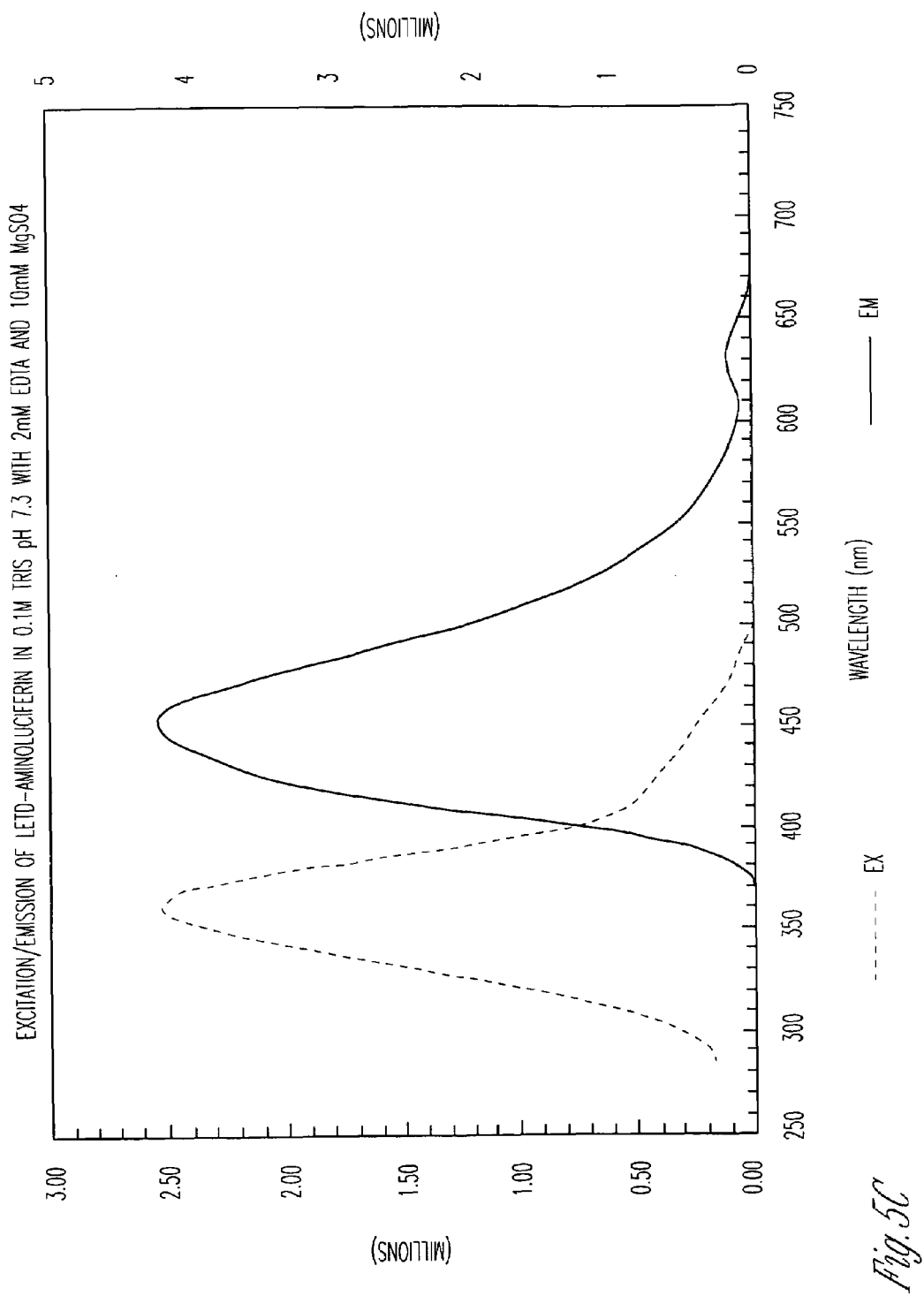

For luciferin and aminoluciferin, excitation was at 325 nm and emission was captured from 375 to 750 nm, and excitation was captured at 280-550 nm with emission measured at 600 nm (FIGS. 5A and 5B). For Z-LETD-aminoluciferin (LETD corresponds to SEQ ID NO:14), excitation was at 325 nm and emission was captured between 375-750 mn, and excitation was captured at 280-500 nm with emission measured at 525 nm (FIG. 5C). Interestingly, when a peptide was conjugated to aminoluciferin (FIG. 5C), the emission peak of the conjugate was blue shifted to shorter wavelengths. This was unexpected and therefore allows for dual luminscence/ fluorescent measurements, particularly when using a fluorophore that emits in the same wavelength range as aminoluciferin emits.

EXAMPLE II

Method to Detect False Results

Methods

Caspase-Glo™ 3/7 Reagent (Caspase-Glo™ 3/7 Assay, Promega, Corp.) which contains Z-DEVD-aminoluciferin (DEVD corresponds to SEQ ID NO:1) was combined with (Z-DEVD)$_2$-rhodamine-110 (DEVD corresponds to SEQ ID NO:1) or Ac-DEVD-AMC (DEVD corresponds to SEQ ID NO:1) in the presence of caspase-3 with either a caspase-3 inhibitor (Ac-DEVD-CHO (DEVD corresponds to SEQ ID NO:1), 10 µM) or with a luciferase inhibitor (Resveratol, 5 µM). The luminescent signal from caspase-3 cleavage of Z-DEVD-aminoluciferin (DEVD corresponds to SEQ ID NO:1) was read at 30 minutes, while the fluorescent signals from caspase-3 cleavage activity were read at 2 hours using the appropriate AMC or rhodamine 110 filter sets.

Results

Luminescence gave the largest signal to background ratio, followed by rhodamine-110, then AMC (FIG. 6). All three substrates for detecting caspase-3 were consistently and negatively impacted by the addition of a known caspase-3 inhibitor. This suggests that luminogenic and fluorogenic reagents can be combined, e.g., to control for potential false interferences when either assay is performed. Thus, multiplexed signals can be used to determine if an agent is a true inhibitor of a particular enzyme.

EXAMPLE III

Additional Exemplary Multiplex Assays

A. Multiplex Assay For Lactate Dehydrogenase (LDH) and Adenosine Triphosphate (ATP) in a Single Well Format The following detection reagents were prepared:1) LDH reagent (30 mM HEPES, pH 7.4, 10 mM NaCl, 20 mM MgSO$_4$, 250 µM resazurin (Aldrich)) was used to reconstitute the lyophilized substrate component from CytoTox-ONE™ Homogeneous Membrane Integrity Assay (Promega Corp, Technical Bulletin 306); 2) ATP reagent (30 mM HEPES pH 7.4, 10 mM NaCl, 20 mM MgSO$_4$) was used to reconstitute the lyophilized substrate from CellTiter-Glo™ Luminescent Cell Viability Assay (Promega Corp, Technical Bulletin 288); 3) LDH/ATP combination reagent (30 mM HEPES pH 7.4, 10 mM NaCl, 20 mM MgSO$_4$, 250 µM resazurin (Aldrich)) was used to reconstitute the lyophilized substrate component from CytoTox-ONE™, which in turn was used to reconstitute the lyophilized substrate from CellTiter-Glo™.

Sample dilutions of LDH (0, 1:8000, 1:4000, 1:2000, diamonds), ATP (0, 1.25, 2.5, and 5 µM, squares), and a combination of LDH/ATP (0/0 µM, 1:8000/1.25 µM, 1:4000/2.5 µM, and 1:2000/5 µM, respectively, triangles) were made with a 10 mM HEPES pH 7.5, 0.1% PRIONEX™ (PentaPharma Corp) solution, and 100 µl of the dilutions (n=4) were added to wells of a white, 96-well plate. The appropriate detection reagent (100 µl) was added to the samples, the plates were protected from light, mixed for 30 seconds, and incubated at room temperature. Following an eight minute incubation, fluorescence was measured on a Labsystems FLUOROSKAN ASCENT™ plate reader with filter set 560$_{EX}$/590$_{Em}$. At 30 minutes post-incubation luminescence was recorded using a Dynex MLX plate luminometer.

Results

Figure 7A:
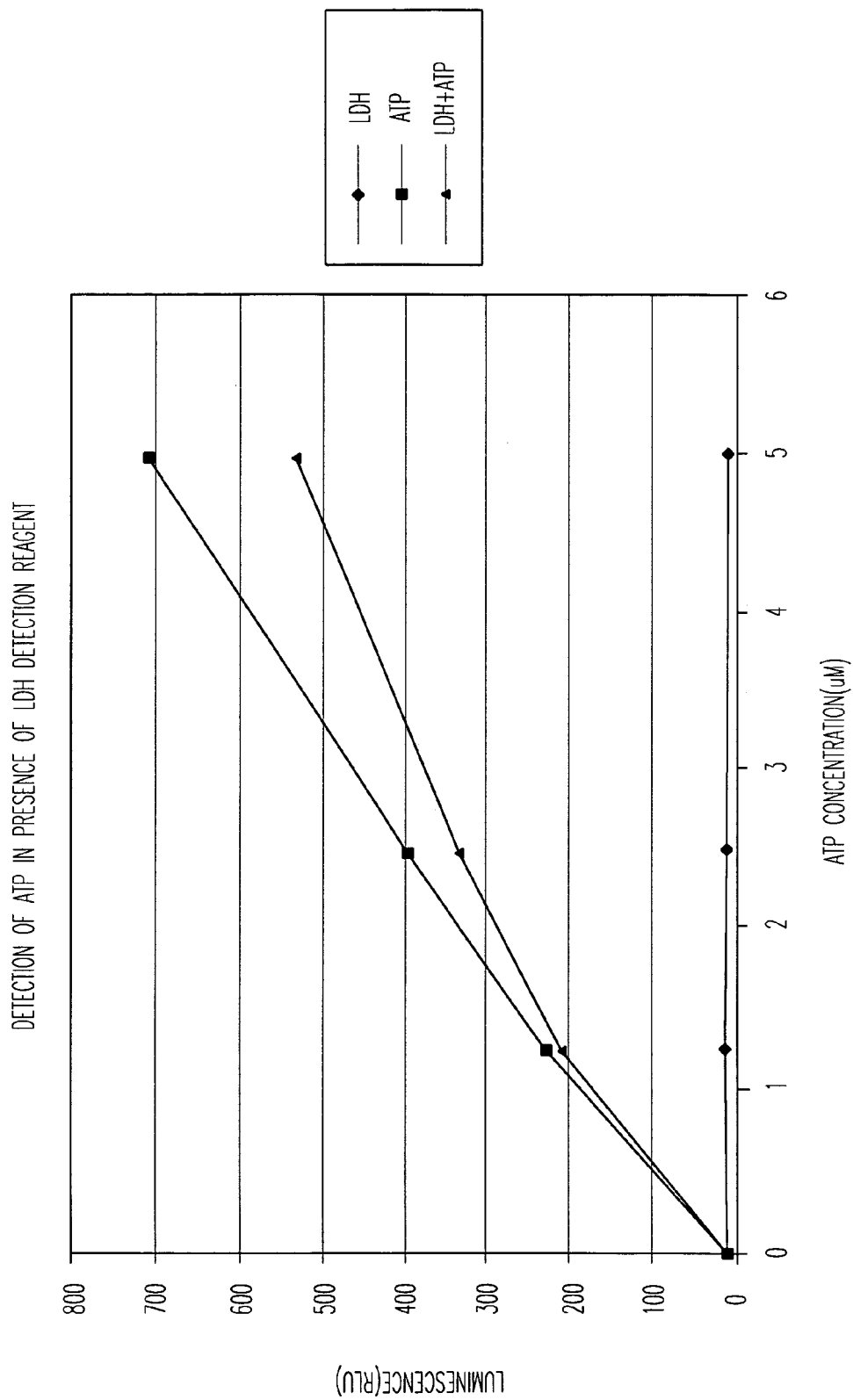
Figure 7B:
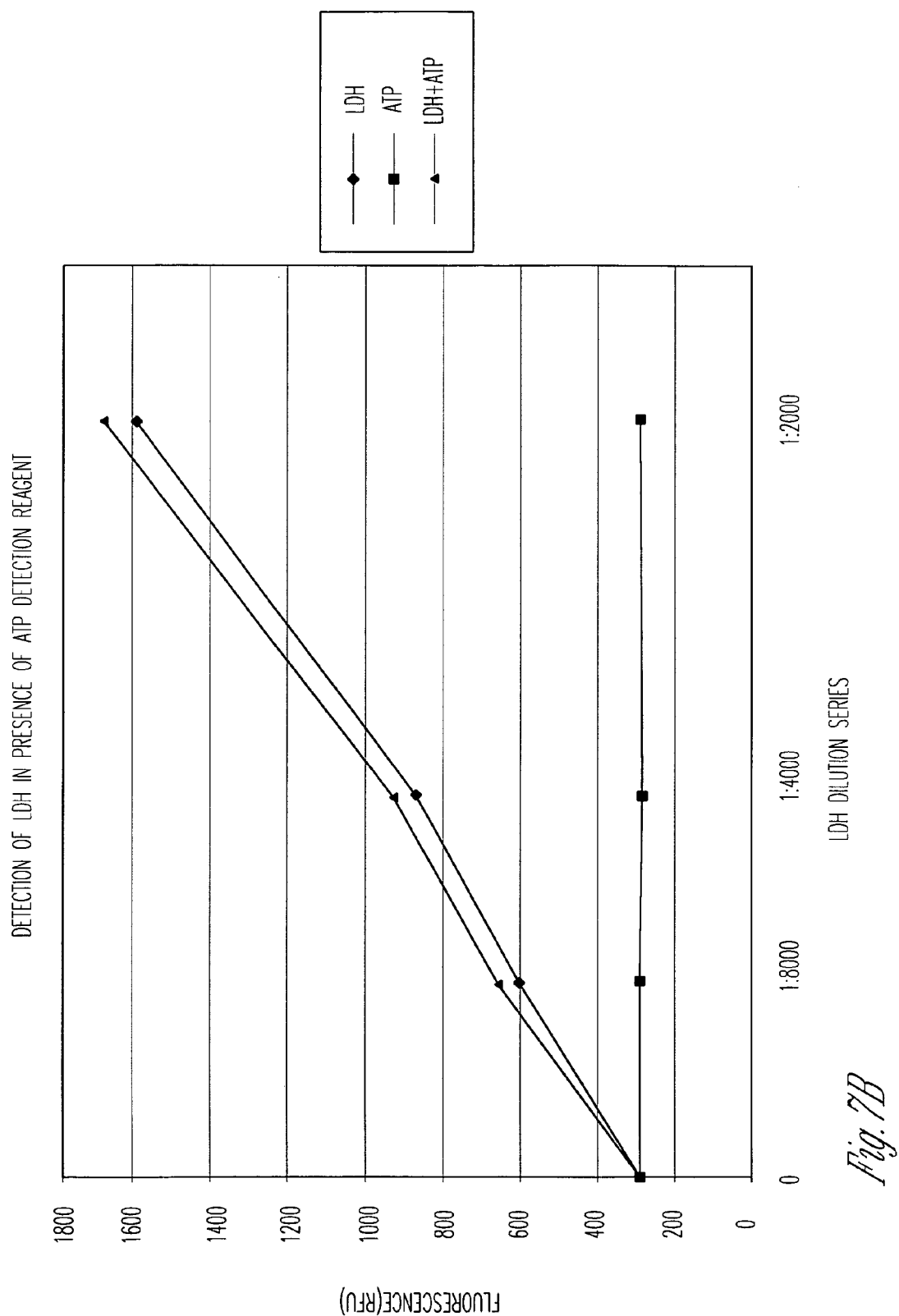
Figure 7C:
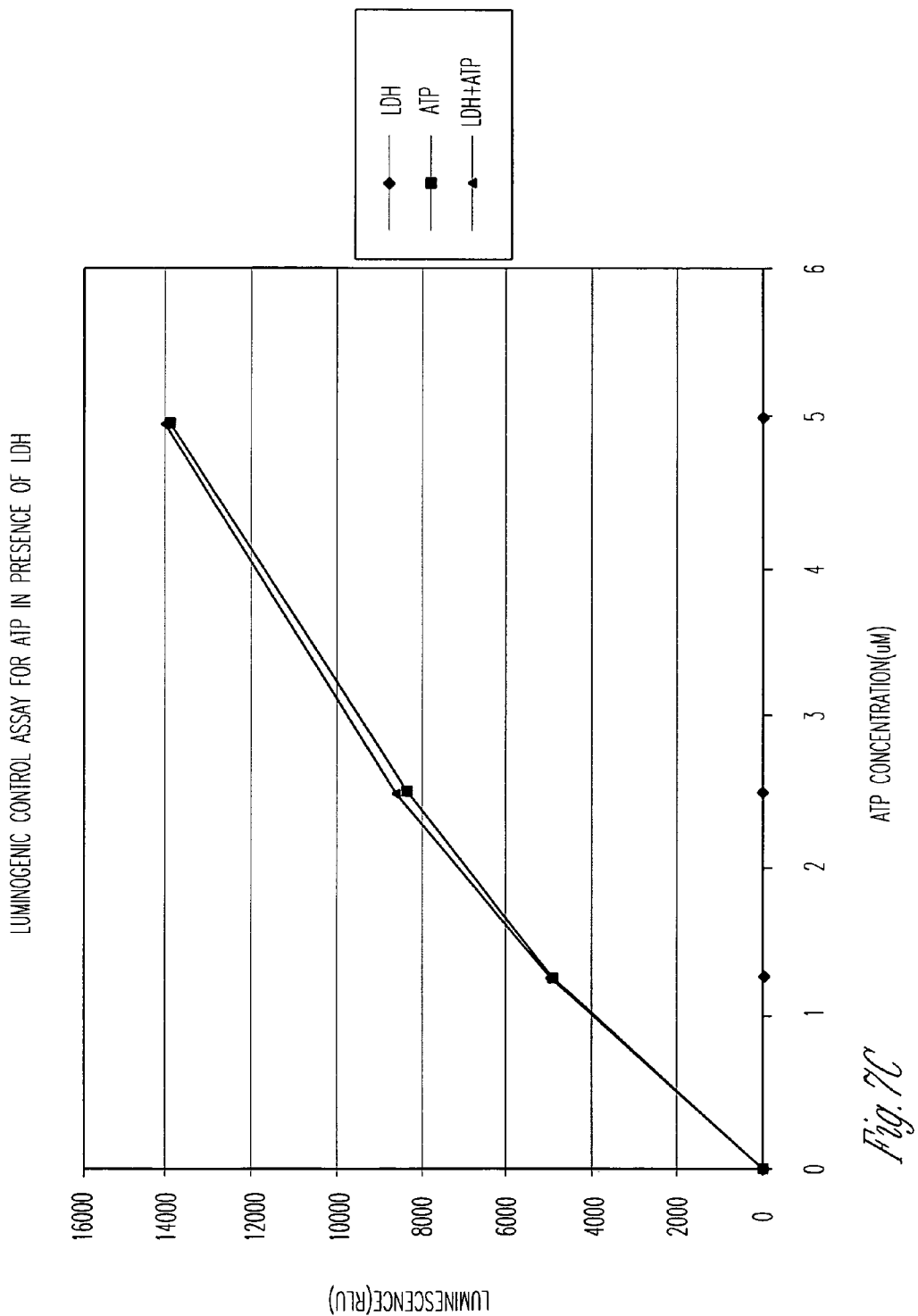

There was a minor effect of LDH and its fluorogenic detection reagent on the luminogenic assay for ATP (FIG. 7A) when compared to the control reaction (FIG. 7C); however, detection of ATP was still possible. The addition of a luminogenic detection reagent to the fluorogenic assay for LDH did not affect background fluorescence (FIG. 7B), and although overall fluorescence decreased when compared to the control reaction (FIG. 7D) LDH activity was still detectable.

B. Multiplex Assay for LDH and Caspase-3 in a Single Well Format

The following detection reagents were prepared: 1) PKA reagent-a 1× reaction buffer was prepared which contains 100 mM Tris pH 7.3, 100 mM MgCl$_2$, 1:1000 dilution of a PKA rhodamine-110 substrate (PROFLUOR™ PKA Assay, Promega Corporation, Technical Bulletin 315), and 400 µM ATP; 2) caspase-3 reagent-a 1× reaction buffer was prepared containing 100 mM Tris pH 7.3, 100 mM MgCl$_2$, 150 µg/ml recombinant thermostable luciferase, 80 µM Z-DEVD-aminoluciferin (Promega Corp), 400 µM ATP, 100 µM DTT (Promega Corp), 2.5 mM CaCl$_2$ (Fisher), 40 mM MgSO$_4$ (Fisher), and 0.2% Tergitol NP-9 (Sigma); 3) kinase/caspase-3 combined reagent-a 1× reaction buffer was prepared containing 100 mM Tris pH 7.3, 100 mM MgCl$_2$, 1:1000 dilution of a PKA rhodamine-110 substrate, 150 µg/ml recombinant thermostable luciferase, 80 µM Z-DEVD-aminoluciferin, 400 µM ATP, 100 µM DTT, 2.5 mM CaCl$_2$, 40 mM MgSO$_4$, and 0.2% Tergitol NP-9; 4) protein kinase stop reagent- a 1× stop reagent was prepared containing 100 mM Tris pH 7.3, 100 mM MgCl$_2$, 1:50 dilution of protease reagent (PROFLUOR® PKA Assay), 30 µM staurosporine (BIOMOL Laboratories).

Sample dilutions were prepared in 10 mM HEPES pH 7.5, 0.1% PROPNEX™ (PentaPharma Corp) solution: 0, 1:8000, 1:4000, 1:2000 dilutions of LDH (diamonds); 0, 5, 10, and 20 U/ml caspase-3 (BIOMOL Laboratories, squares), and a combination of LDH/caspase-3 (0/0 U/ml, 1:8000/5 U/ml, 1:4000/10 U/ml, and 1:2000/20 U/ml, respectively, triangles). 100 µl of the dilutions (n=4) were added to white, 96-well plates. The appropriate detection reagent (100 µl) was added to the samples, and the plates were protected from light, mixed for 30 seconds, and incubated at room temperature. Following a six minute incubation at room temperature, fluorescence was measured on a Labsystems FLUOROSKAN ASCENT™ plate reader with filter set 560$_{EX}$/590$_{Em}$. At 45 minutes post-incubation luminescence was recorded using a Dynex MLX plate luminometer.

Results

Figure 8A:
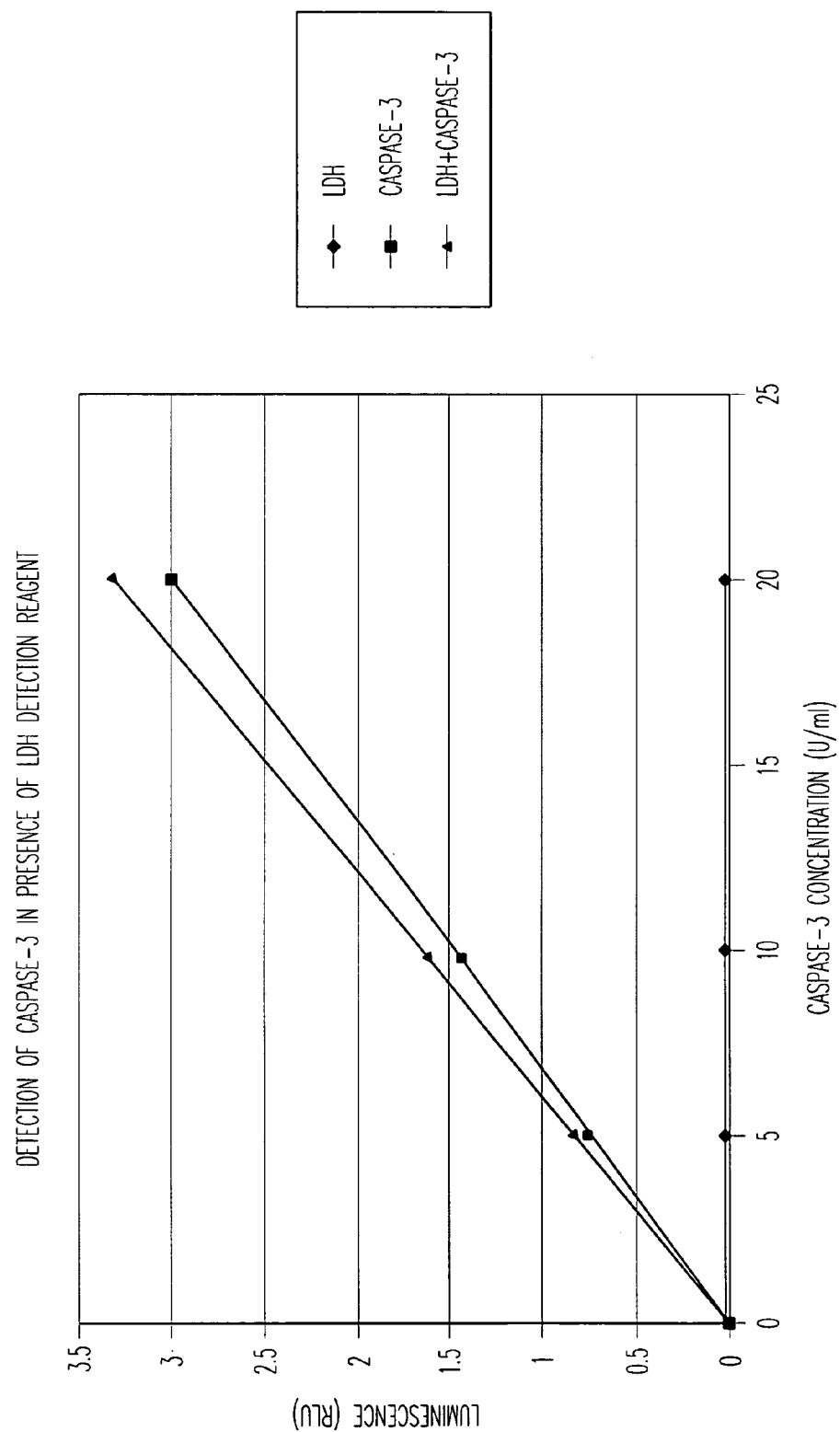
FIGS. 8A-D. Multiplex fluorogenic and luminogenic assays measuring LDH and caspase-3. A) and C) RLU versus caspase-3 concentration. B) and D) RFU versus LDH dilution.
Figure 8B:
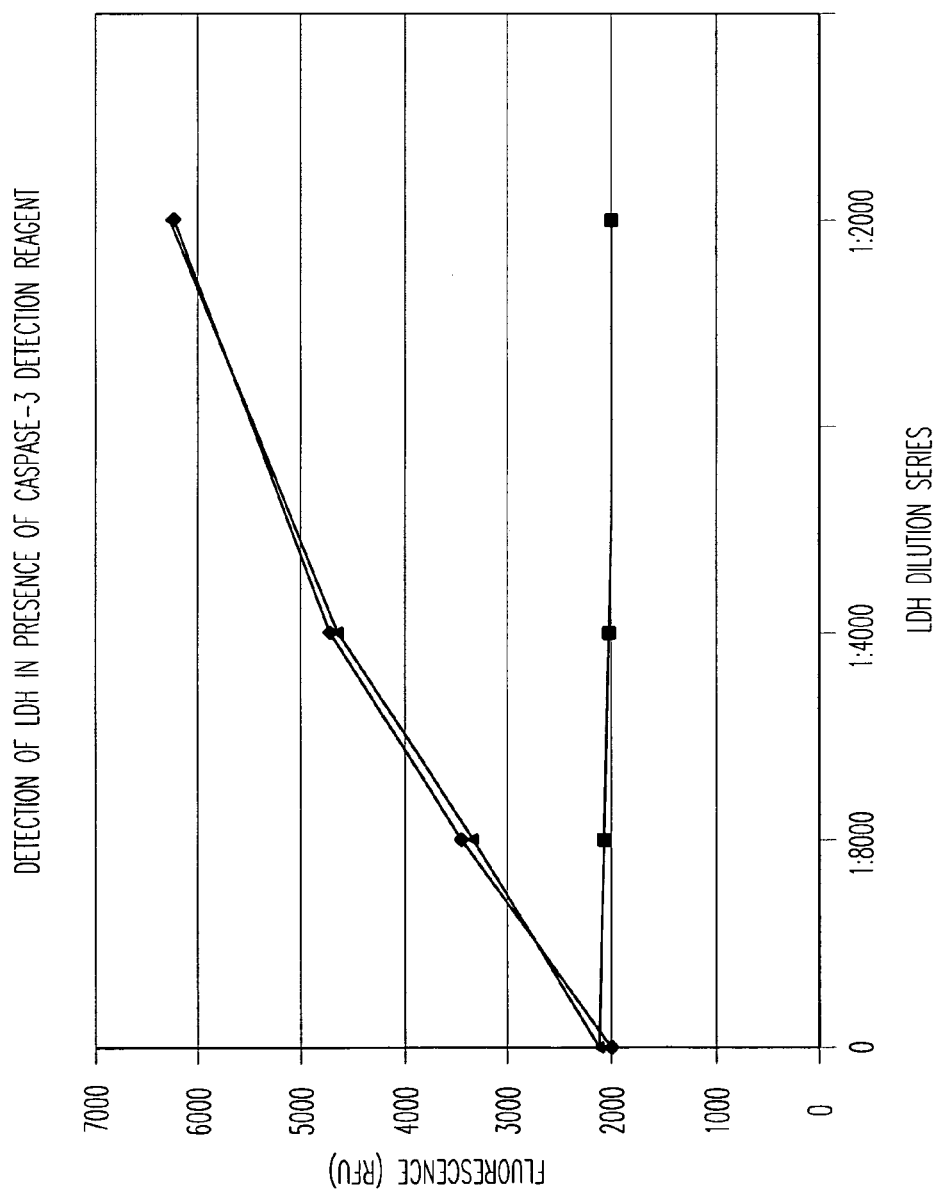
Figure 8C:
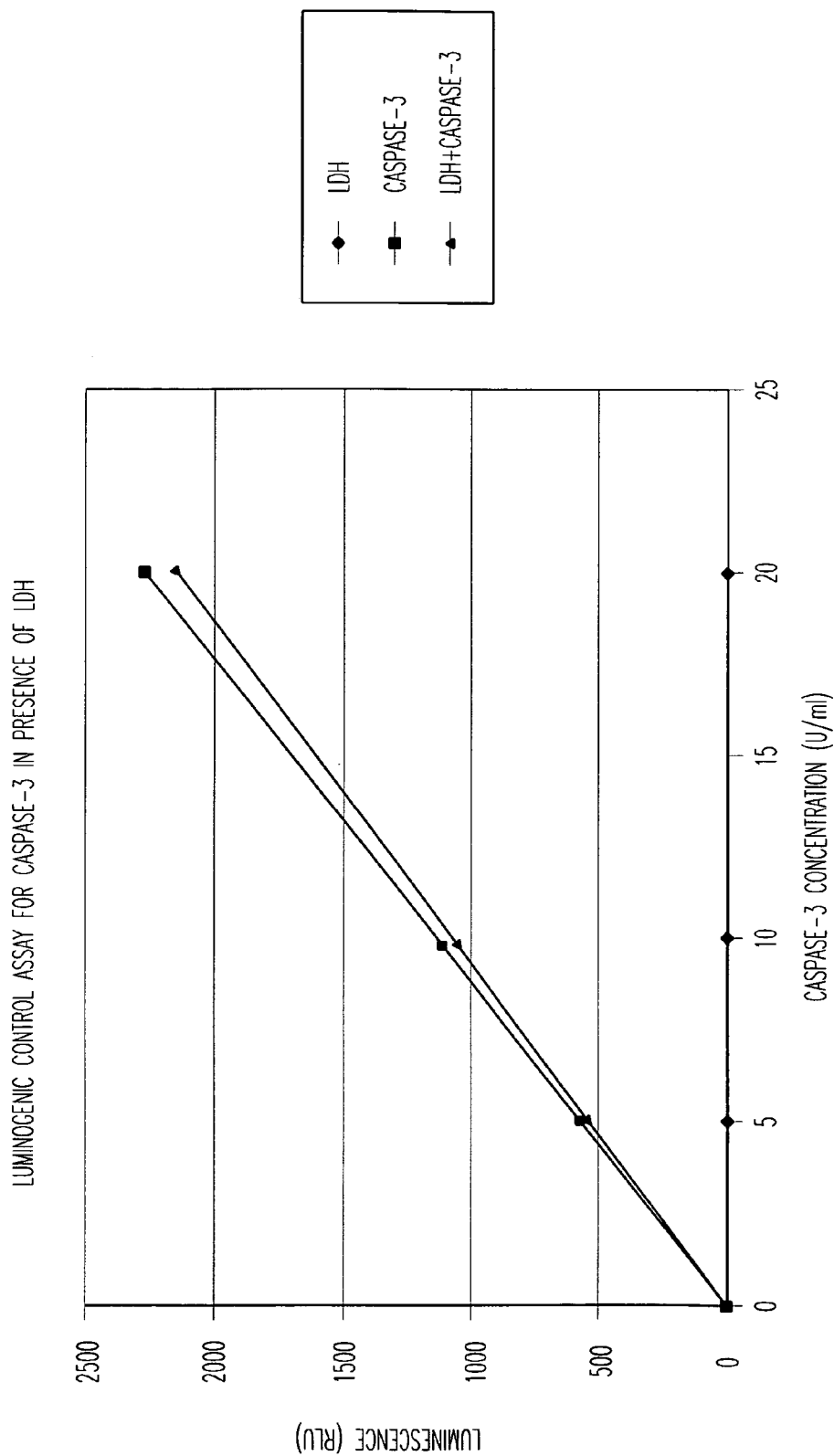
Figure 8D:
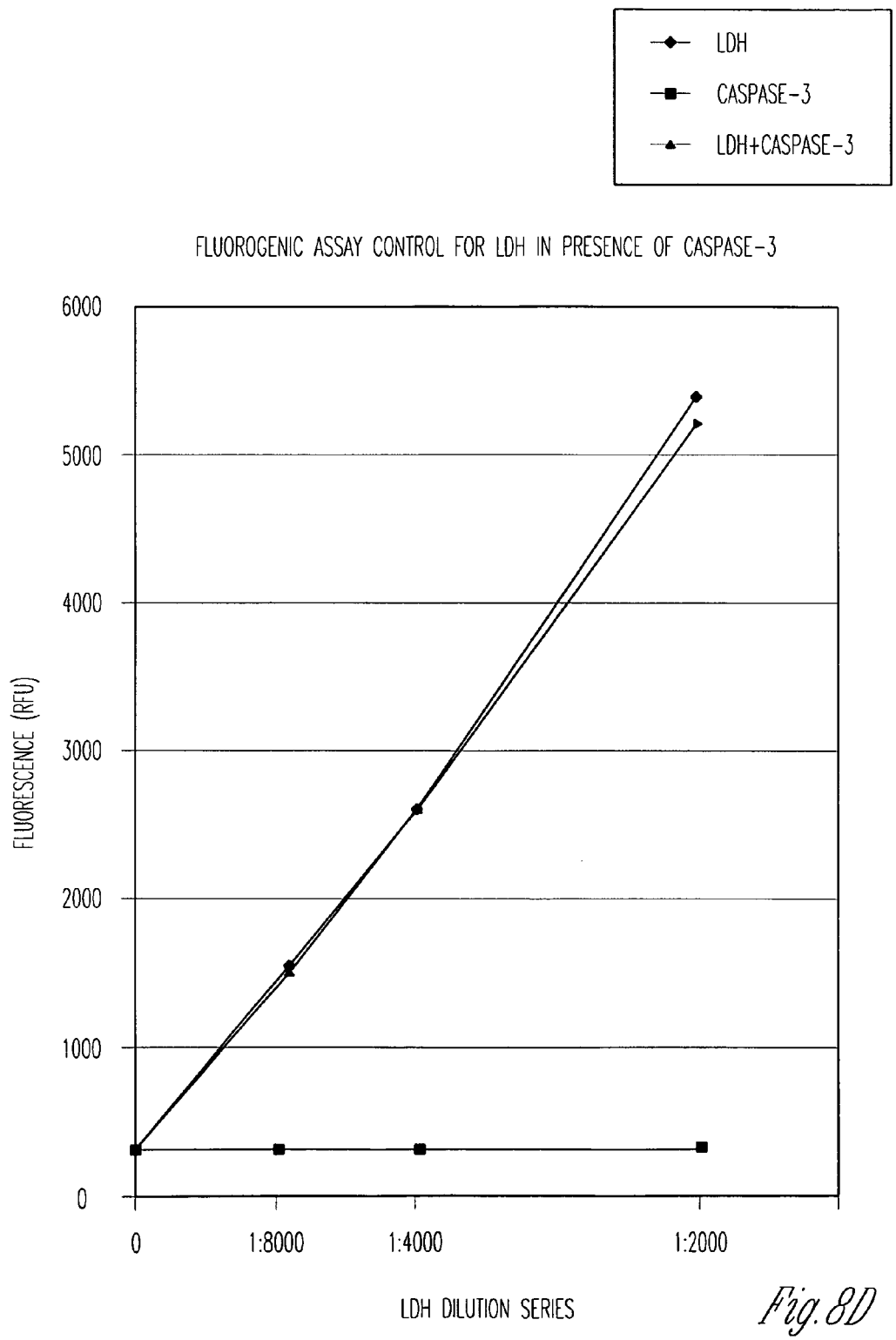

There was a decrease in luminescence with the addition of a fluorogenic LDH detection reagent to a multiplex reaction when compared to a control reaction (FIGS. 8A and 8C, respectively). Despite the decrease in total luminescent signal in FIG. 8A, the luminescent caspase-3 assay was functional in the presence of the fluorogenic LDH detection reagent. FIG. 8B shows there was an increase in fluorescence background when the luminogenic caspase-3 detection reagent was added to the multiplex reaction when compared to control (FIG. 8D); however, FIG. 8A demonstrates the fluorogenic assay for LDH is functional in the presence of the luminogenic detection reagent for caspase-3. There was no contribution of LDH to background luminescence (FIG. 8C), and there was no contribution of caspase-3 to background fluorescence (FIG. 8D).

C. Multiplex Assay for Caspase-3 and Protein Kinase A (PKA) in a Single Well Format The following detection reagents were prepared:1) PKA reagent-a 1× reaction buffer was prepared which contains 100 mM Tris pH 7.3, 100 mM MgCl$_2$, 1:1000 dilution of a PKA rhodamine-110 substrate (ProFluor™ PKA Assay, Promega Corporation, Technical Bulletin 315), and 400 µM ATP; 2) caspase-3 reagent-a 1× reaction buffer was prepared containing 100 mM Tris pH 7.3, 100 mM MgCl$_2$, 150 µg/ml recombinant thermostable luciferase, 80 µM Z-DEVD-aminoluciferin (DEVD corresponds to SEQ ID NO:1) (Promega Corp), 400 µM ATP, 100 µM DTT (Promega Corp), 2.5 mM CaCl$_2$ (Fisher), 40 mM MgSO$_4$ (Fisher), and 0.2% Tergitol NP-9 (Sigma); 3) kinase/caspase-3 combined reagent-a 1× reaction buffer was prepared containing 100 mM Tris pH 7.3, 100 mM MgCl$_2$, 1:1000 dilution of a PKA rhodamine-110 substrate, 150 µg/ml recombinant thermostable luciferase, 80 µM Z-DEVD-aminoluciferin (DEVD corresponds to SEQ ID NO:1), 400 µM ATP, 100 µM DTT, 2.5 mM CaCl$_2$, 40 mM MgSO$_4$, and 0.2% Tergitol NP-9; 4) protein kinase stop reagent-a 1× stop reagent was prepared containing 100 mM Tris pH 7.3, 100 mM MgCl$_2$, 1:50 dilution of protease reagent (ProFluor™ PKA Assay), 30 µM staurosporine (BIOMOL Laboratories).

Sample dilutions were prepared in 10 mM HEPES pH 7.5, 0.1% PRIONEX™ (PentaPharma Corp) solution; 0, 1, 2, and 4 U/ml PKA (diamonds), 0, 5, 10, and 20 U/ml caspase-3 (squares), and a combination of PKA and caspase-3 (0/0 U/ml, 1/5 U/ml, 2/10 U/ml, and 4/20 U/ml, respectively, triangles), and 40 µl of the dilutions (n=4) were added to white, 96-well plates. The appropriate detection reagent (40 µl) was added to the samples, the plates were protected from light, mixed for 30 seconds, and incubated at room temperature for 20 minutes. Following incubation, 40 µl of a protein kinase stop reagent were added to the wells which contained either the kinase reagent alone or the combination kinase/caspase-3 reagent. The plates were mixed an additional 30 seconds, protected from light, and incubated for 30 minutes longer at room temperature. Fluorescence was measured on a Labsystems FLUOROSKAN ASCENT™ plate reader with filter set $485_{EX}/527_{Em}$. Luminescence was recorded using a Dynex MLX plate luminometer.

Results

Figure 9A:
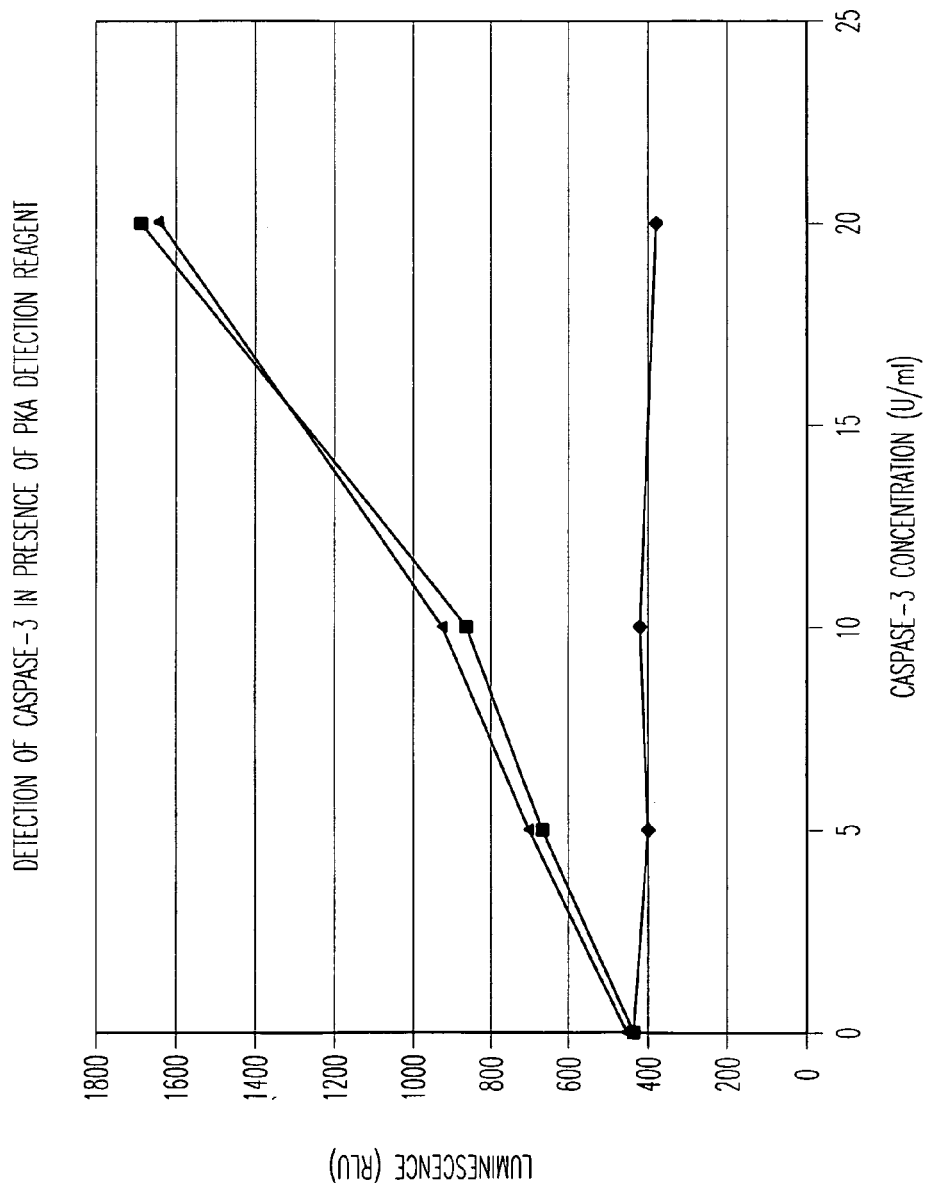
FIGS. 9A-D. Multiplex fluorogenic and luminogenic assays measuring protein kinase A (PKA) and caspase-3. A) and C) RLU versus caspase-3 concentration. B) and D) RFU versus PKA concentration.
Figure 9B:
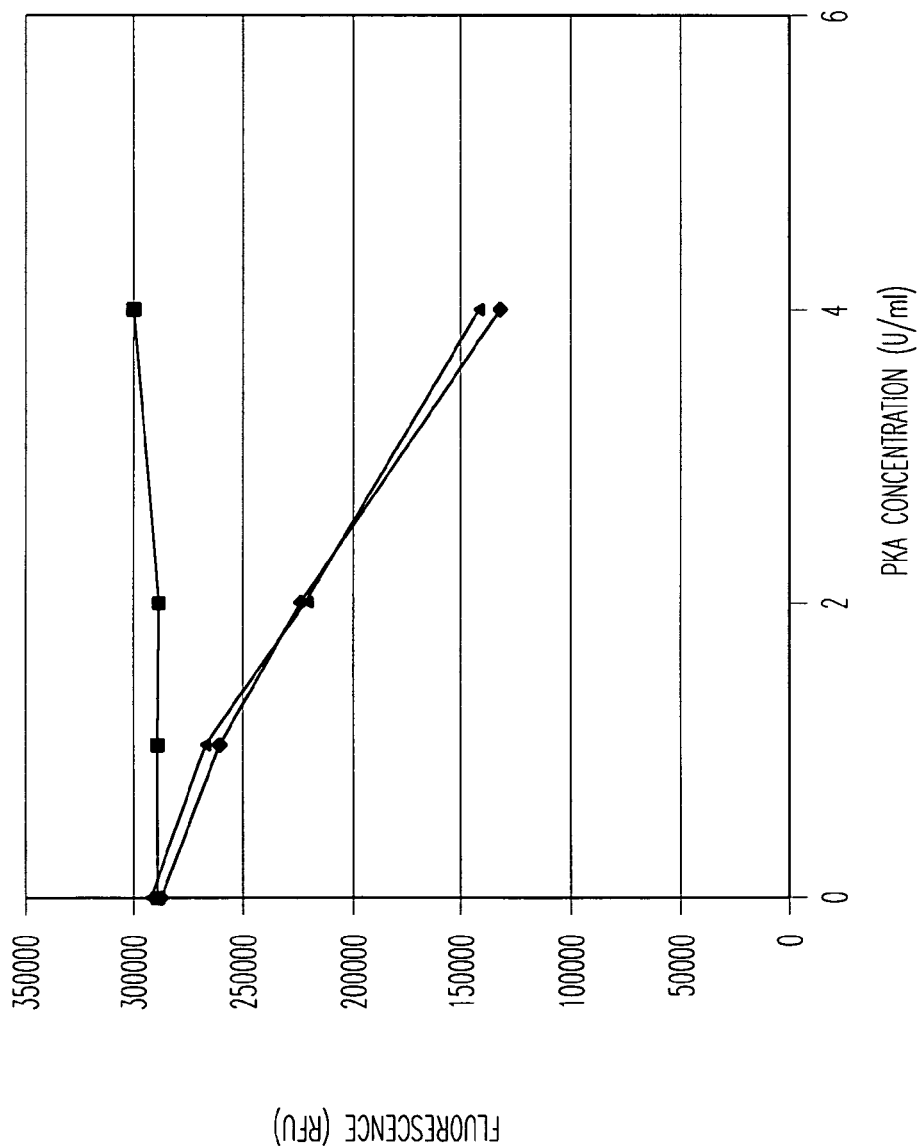
Figure 9C:
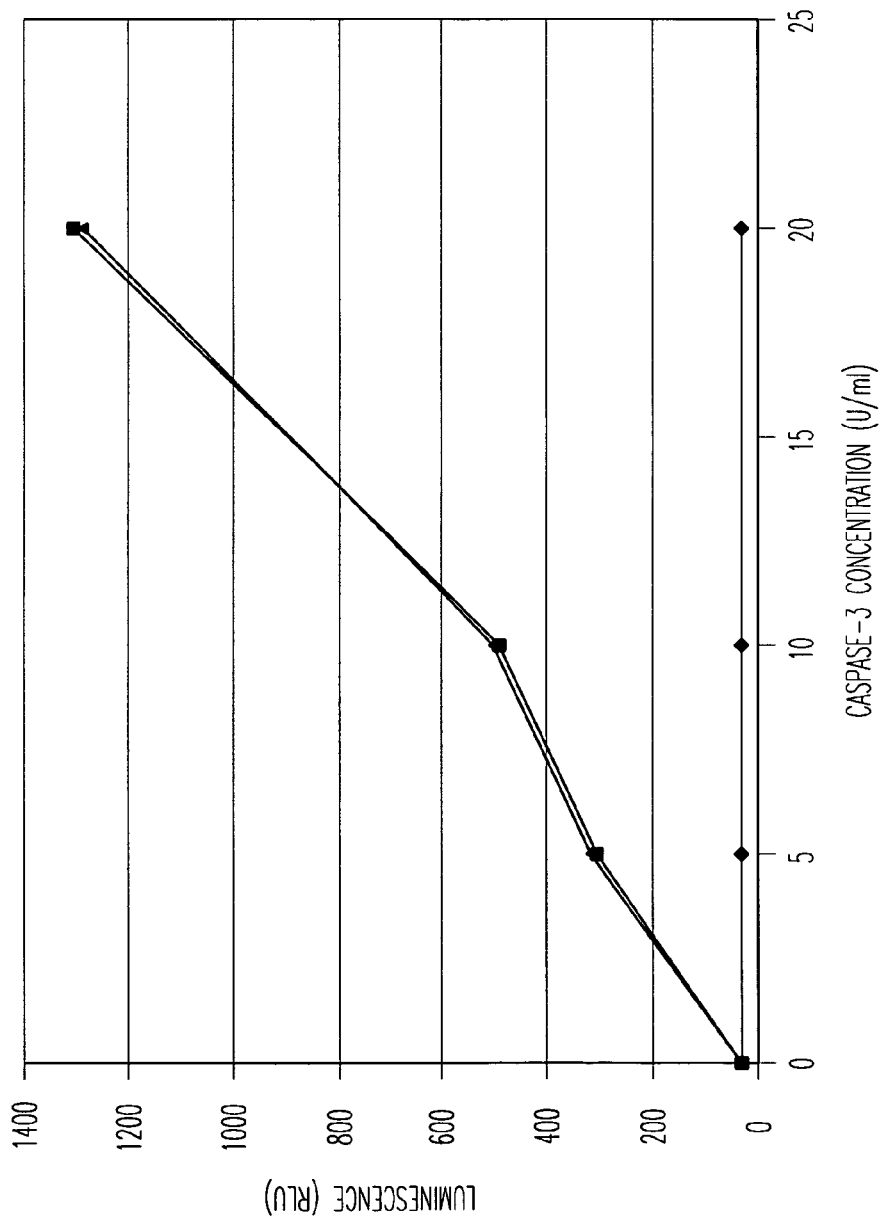
Figure 9D:
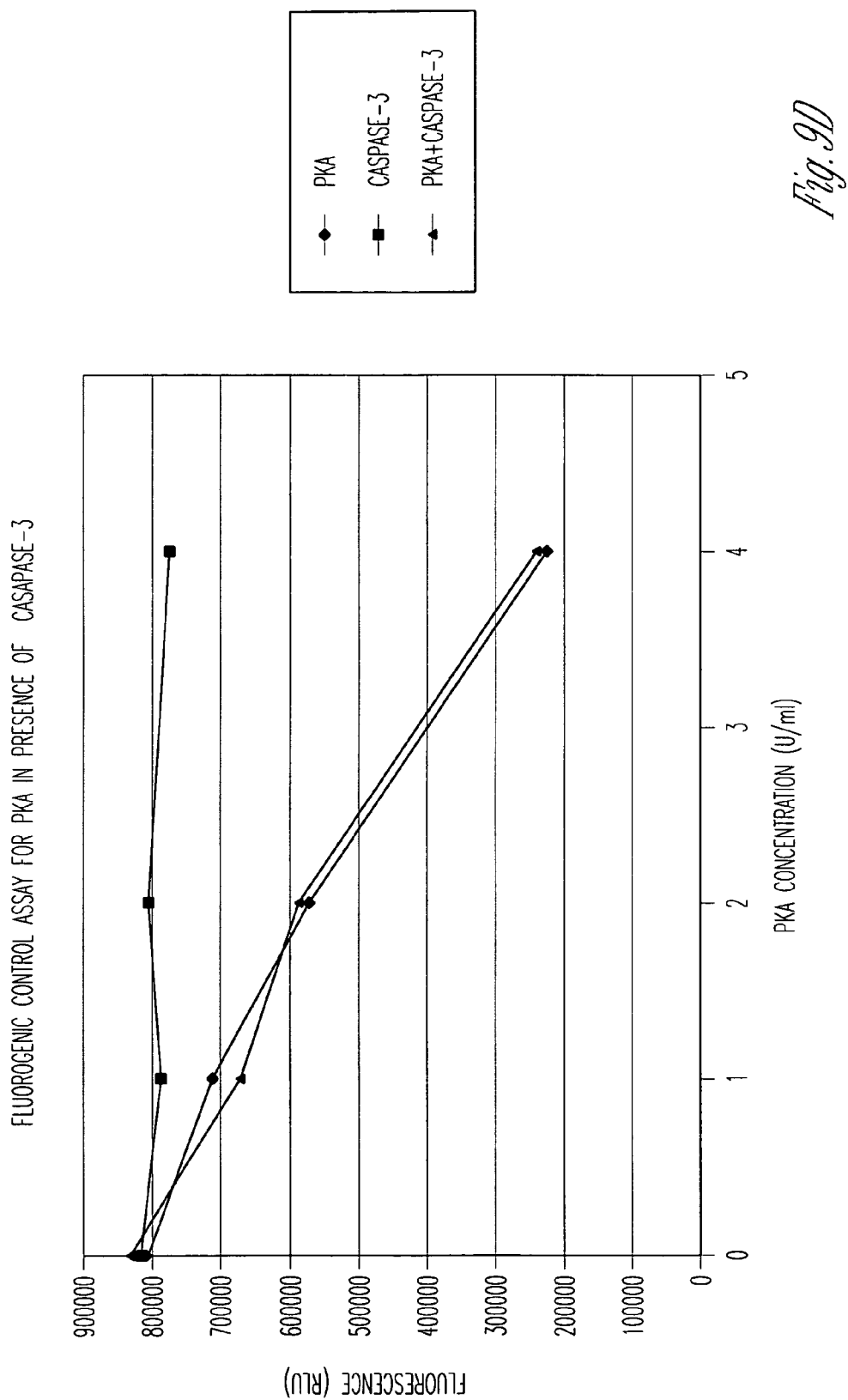

The addition of a fluorogenic PKA assay detection reagent caused the luminescent background to increase (FIG. 9A) when compared to the control reaction where PKA was present but the complete PKA detection reagent was absent (FIG. 9C). However, reaction luminescence resulting from caspase-3 activity increased proportionately and the conditions did not appear to affect the luminogenic caspase-3 reaction itself. Addition of the detection reagent for caspase-3 to the fluorogenic assay for PKA (FIG. 9B) decreased overall fluorescence by more than 50% when compared to the fluorescent control reaction (FIG. 9D) where caspase-3 was present but the complete caspase-3 detection reagent was absent. Caspase-3 and PKA activities were measureable over background using these multiplex conditions.

D. Multiplex Assay for *Renilla* Luciferase and Caspase-3 in a Single Well Format The following detection reagents were prepared:1) EnduRen™ (Promega Corp.), a cell permeant modified coelenterazine substrate for *Renilla* luciferase, was diluted to 600 µM into F-12 tissue culture medium supplemented with 10% fetal bovine serum and 500 µg/ml G-418 sulfate; 2) caspase-3 substrate: (Z-DEVD)$_2$-rhodamine-110 (DEVD corresponds to SEQ ID NO:1) (Promega Corp.) was diluted to 250 µM into F-12 tissue culture medium supplemented with 10% fetal bovine serum and 500 µg/ml G-418 sulfate; 3) luciferase/caspase-3 combined substrates:EnduRen™ (600 µM) and (Z-DEVD)$_2$-rhodamine-110 (DEVD corresponds to SEQ ID NO:1) (250 µM) were diluted in F-12 tissue culture medium supplemented with 10% fetal bovine serum and 500 µg/ml G-418 sulfate.

CHO-K1 cells (ATCC) which stably express *Renilla* luciferase (CHO-K1 hRL25) were maintained in 10% fetal bovine serum and 500 µg/ml G-418 sulfate and used for cell based experiments. Experimental conditions utilizing these cells included: 1) varying levels of luciferase activity due to addition of staurosporine, 2) varying levels of luciferase activity due to staurosporine addition with caspase-3 enzyme addition, and 3) luciferase activity with no staurosporine but with addition of caspase-3 enzyme.

CHO-K1 hRL25 cells were harvested and plated into a 96-well clear bottom, white walled tissue culture plate at a density of 20,000 cells/well, and incubated overnight at 37° C. in 5% CO$_2$. Staurosporine at a final concentration of 0, 0.5, 1, 2 µM (10 µl/well) was added to the appropriate wells to initiate cell death, thus altering luciferase activity. Cells were incubated for an additional 3.5 hours at 37° C. in 5% CO$_2$. Various concentrations of caspase-3 (BIOMOL Laboratories) were added to the appropriate wells at 0, 5, 10, and 20 U/ml, in tissue culture medium (10 µl/well). Therefore, combined staurosporine/caspase-3 concentrations for data points were 0 µM/0 U/ml, 0.5 µM/5 U/ml, 1 µM/10 U/ml, and 2 µM/20 U/ml, respectively. Immediately after addition of the caspase-3 enzyme, 10 µl/well of either luciferase substrate, caspase-3 substrate, or luciferase/caspase-3 substrates were added to the appropriate wells. After addition of the detection reagents, the plates were mixed briefly and incubated at 37° C. in 5% CO$_2$ for two hours. Fluorescence was measured on a Labsystems FLUOROSKAN ASCENT™ plate reader with filter set $485_{EX}/527_{Em}$. Luminescence was recorded using a Dynex MLX plate luminometer.

Results

Figure 10A:
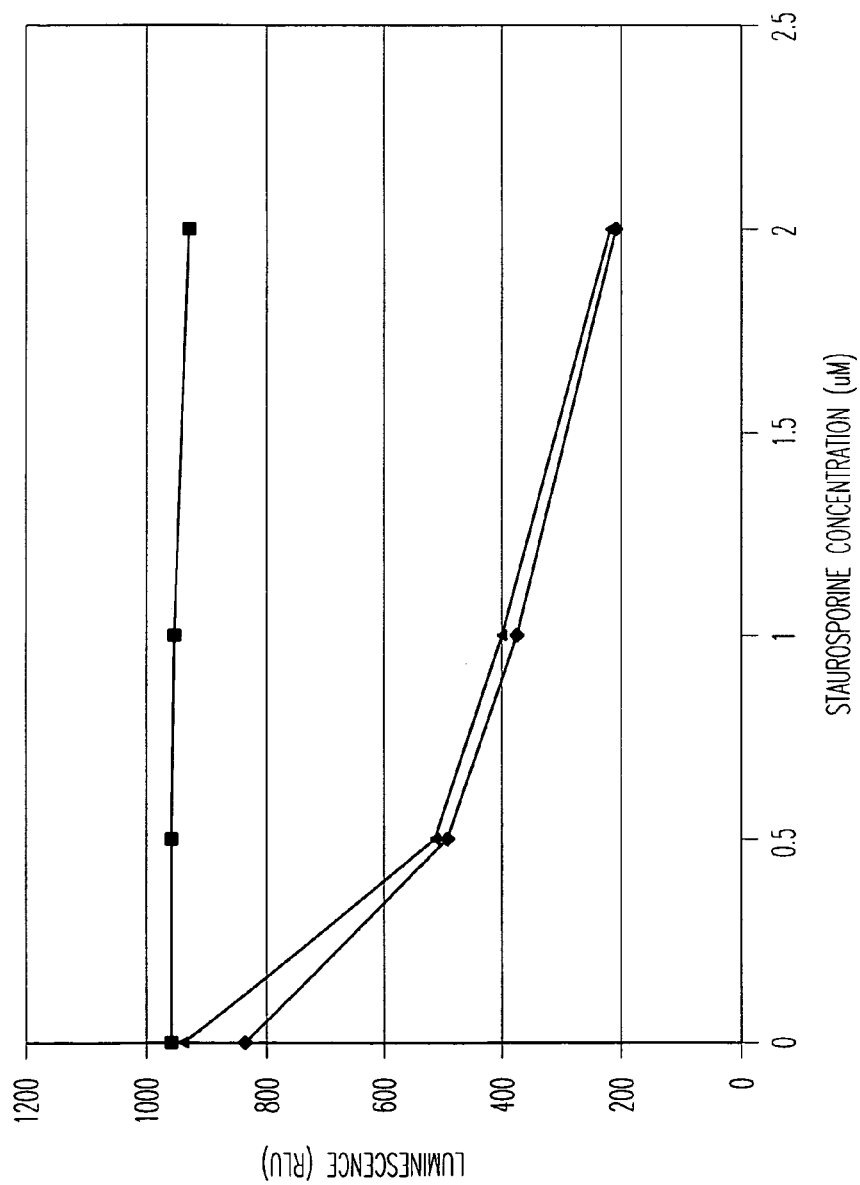
FIG. 10. Multiplex fluorogenic and luminogenic assays measuring caspase-3 and *Renilla* luciferase (luc). A) and C) RLU versus staurosporine concentration. B) and D) RFU versus caspase-3 concentration.
Figure 10B:
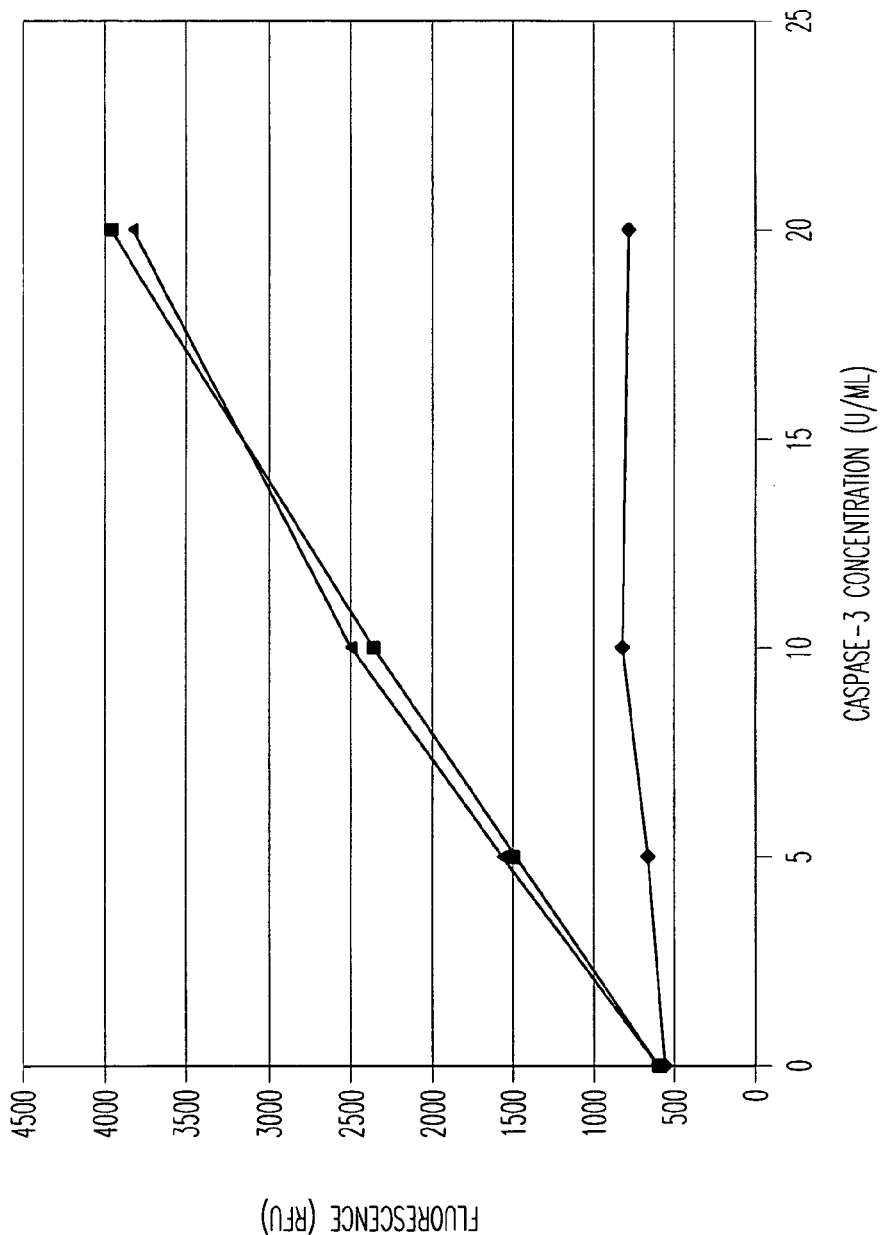
Figure 10D:
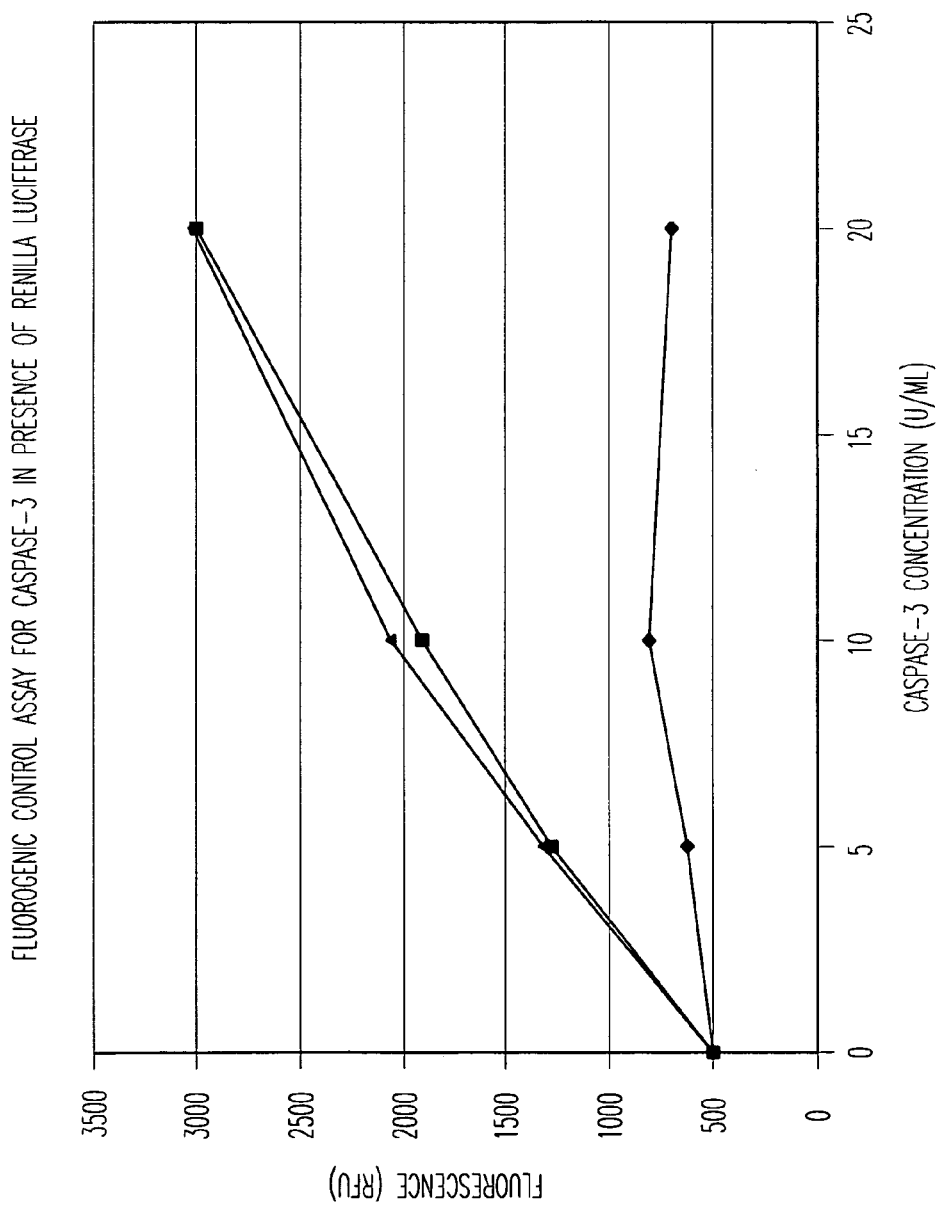

Activity of *Renilla* luciferase was used in these assays as an internal control for cell death. Therefore, as staurosporine concentration increases, luciferase activity should decrease. FIG. 10A shows that the addition of the caspase-3 substrate did not negatively affect the luciferase reaction when compared to the control reaction (FIG. 10C). FIG. 10B shows that the addition of the luciferase substrate had no effect on background fluorescence, even though there was a slight increase in total fluorescence when compared to FIG. 10D. The luminogenic assay for *Renilla* luciferase was fully functional in the presence of caspase-3 or the caspase-3 substrate, and the fluorogenic assay for caspase-3 was only slightly affected, but fully functional, in the presence of *Renilla* luciferase or the *Renilla* luciferase substrate.

EXAMPLE IV

Protease Retention and Release Cell Viability Multiplex Assays

Live cell and dead cell assays are widely used to monitor the change in cellular viability in response to specific chemical, biological or physical treatments. Viability and cytotoxicity assays are generally converse and measure different biomarkers. Methods for assessment of general changes in cell viability by cytotoxicity have historically related to changes in outer membrane permeability. Classical methods of detecting compromised membrane structure include trypan blue exclusion, nucleic acid staining, and lactate dehydrogenase release (Riss et al., 2004; Myers et al., 1998). Assays for the assessment of cell function or proliferation include tritiated thymidine incorporation, ATP content, tetrazolium dye conversion or fluorescein diacetate (Cook et al., 1989). The assumption is that intact cell membranes do not allow bulky charged molecules or peptides to enter from the extracellular space into the cytosol. Conversely, damaged membranes allow free permeability of dyes or compounds into the cell, or cellular contents out of cells. This permeability phenomenon is the basis for both dye labeling ("vital" dyes, DNA intercalators or esterase modified fluoresceins) and LDH release assays.

Whereas, the existing techniques for determining cellular viability remain as useful and cost efficient applications, they have a number of technical or practical drawbacks which limit their utility in high content, multiplexed or high throughput formats. For example, current measures of cellular membrane integrity by LDH release (CytoTox-ONE™) or dye reduction capacity (CellTiter-Blue™) cannot be paired (a means for normalizing the data) due to the shared resazurin substrate and overlapping Ex/Em spectra. Moreover, the colored resazurin substrate utilized in both assays limits $2^{nd}$ assay signal window intensity (and sensitivity) with other endpoint assay measures (color quenching), and the concentrations and formats are not optimized for second assay reagent pairing, e.g., limiting volumes).

Existing live/dead cell formats use carboxyfluorescein and an ethidium homodimer, the latter a known potent mutagen. That format requires washing and substitution of the cell culture medium. Moreover, carboxyfluorescein exhibits spontaneous hydrolysis in aqueous solutions and ethidium homodimer intercalation, which stains DNA, may interfer with downstream data normalization.

Cultured mammalian cells contain a rich milieu of proteases, esterases, lipases, and nucleases. For instance, the four general classes of proteases (aspartic, cysteine, serine, and metal-dependent) are represented and are associated with specific functions of homeostatic maintenance. These cytosolic, lysosomal and transmembrane bound proteases are involved in intracellular protein degradation, generation of immunogenic peptides, posttranslational modification, and cell division (Tran et al., 2002, Constam et al., 1995, Vinitsky et al., 1997). The activity of these enzymes is regulated by various mechanisms including specialized compartmentalization (Bond et al., 1987). In response to extreme stress, environmental adversity, or committed progression of the apoptotic program, a commensurate loss of compartmentalization and membrane integrity is observed (Syntichaki et al., 2003, Haunstetter et al., 1998). Therefore, the release of stable proteolytic mediators into the cell culture medium in in vitro cell models represents a potential surrogate for cell death. Conversely, cytoenzymological staining of retained proteolytic enzymes parallels the phenotypic observation of cell health. Together, such proteolytic activities may help ascertain the relative number of viable or compromised cells in a cell culture population, e.g., a "live/dead" assay.

For protease based live/dead cell assays, in one embodiment, one substrate (for dead cells) is a substrate for a relatively abundant, active and conserved protease that is stable and active at cytosolic pH, e.g., 7.0 to 7.2, and has a label with a spectrally distinct readout (R/O). Preferably, the kinetics of cleavage of that substrate parallels LDH release, and the conditions for activity do not include toxic or membrane altering agents, e.g., salts or thiols, and results in fast assay times. The other substrate (for live cells) is a substrate for a relatively abundant and conserved protease, is cell permeable for viable cells, and the protease is active in a viable cell cytosolic environment but unstable in extracellular environments. That substrate has a label with a spectrally distinct R/O and the cleavage reaction proceeds so as to result in fast assay times. The use of the two substrates in a nondestructive assay can detect undesirable proliferative events and, due to the use of complementary and independent surrogates at different spectra, can reduce erroneous conclusions and reduce errors due to cell clumping or pipetting errors since the viability versus cytotoxicity ratio is independent of cell number variability in that well.

A. Protease Release Assay Formats with AMC or R110 Fluorescence or Aminoluciferin Luminescence Reporters HL-60 cells were two-fold serially diluted then either lysed by the addition Triton X to 0.2% final or maintained by the addition of vehicle. $\frac{1}{10}^{th}$ volume of 200 µM Ala-Ala-Phe-AMC substrate in 100 mM Na Acetate, pH 4.5, was added to the lysates or cells and incubated for an additional hour at 37° C. The fluorescence associated with lysed or viable cells was then measured at Ex. 360 Em. 460 using the CYTOFLUOR™ II.

Jurkat cells undergoing active doubling were counted by trypan blue exclusion and found to be greater than 95% viable. The cells were adjusted to 100,000 cells/ml in RPMI 1640+10% FBS and split into two aliquots. One aliquot was sonicated using a MISONIX™ 3000 equipped with a microtip at 30% power for 3×5 second pulses. The other fraction was incubated in a 37° C. water bath during the sonication procedure (about 5 minutes in total). The cell suspension and lysate fractions were then blended into varying viabilities by ratio mixing representing 0-100% viability. The blended cell samples were then added to a white-walled, clear-bottomed 96 well plate (Costar) in 100 µl volumes. (Ala-Ala-Phe)$_2$-R110 was diluted to 1000 µM in RPMI-1640 and added in $\frac{1}{10}^{th}$ volumes to the plate. The plate was incubated for 30 minutes before measuring fluorescence at Ex 485 Em 530 using a CYTOFLUOR™ II.

Jurkat cells undergoing active doubling were counted by trypan blue exclusion and found to be greater than 95% viable. The cells were adjusted to 100,000 cells/ml in RPMI 1640+10% FBS and split into two aliquots. One aliquot was sonicated using a MISONIX™ 3000 equipped with a microtip at 30% power for 3×5 second pulses. The other fraction was incubated in a 37° C. water bath during the sonication procedure (about 5 minutes in total). The cells solution and lysate fractions were then blended into varying viabilities by ratio mixing representing 0-100% viability. The blended cell samples were then added to a white-walled, clear-bottomed 96 well plate (Costar) in 100 µl volumes. The luminogenic protease release assay reagent was prepared by rehydrating a luciferin detection reagent cake (Promega V859A) with 10 ml of 10 mM Hepes, pH 7.5 and supplementing that reagent with Ala-Ala-Phe-aminoluciferin to 100 µM final concentration. 100 µl of the luminogenic protease release assay reagent was added to the wells of the plate and luminescence measured in kinetic mode using a BMG FLUOstar Optima.

Figure 11A:
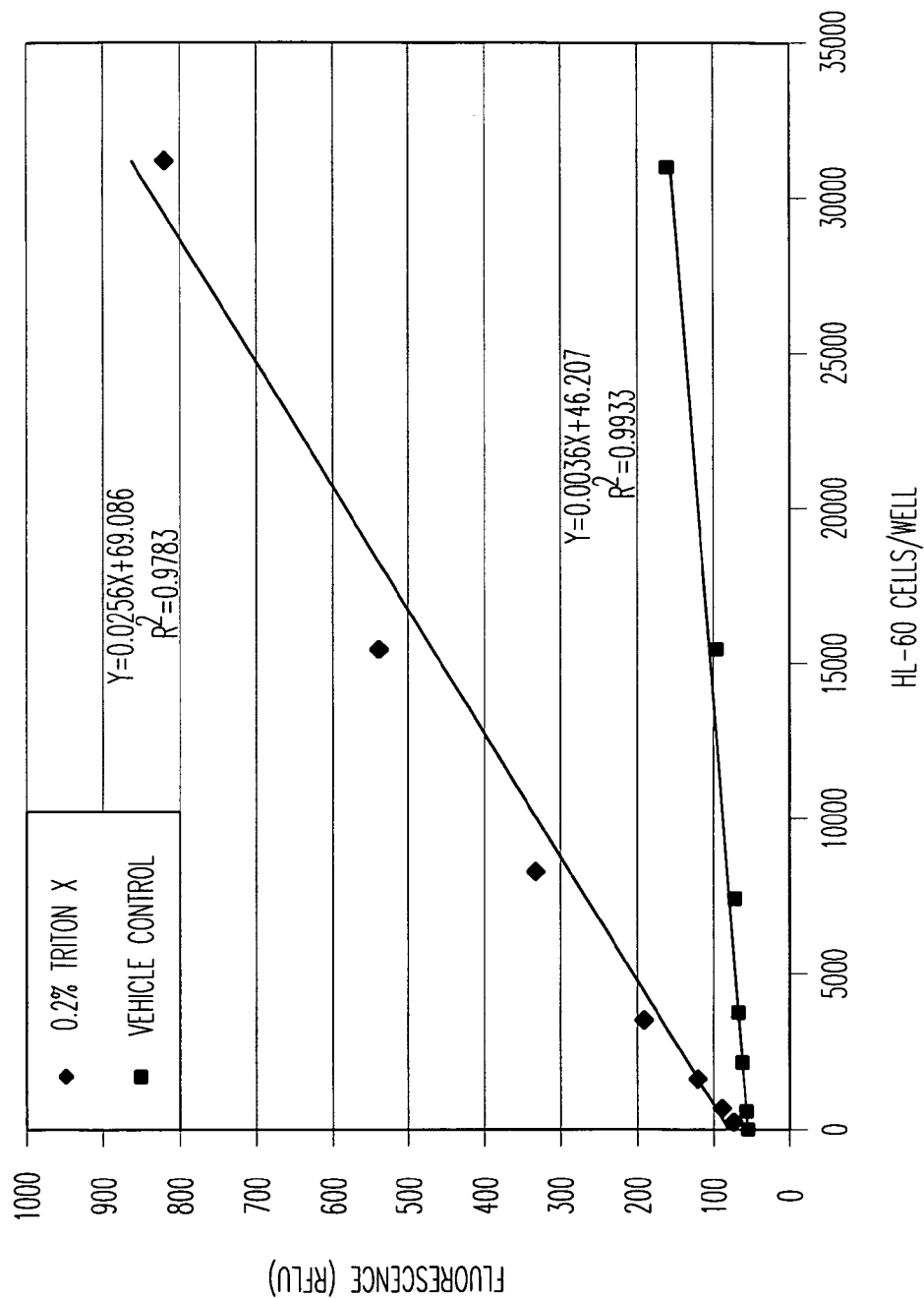
FIG. 11A. Plot of RFLU versus the number of HL-60 cells treated with detergent or vehicle and a protease release assay reagent.
Figure 11B:
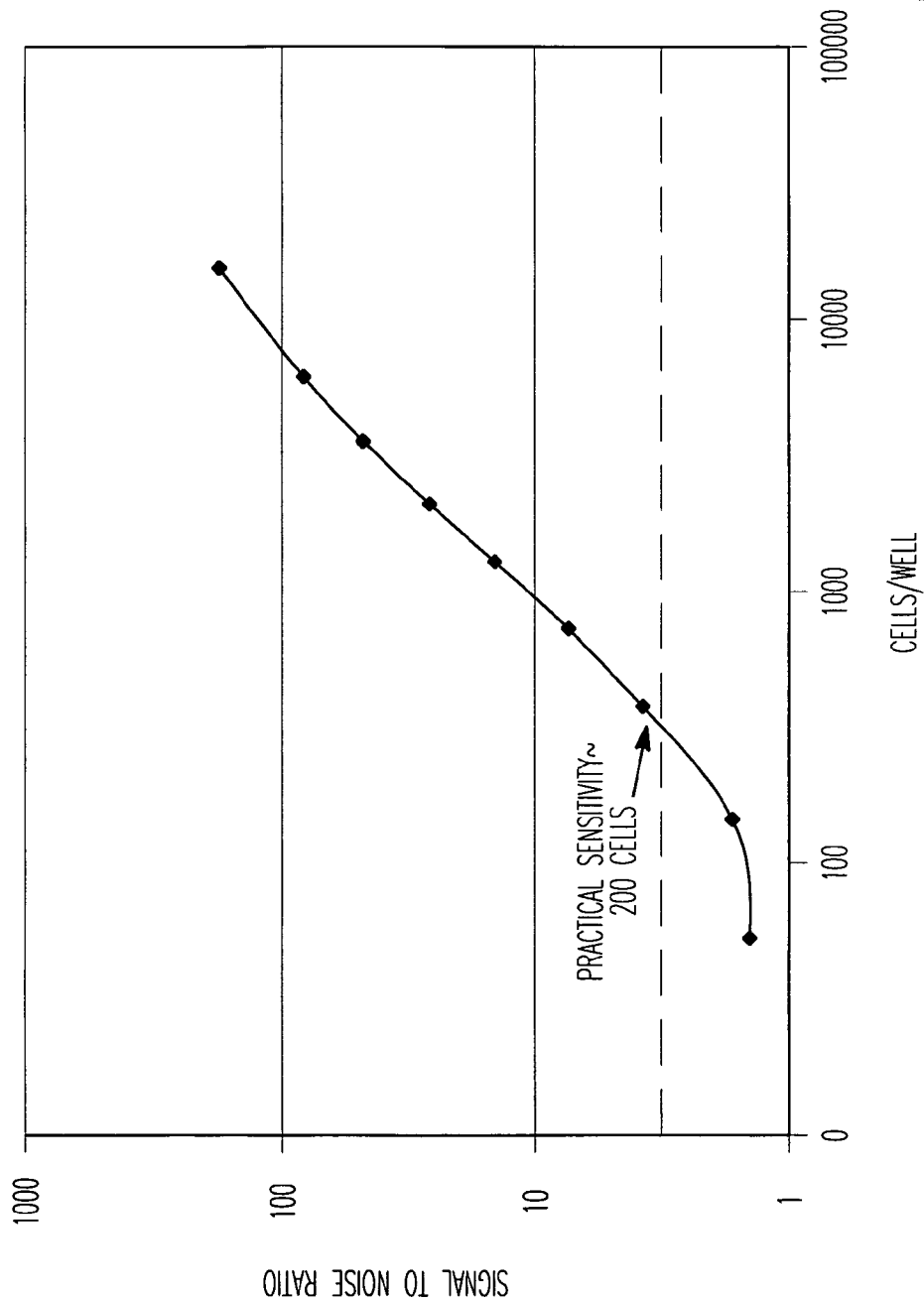
FIG. 11B. Sensitivity of a fluorescent (AMC) protease release assay.
Figure 12A:
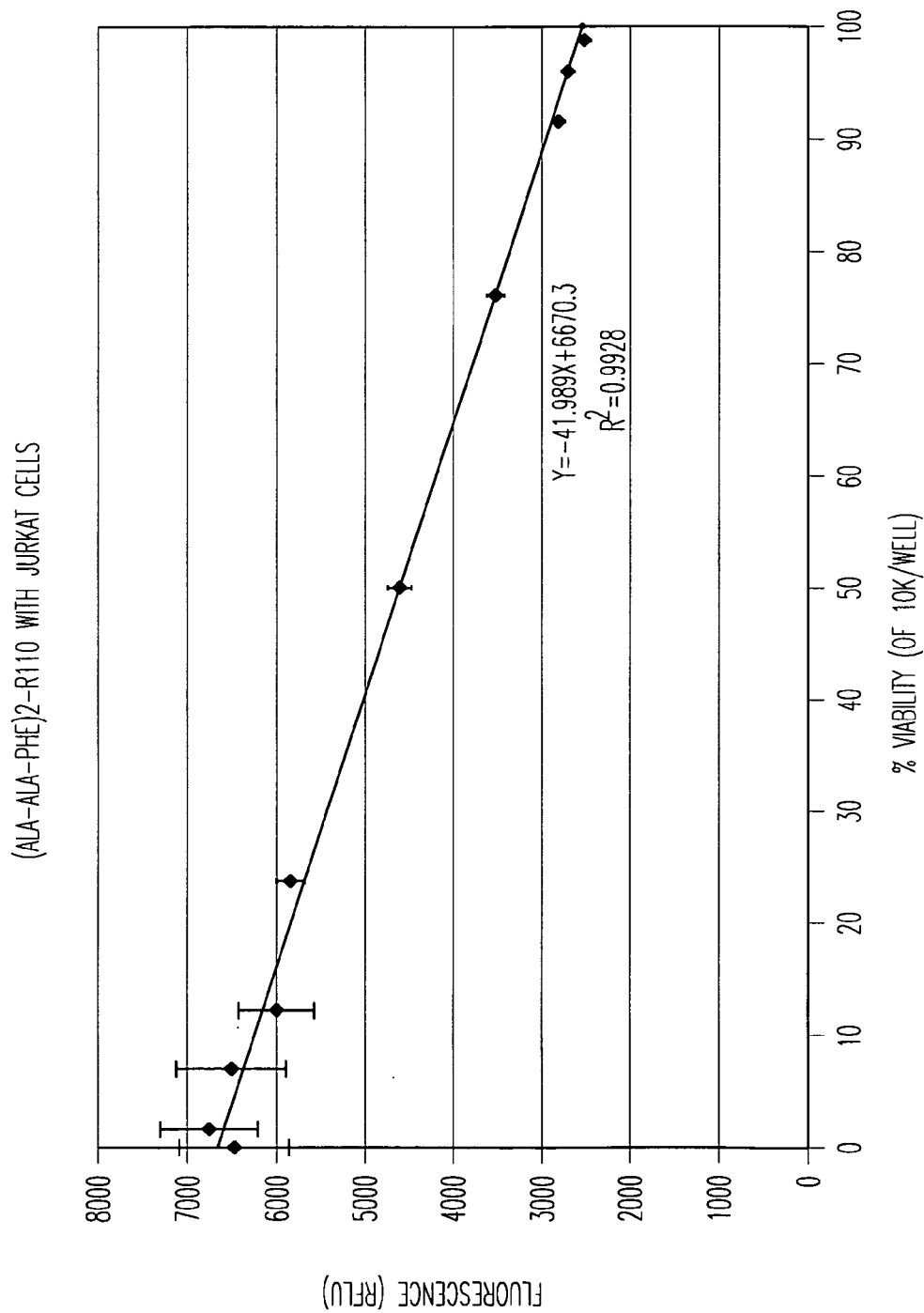
FIG. 12A. Plot of RFLU versus percent viable Jurkat cells treated with a protease release assay reagent.
Figure 12B:
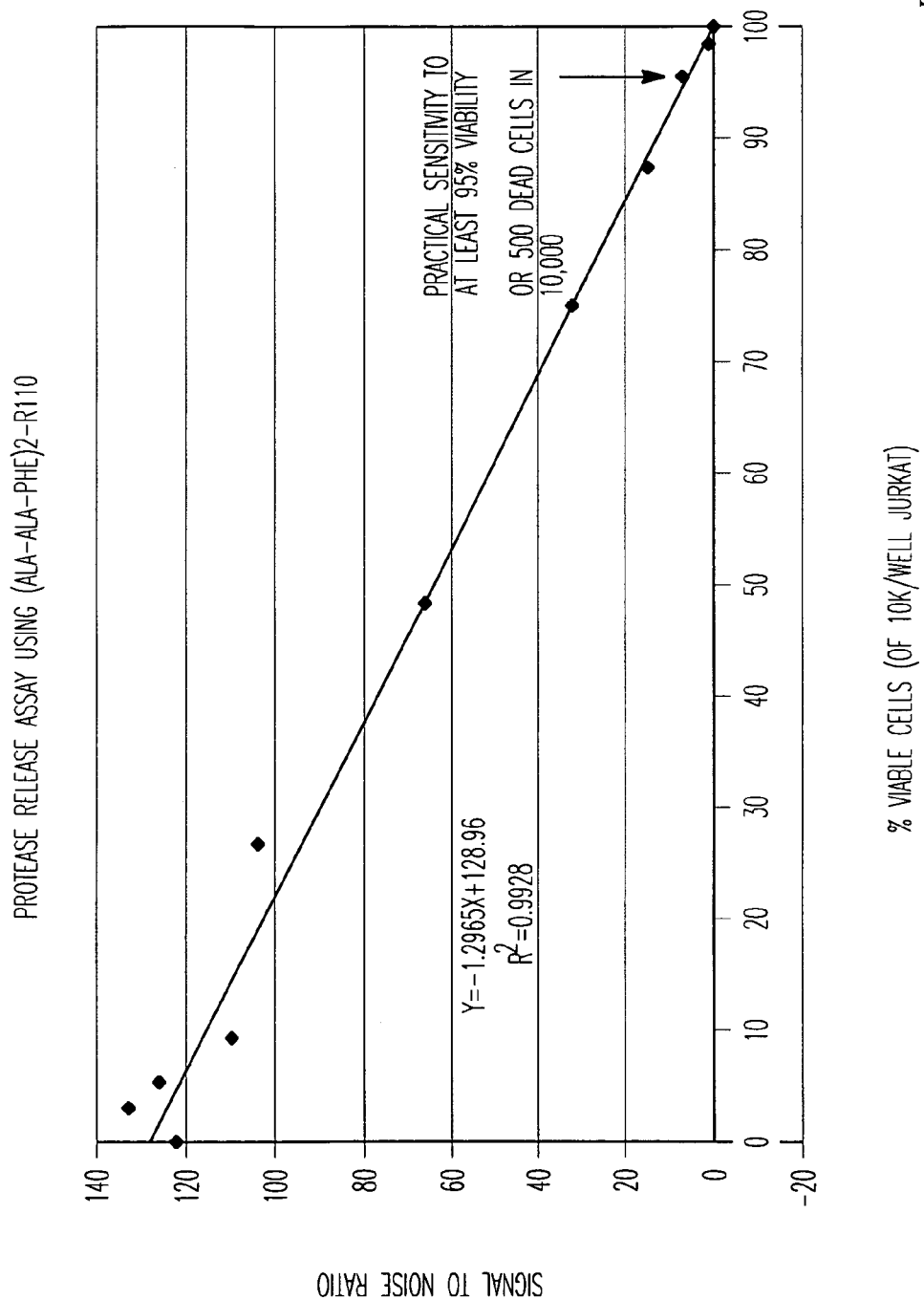
FIG. 12B. Sensitivity of a fluorescent ((Ala-Ala-Phe)$_2$-R110)) protease release assay.
Figure 13A:
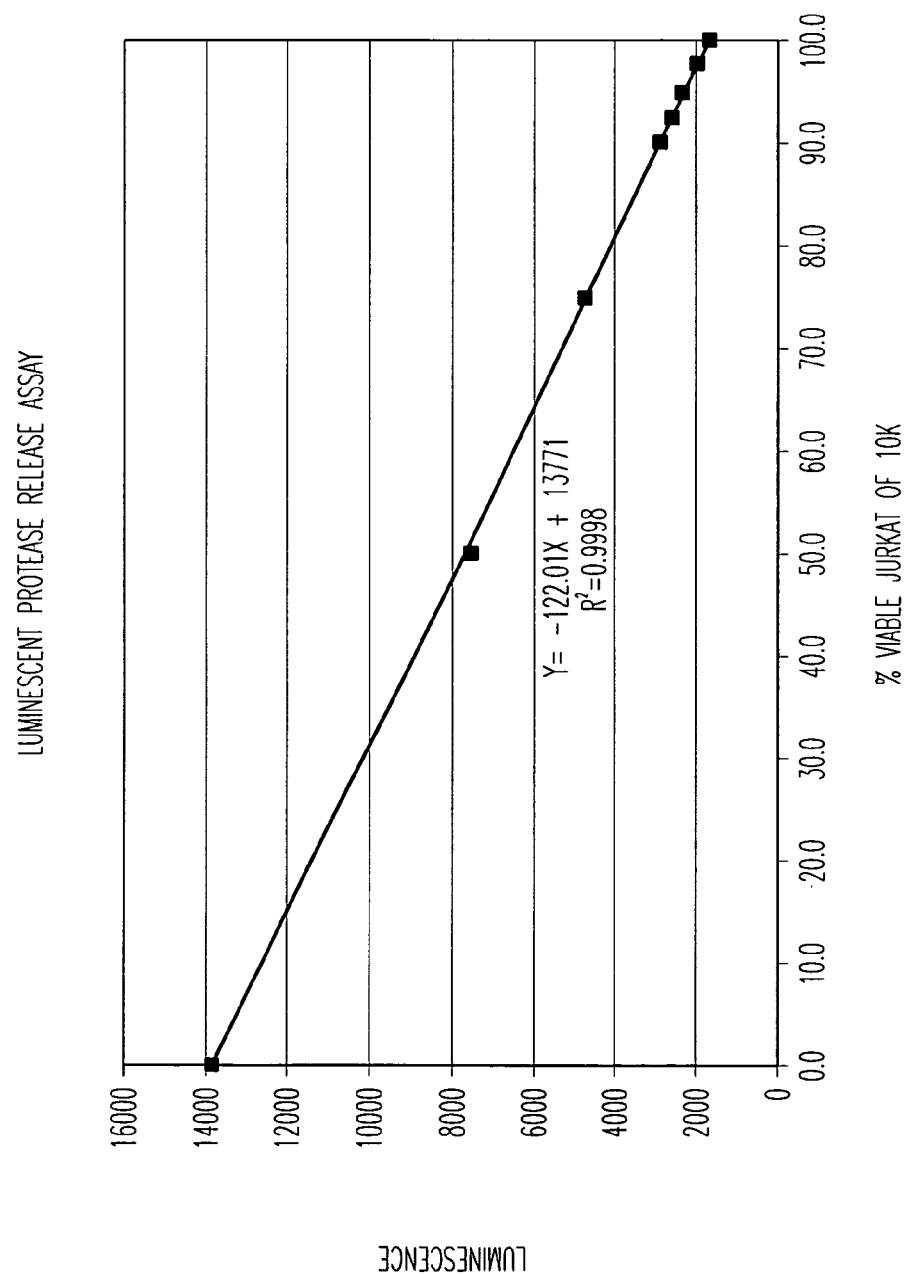
FIG. 13A. Plot of luminescence versus percent viable Jurkat cells treated with a luminescent protease release assay reagent.
Figure 13B:
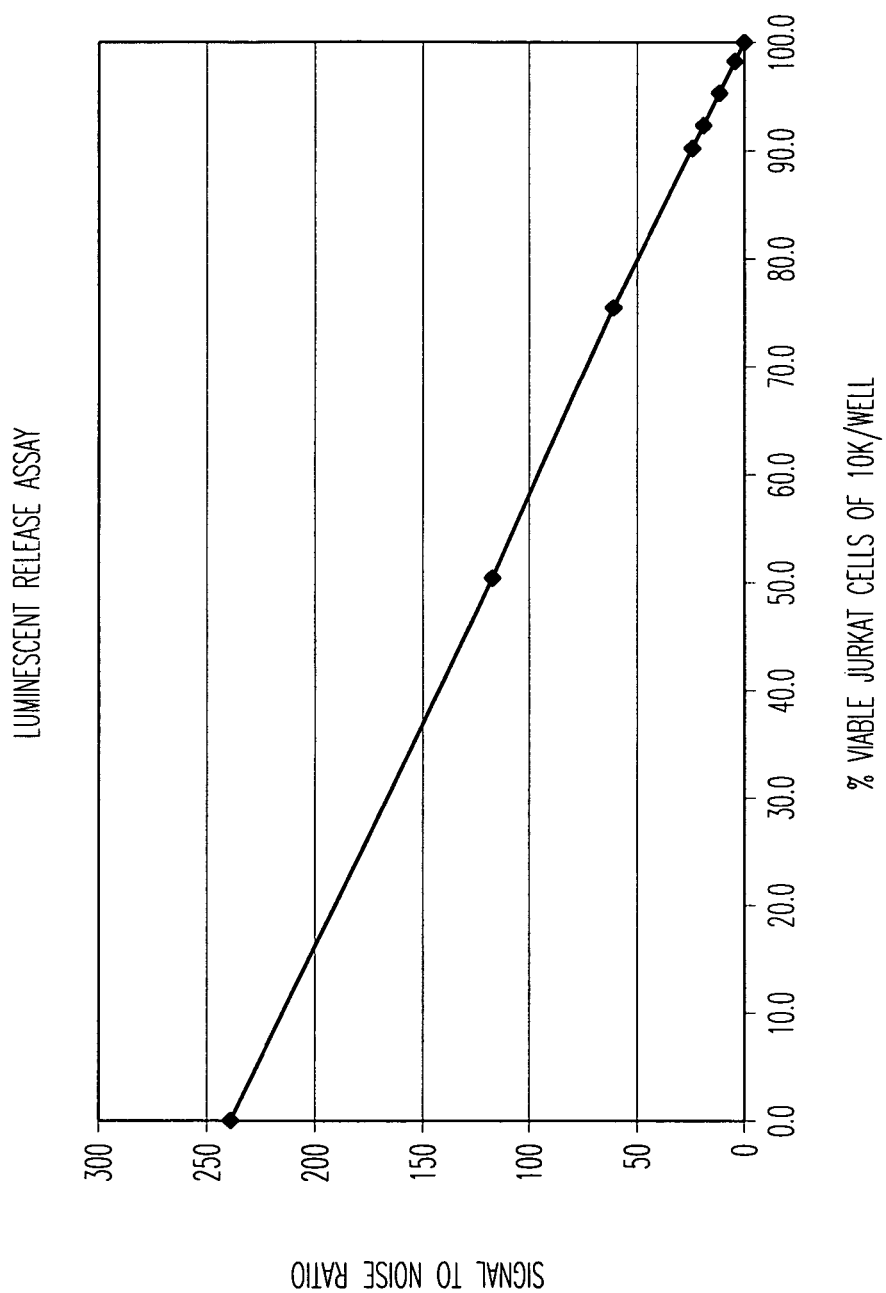
FIG. 13B. Plot of signal to noise ratio versus percent viable Jurkat cells treated with a luminescent protease release assay reagent.

The practical sensitivity of the AMC fluorescent format was calculated to be about 240 cells (FIG. 11), a sensitivity value comparable to CytoTox-ONE™. The R110 format (FIG. 12) of the assay was similarly sensitive providing yet another fluorophore for multiplexing applications. Notably, the sensitivities from these assays were obtained without fluorescence quenching, a major obstacle for use of CytoTox-ONE™ or other resazurin-based assays in downstream multiplex applications. The exquisite linearity and range of the luminescent format (FIG. 13) allowed for statistical detection of as few as 200 cells in a population of 9800 viable cells. The non-lytic luminescent format offers another alternative for cytotoxicity detection.

B. Protease Release Assay Formats with Different Enzyme Targets

Actively doubling HL-60 cells were adjusted to 100,000 cells/ml and split into two aliquots. One aliquot was sonicated using a microtip MISONIX™ 3000 with 30% power for three 5 second pulses. The other aliquot was held at 37° C. The cell suspension and lysates were then two-fold serially diluted in RPMI 1640+10% FBS in 100 µl volumes. Medium only served as the no cell contol. A luciferin detection reagent cake (Promega V859A) was resuspended with 2.0 ml of 10 mM Hepes, pH 7.5. The luciferin detection reagent was then divided and made 1 mM with either Z-Leu-Leu-Val-Tyr-aminoluciferin (LLVY corresponds to SEQ ID NO:18) or Ala-Ala-Phe-aminoluciferin. Each reagent was added to independent replicates of the plate in $\frac{1}{10}^{th}$ volumes and allowed to incubate for 15 minutes at 37° C. in the Me' Cour thermal jacketed water bath holder before luminescence measurement using the BMG FLUOstar Optima.

Figure 14A:
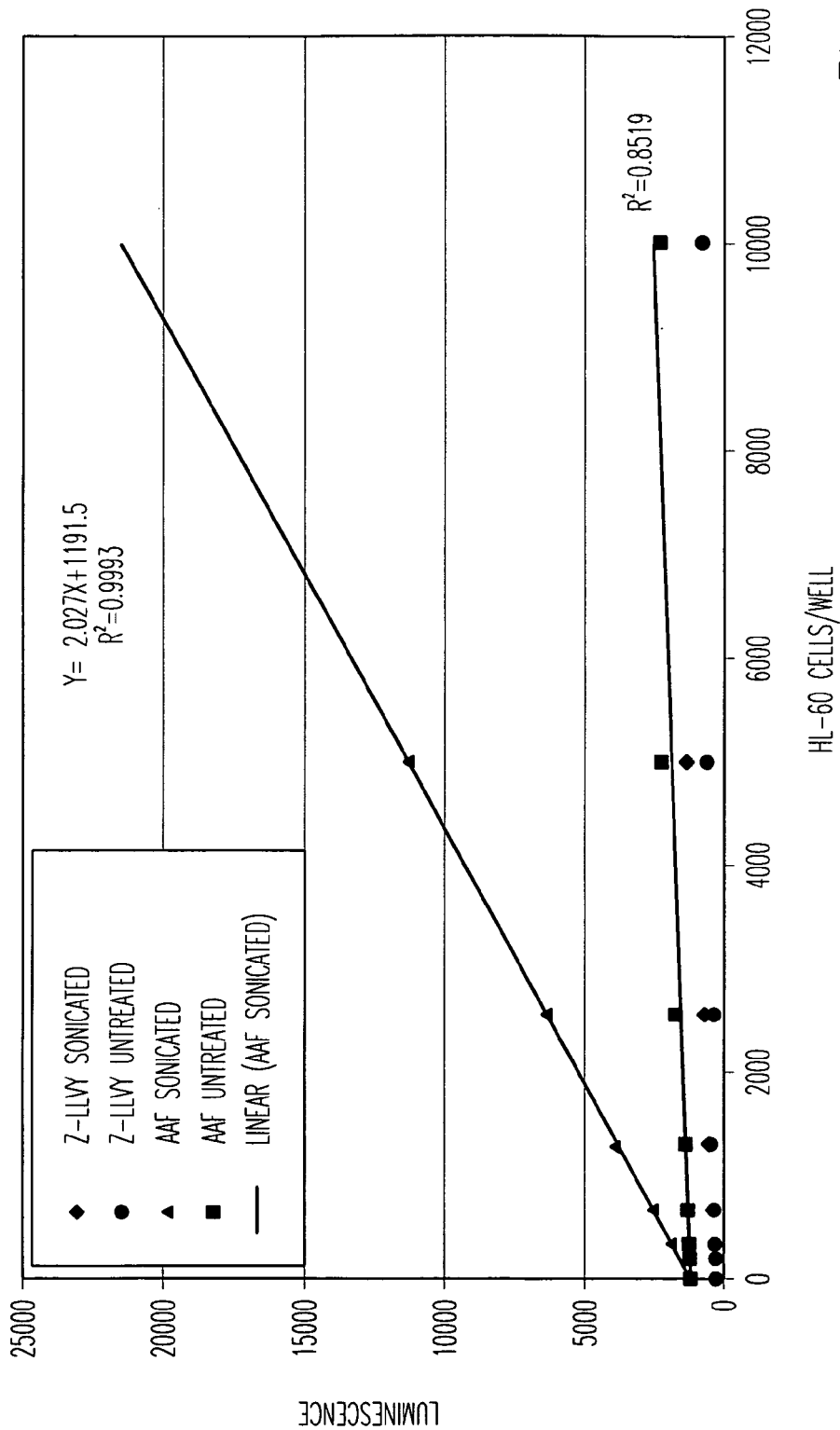
FIG. 14A. Plot of RLU versus number of HL-60 cells treated with different protease release assay reagents and with or without sonication (SEQ ID NO:18).
Figure 14B:
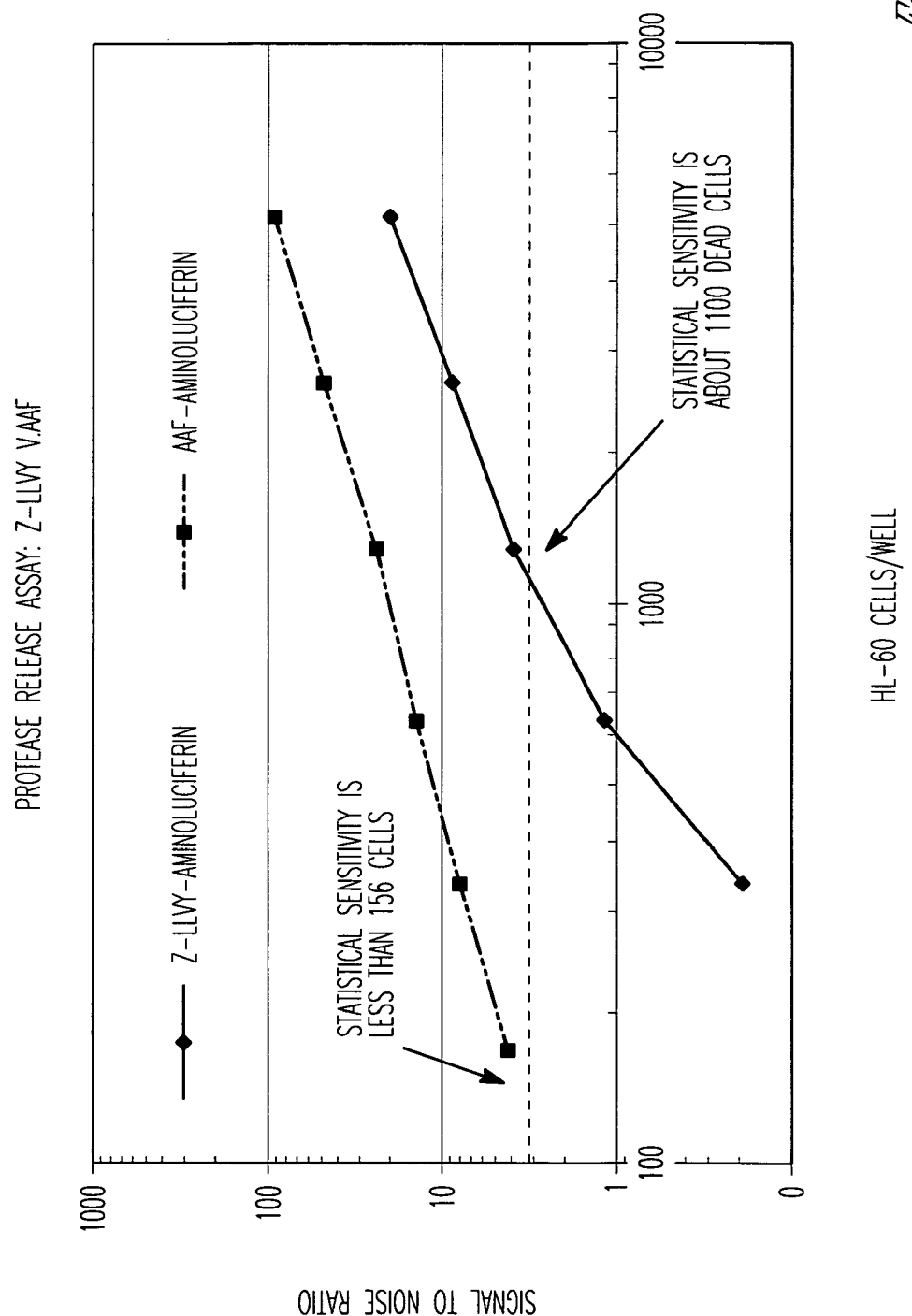
FIG. 14B. Sensitivity of a luminescent protease release assay with different substrates (SEQ ID NO:18).

Although the Z-LLVY-aminoluciferin (LLVY corresponds to SEQ ID NO:18) assay performed less optimally than the AAF-aminoluciferin sequence, it demonstrated that other proteases can be used as surrogates of compromised integrity (FIG. 14). In this case, LLVY (SEQ ID NO:18) activity may be attributable to the chymotryptic activity of the proteosome.

C. Protease Release Time Course

HL-60 cells (25,000/well) were treated with 10 µM staurosporine or matched DMSO vehicle control over a 7 hour time course at 37° C. with 5% $CO_2$ in a clear bottomed, white walled 96-well plate (Costar). A 200 µM Ala-Ala-Phe-AMC substrate solution was created in 100 mM Na Acetate, pH 4.5. A 10 µl volume of the substrate ($\frac{1}{10}^{th}$ volume of the sample) was added to the wells and incubated for an additional hour. "Protease release" activity was measured at Ex. 360 Em. 460 on a CYTOFLUOR™ II. In a parallel set of wells, CytoTox-ONE™ reagent acted as the membrane integrity assay control. The reagent was added 10 minutes prior to measurement of fluorescence at Ex. 560 Em. 580.

Figure 15A:
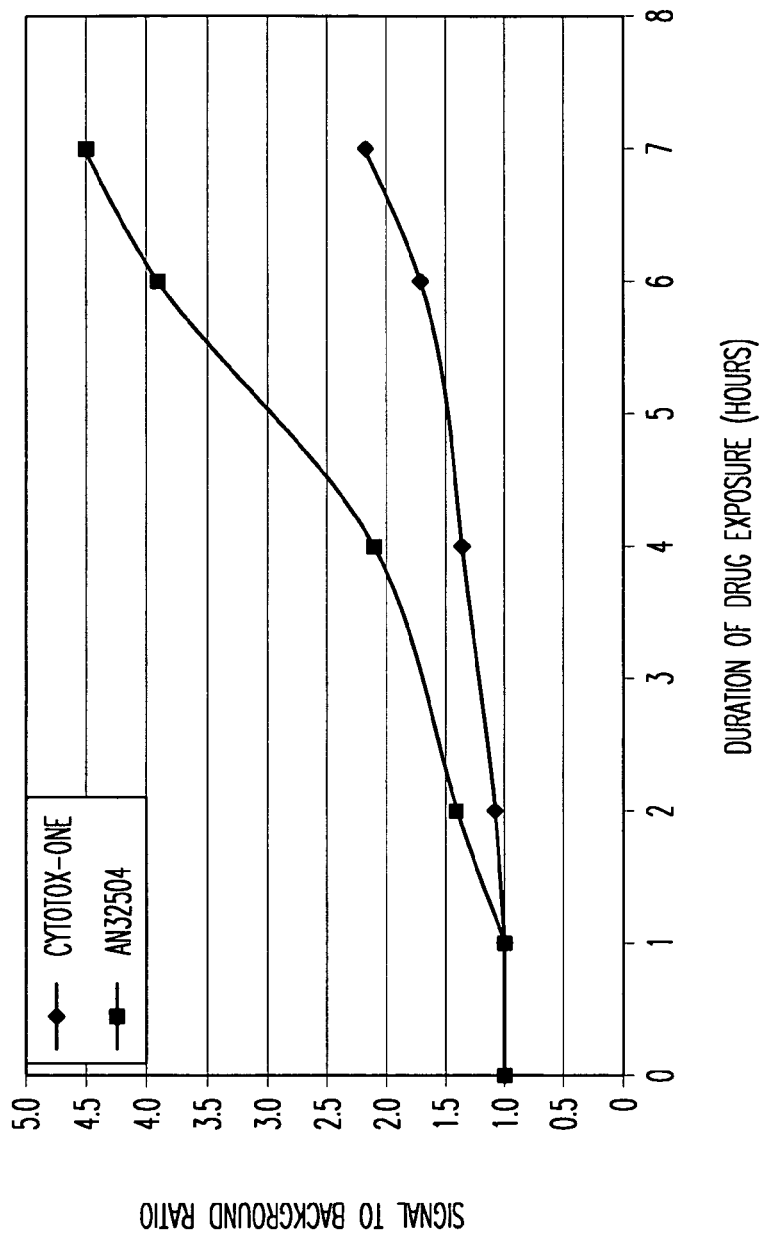
FIG. 15A. Plot of signal to background ratio versus time of staurosporin exposure in a protease release (cell death) assay (AN32504) and a CytoTox-ONE™ assay.
Figure 15B:
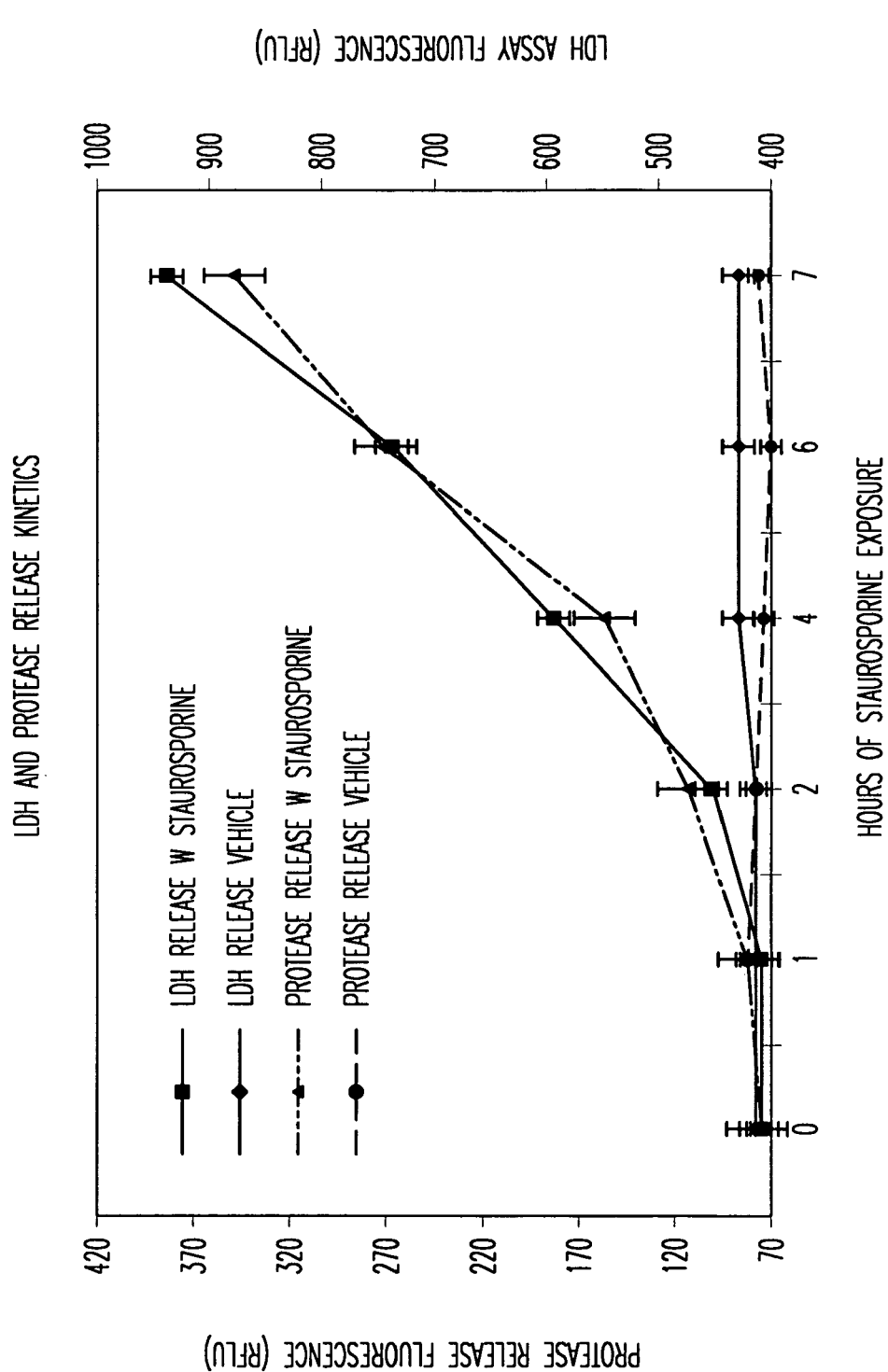
FIG. 15B. Plot of RFLU versus time of staurosporin exposure versus LDH release.

The kinetics of cell permeability, i.e., LDH and protease release, mirrored each other and were consistent with the morphological observation of secondary necrosis in the cell populations (FIG. 15). Presentation of the aminopeptidase substrate in an acidic Na Acetate formulation (final pH in sample about 6.5) was conducted to accommodate potential lysosomal protease activities.

D. Protease Release Activity pH Requirements

The pH requirement of the protease release activity was explored using 100 mM Na Acetate adjusted to pH 2.5, 3.5, and 4.5 and compared to non-adjusted culture medium (water vehicle). Ala-Ala-Phe-AMC was added to 200 µM in these buffers. A $\frac{1}{10}^{th}$ volume of the solutions was added to the plate and mixed briefly by orbital shaking. The plate was incubated for 40 minutes at 37° C., then fluorescence measured at Ex. 360 Em. 460 using the CYTOFLUOR™ II.

Figure 16:
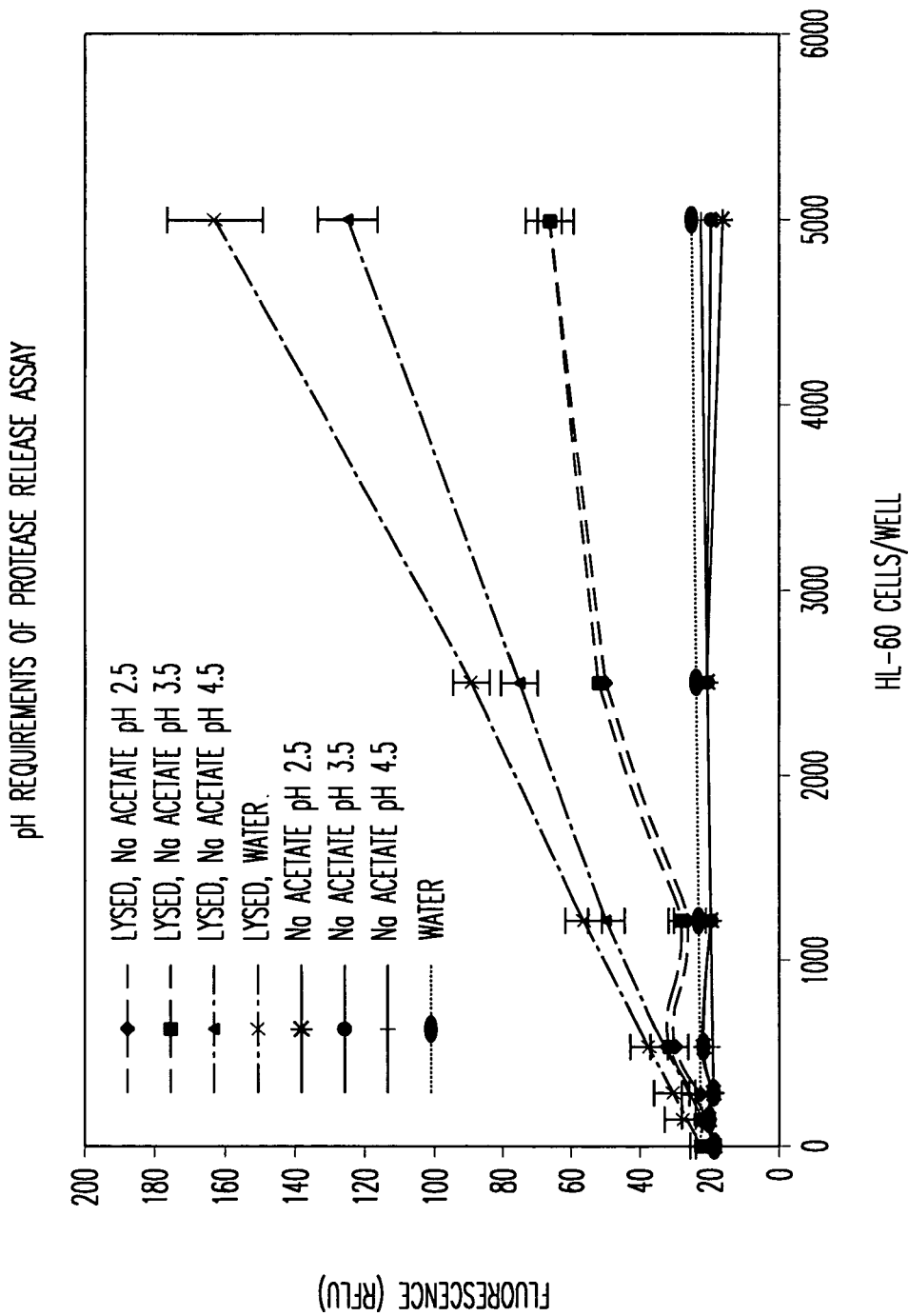
FIG. 16. Plot of RFLU versus number of HL-60 cells treated with a protease release assay reagent, with or without lysis and at different pHs.

Addition of $\frac{1}{10}^{th}$ volume of Na Acetate, pH 4.5 reduced the culture media to a final pH of about 6.5. The final pH of other lower pH solutions/medium combinations were not tested but previous experimentation suggested that adding $\frac{1}{10}^{th}$ volume of pH 2.5 Na Acetate reduced cell medium pH to about 5.5. It was found that the non-pH adjusted vehicle proved to be the most favorable for protease release activity (FIG. 16). This activity is consistent with a cytosolic aminopeptidase and probably not a lysosomal protease (cathepsins etc.). This is significant because no detrimental or potentially cytotoxic adjuncts are required to measure protease release activity. This allows for more flexibility in the incubation time frame and is more amenable to a possible luminescence-based assay.

E. Protease Release Enzyme Sub-cellular Location

HL-60 cells were adjusted to 100,000 cells per ml and split into two aliquots. One aliquot was sonicated using a microtip MISONIX™ 3000 with 30% power for three 5 second pulses. 100 µl of this lysate (confirmed morphologically) was added to multiple wells of a clear-bottomed, 96 well plate and two-fold serially diluted in RPMI 1640 with 10% FBS. Similarly, 100 µl of the non-sonicated cell suspension was added and serially diluted in multiple wells of the plate. NP-9 and digitonin were added to separate wells at 0.2% and 30 µg/ml final, respectively. An untreated control consisted of viable cells and a matched volume of water vehicle. A luciferin detection cake (Promega V859A) was rehydrated with 2 ml 10 mM Hepes, pH 7.5 and made 500 µM with Ala-Ala-Phe-aminoluciferin (Promega). 20 µl of this proluminescent protease release solution was added to all wells and luminescence measured after incubation at 37° C. for 15 minutes using a BMG FLUOstar Optima.

Figure 17:
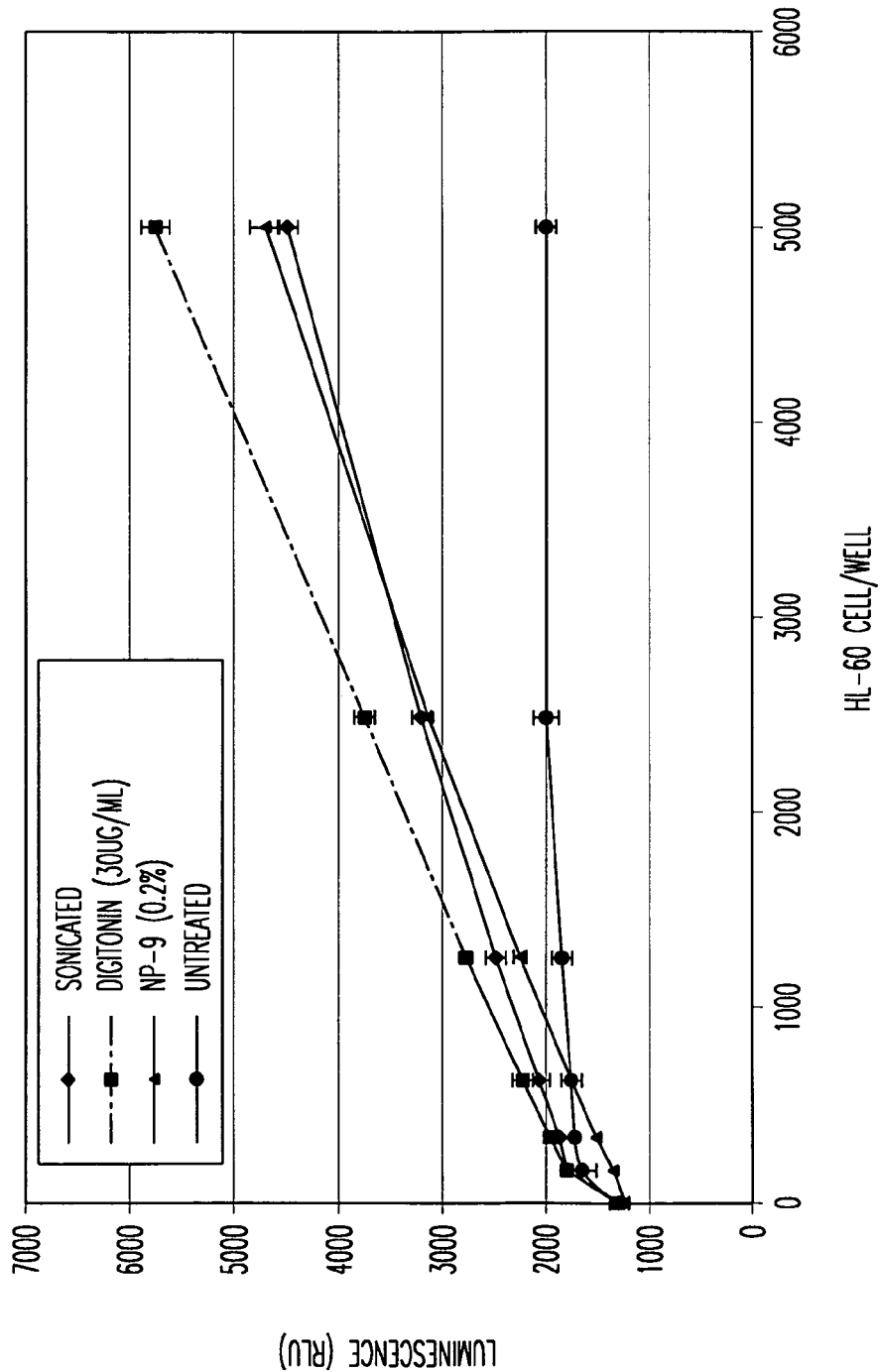
FIG. 17. Protease release from HL-60 cells contacted with Ala-Ala-Phe-aminoluciferin and subjected to different lysis treatments.

Sonication and NP-9, with the above parameters and concentrations, is known to disrupt not only the outer membrane, but also lysosomal contents (as measured by cathepsin release) (FIG. 17). Selective disruption by digitonin allows for trypan blue staining with no evidence of lysosomal rupture. Therefore, because the activities were similar between sonication or differential detergent lysis, and taken together with pH optima, one could surmise that the protease measured in the protease release assay is probably cytosolic and outside of an intact organelle(s).

F. Protease Release or Retention Enzyme Substrate Selectivity

Ala-Ala-Phe-AMC was obtained from Promega. Z-Leu-Leu-Val-Tyr-aminoluciferin (LLVY corresponds to SEQ ID NO:18), Z-Leu-Arg-aminoluciferin, Z-Phe-Arg-aminoluciferin, Ala-Ala-Phe-aminoluciferin, (Ala-Ala-Phe)$_2$-R110, and (Gly-Phe)$_2$-R110 were synthesized by Promega Biosciences. Suc-Ala-Ala-Phe-AMC, H-Phe-AMC, H-Tyr-AMC, Glutyl-Ala-Ala-Phe-AMC (EAAF corresponds to SEQ ID NO:32), H-Gly-Phe-AMC, Z-Gly-Ala-Met-AMC, Suc-Leu-Leu-Val-Tyr-AMC (LLVY corresponds to SEQ ID NO:18), D-Ala-Leu-Lys-AMC, H-Gly-Ala-AMC, H-Gly-Gly-AMC, Suc-Ala-Ala-Phe-AMC, Z-Arg-Leu-Arg-Gly-Gly-AMC (RLRGG corresponds to SEQ ID NO:29), Z-Leu-Arg-Gly-Gly-AMC (LRGG corresponds to SEQ ID NO:30) and Ac-Ala-Ala-Tyr-AMC were sourced from Bachem. Gly-Phe-AFC, Pro-Phe-Arg-AMC, Gly-Gly-Leu-AMC, and Ser-Tyr-AFC were obtained from Calbiochem. Z-Phe-Arg-AMC and Suc-Arg-Pro-Phe-His-Leu-Leu-Val-Tyr-AMC (RPHLLVY corresponds to SEQ ID NO:31) were purchased from Sigma.

All substrates were solubilized in DMSO from 10 to 100 mM depending upon inherent solubility. Fluorescent substrates were diluted to 100 µM to 1 mM in 10 mM Hepes, pH 7.5 or matched cell culture medium with 10% serum and added in $\frac{1}{10}^{th}$ volumes to lysed (freeze fractured, sonicated, or detergent) or untreated viable cells in white-walled, clear bottomed 96-well plates. HL-60 or Jurkat were used in the experimentation interchangeably because of their easily manipulated suspension phenotype. Plates were incubated for 15-30 minutes at 37° C. prior to measuring fluorescence by the CYTOFLUOR™ II.

Luminescent substrates were added to a luciferin detection cake (Promega V859A) resuspended in 2 ml 10 mM Hepes, pH 7.5 to 500 µM. $\frac{1}{5}^{th}$ volume of the proluminescent reaction mixes were added to lysed (freeze fractured, sonicated, or detergent) or untreated viable cells in white-walled, clear bottomed 96-well plates. Again, HL-60 or Jurkat were used in the experimentation interchangeably. Plates were incubated at 37° C. in a MeCour' circulating heat block controlled by a Caron 2050W exchange unit. Luminescence was measured between 15 and 30 minutes (signal steady state).

A broad variety of proteolytic substrates were examined in an effort to characterize potential substrate preferences for protease release or retention in compromised or viable cells (see Table 4). Amino-terminally blocked substrates (Z, Suc-, or Ac-) were chosen to delineate whether an endo or exopeptidase activity predominated. Non-blocked substrates (H—and the like) were examined to include the contribution of aminopeptidase activities. From this panel, at least three proteolytic profiles emerged: an aminopeptidase-like activity preferring unblocked Ala-Ala-Phe tripeptide, a proteosomal (chymotrypsin-like) activity measured by release of blocked Leu-Leu-Val-Tyr (SEQ ID NO:18) peptides, and an exceedingly labile activity by Gly-Phe, Gly-Ala, Phe-, Tyr- or Gly-Gly-Leu substrates. The latter activities were only measurable in viable, intact cells. Of further significance is that several fluorophores or proluminescent labels can be used to detect these activities, ultimately allowing for enhanced downstream multiplexing flexibility.

G. Protease Retention Activity and the Viable Cell Requirement

Jurkat cells were seeded into white-walled, clear-bottomed 96 well plates at a density of 20,000 cell per well in 50 µl volumes. Serial dilutions of the apoptosis inducing agent, rTRAIL (BioMol), were made in RPMI 1640+10% FBS from 500 ng/ml and added in 50 µl volumes in replicates to the cells. Addition of 50 µl medium served as the vehicle control. The plate was incubated at 37° C. with 5% $CO_2$ for a period of 4 hours. Gly-Phe-AFC was diluted to 1 mM in RPMI 1640 and added in 10 µl volumes to all wells. The plate was then placed on the MeCour' circulating heat block for a period of 30 minutes prior to measuring fluorescence at Ex. 405 Em. 530 by a CYTOFLUOR™ II. Next, an equal volume of Cell-Titer-Glo™ reagent was added to the wells and ATP content remaining in the cells examined by luminescence measurement by the FLUOstar Optima.

Figure 18:
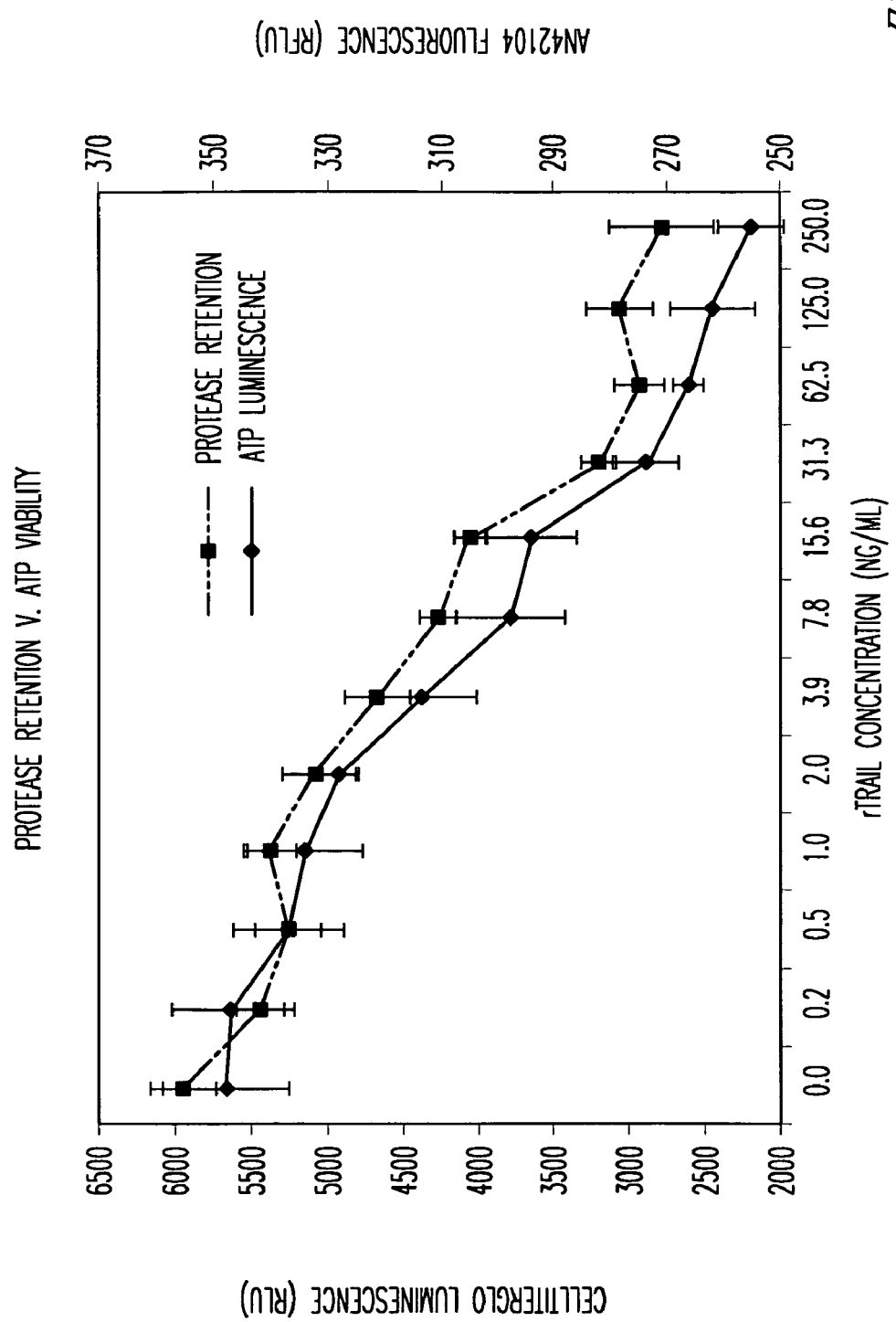
FIG. 18. Plot of ATP luminescence and RFLU for a protease retention assay reagent versus rTRAIL concentration.

Relative ATP levels and protease retention activity were virtually super-imposable, suggesting the requirement for cell viability or an undisturbed cell membrane for optimal retention enzyme activity (FIG. 18). Because perturbed membrane integrity is so detrimental to retention activity, this activity can be coupled with the release activity for a "live/dead" format for detection of population viability.

H. Protease Retention Assay Formats using Different Peptide Sequences and Reporters Actively doubling Jurkat cells were serially diluted from 37,500 cells/well in RPMI 1640+10% FBS in a white-walled,

TABLE 4

| Substrate: | Target Protease(s) | Retention | Release |
| --- | --- | --- | --- |
| Z-Phe-Arg-AMC | Cathepsin B, L | None[1] | None |
| Z-Gly-Gly-Leu-AMC | 20S Proteasome | ++* | None |
| Z-Arg-Leu-Arg-Gly-Gly-AMC (RLRGG corresponds to SEQ ID NO: 29) | Isopeptidase T | None | None |
| Z-Leu-Arg-Gly-Gly-AMC (LRGG corresponds to SEQ ID NO: 30) | Isopeptidase T | None | None |
| S-R-P-F-H-L-L-V-Y-AMC (SRPFHLLVY corresponds to SEQ ID NO: 34) | Proteosome, Chymotrypsin | None | None |
| H-Pro-Phe-Arg-AMC | Kallikrein | None | None |
| H-Gly-Gly-AMC | Aminopeptidase | None | None |
| H-Gly-Ala-AMC | Aminopeptidase | ++ | None |
| H-D-Ala-Leu-Lys-AMC | Plasmin | None | None |
| Ala-Ala-Phe-AMC | Tripeptidyl Peptidase II | None | +++++ |
| (Ala-Ala-Phe) 2 R110 | Tripeptidyl Peptidase II | None | +++++ |
| Ala-Ala-Phe-Aminoluc | Tripeptidyl Peptidase II | None | +++++ |
| Gluty-Ala-Ala-Phe-AMC (EAAF corresponds to SEQ ID NO: 32) | Chymotrypsin | None | None |
| Gly-Phe-AFC | Cathepsin C | +++++ | None |
| Gly-Phe-AMC | Cathepsin C | ++ | None |
| (Gly-Phe)2 R110 | Cathepsin C | None | None |
| Suc-Leu-Leu-Val-Tyr-AMC (LLVY corresponds to SEQ ID NO: 18) | Calpain, Chymotrypsin | None | + |
| Z-Leu-Leu-Val-Tyr-Aluc (LLVY corresponds to SEQ ID NO: 18) | Calpain, Chymotrypsin | None | ++ |
| Z-Gly-Ala-Met-AMC |  | None | None |
| Ac-Ala-Ala-Tyr-AMC | Chymotrypsin | None | None |
| Z-Leu-Arg-Aluc | Cathepsin K | None | None |
| Z-Phe-Arg-Aluc | Cathepsin B, L | None | None |
| Ser-Tyr-AFC | Aminopeptidase | None | None |
| H-Phe-AMC | Aminopeptidase M | +++ | None |
| H-Tyr-AMC | ApM or Cathepsin H | ++ | None |
| Suc-Ala-Ala-Phe-AMC | Chymotrypsin | None | None |

None denotes no statistical activity above control population.
(+) to (+++++) denotes the range of activity above control population from modest to robust clear bottomed 96 well plate in 100 μl volumes. The cells in half of the plate were lysed with the addition of Triton X to 0.2% final. The other half of the plate wells received a matched volume (5 μl) of water vehicle. Tyr-AMC, Phe-AMC and Gly-Phe-AFC were all rehydrated in DMSO to 100 mM then diluted in RPMI 1640 to 1 mM. 1/10th volume of diluted substrates were added to the wells, mixed briefly by orbital shaking then incubated at 37° C. in 5% $CO_2$ for up to 1.5 hours. Resulting fluorescence was measured at Ex. 360 Em. 460 and Ex. 405 and Em. 500 at 30 and 90 minutes.

Figure 19B:
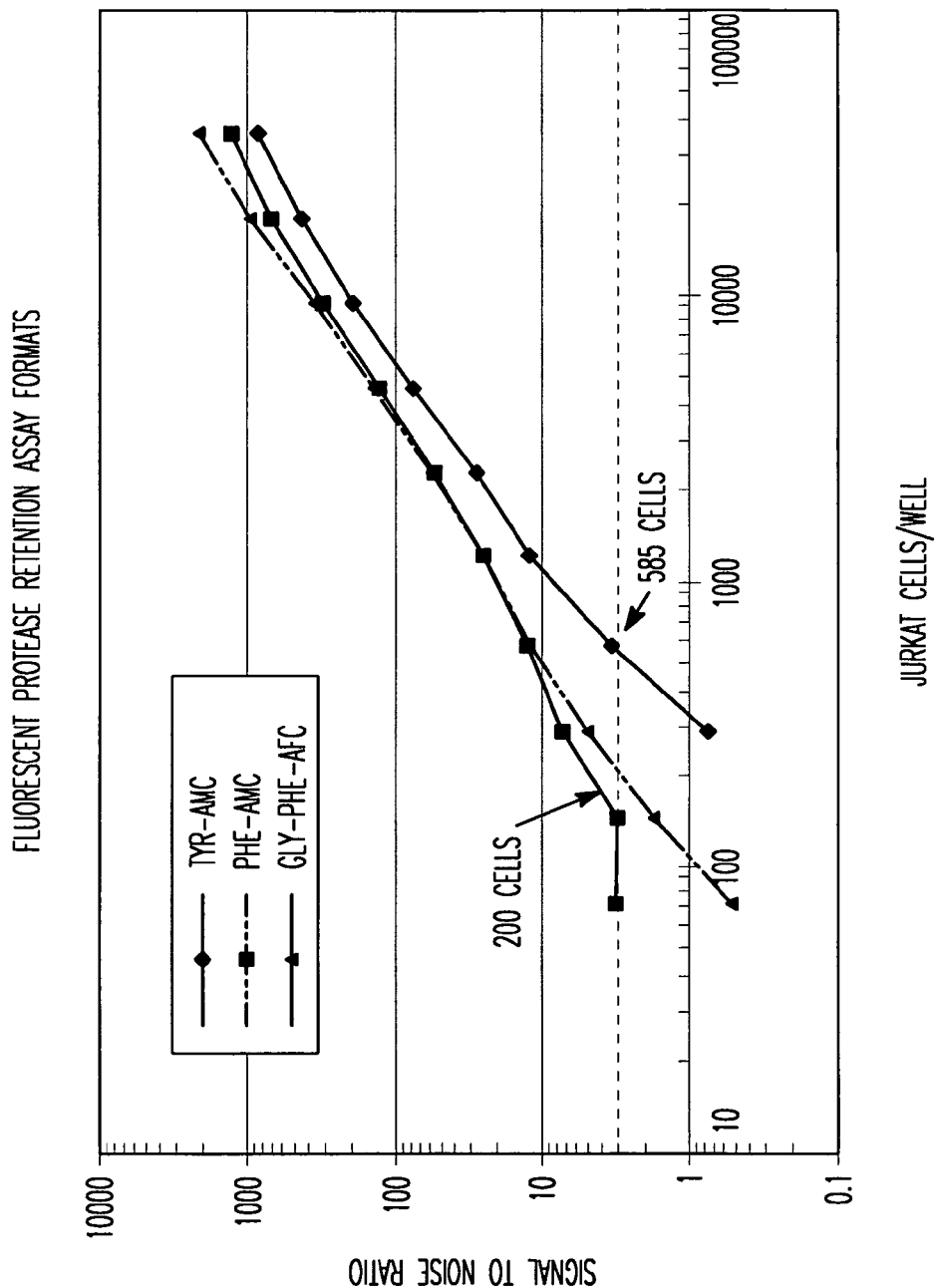
FIG. 19B. Sensitivity of three different substrates in a protease retention assay.

The peptide sequences that work well in differentiating live from dead cells (targeted and utilized by live cells) are either unblocked mono- or bi-peptide substrates which can presumably freely enter the cytoplasm of viable cells (FIG. 19). A candidate substrate, $(Gly-Phe)_2$-R110, was apparently unable to effectively traverse the cell membrane or was not effectively cleaved by the candidate protease.

I. Protease Release Activity Half-Life

Jurkat cells were seeded into white-walled, clear-bottomed 96 well plates at a density of 20,000 cell per well in 100 μl volumes. Saponin (Sigma) was added and mixed briefly by orbital shaking to 0.2% final concentration (5 μl addition) to replicate wells every hour, over an 8 hour time course. During this same time frame, an equal volume of RPMI 1640 with 10% FBS was added to control wells. Ala-Ala-Phe-AMC was diluted to 500 μM in RPMI 1640+10% FBS and added in 10 μl volumes to the wells, and mixed briefly by orbital shaking prior to incubation at 37° C. in 5% $CO_2$ for 1 hour. The resulting fluorescence was measured on a CYTOFLUOR™ II.

Figure 20:
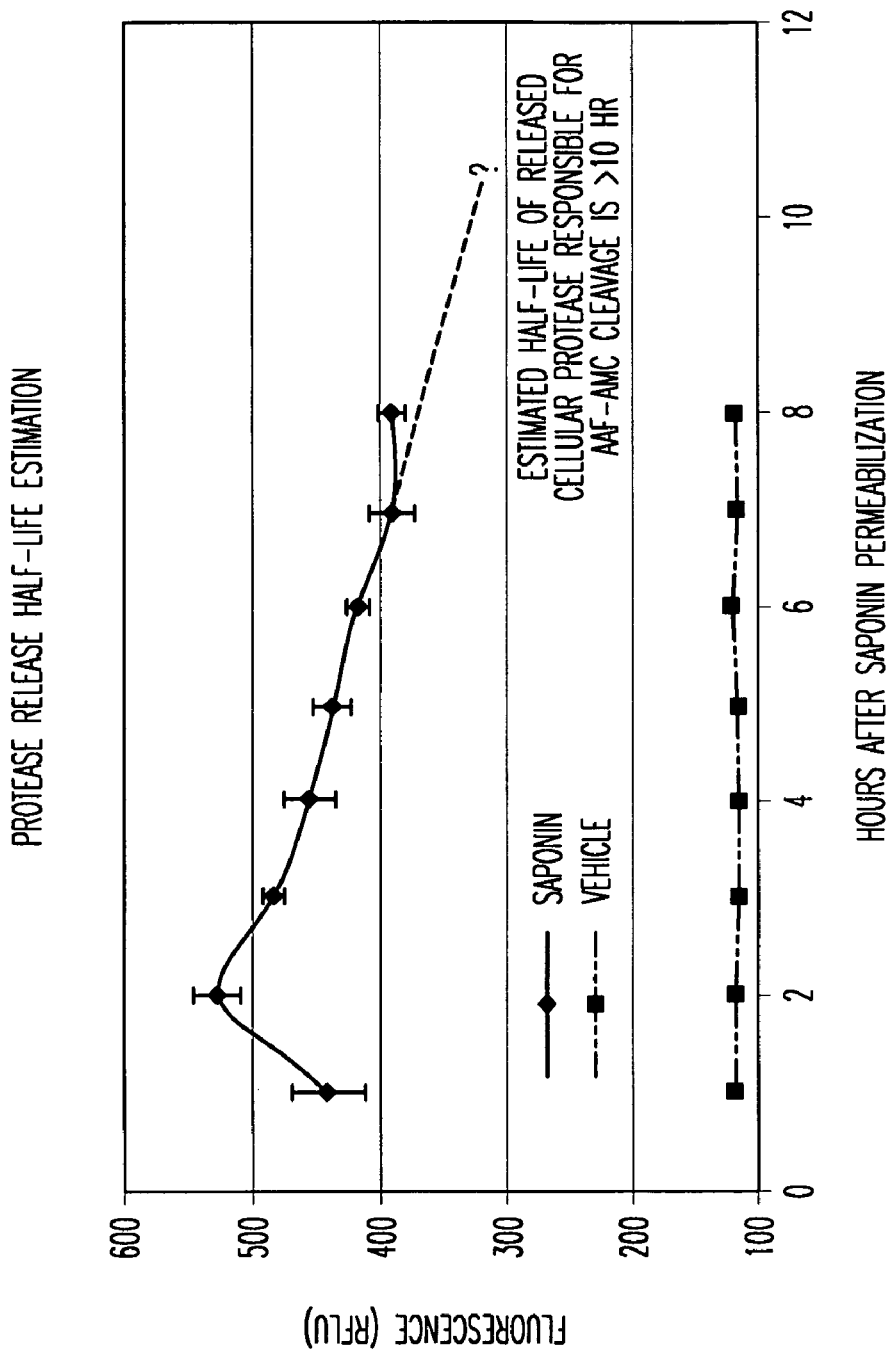
FIG. 20. Half life of protease activity for a protease released after saponin treatment.

The released protease activity half-life approaches 10 hours when extrapolated for activity decay (FIG. 20). This extended activity in the cell culture lysate compares favorably with lactate dehyrdrogenase (LDH) with an estimated half-life of approximately 9 hours. This observation is significant with regards for this protease activity being a surrogate for cell death in a treated population. Simply stated, the longer the signal half-life, the greater the utility the assay has in reporting cell death (without diminishing activity underestimating the response) in typical in vitro protocols.

J. Protease Retention and Release Activity Inhibition/Augmentation Profiles

Puromycin, E-64, Phenylmethanesulfonyl fluoride (PMSF), Adenosine 5'-triphosphate (ATP), N-(α-Rhamnopyranosyloxyhyrdoxyphosphinyl)-Leu-Trp disodium salt (Phosphoramidon), N-[(2S,3R)-3-Amino-2-hydroxy-4-phenylbutyryl-L-leucine hydrochloride (Bestatin), 1,10-Phenathroline, 3,4-diisocoumarin, 4-(2-Aminoethyl)benzenesulfonyl fluoride (AEBSF), 1,4-Dithio-DL-threitol (DTT), Edetate disodium dihyrdrate (EDTA), Isovaleryl-L-valyl-L-valyl-[(3S,4S)-4-amino-3-hydroxy-6-methylheptanoyl]-L-alanyl[93S,4S]-4-amino-3-hydroxy-6-methylheptanoicacid (Pepstatin A), sodium chloride, Aprotinin, N-Acetyl-L-leucyl-L-leucyl-L-argininal hemisulfate salt (leupeptin) were all purchased from Sigma. Inhibitors were resuspended in DMSO to varying stock concentrations with a high target concentration of 200 μM or 200 μg/ml in Dulbecco's Phosphate Buffer Saline w/o $Mg^{++}$ or $Ca^{++}$ (DPBS) for addition to either lysates or viable cell populations. DTT, NaCl, EDTA, and ATP were also diluted in DPBS. All compounds were incubated with compromised or viable cells for a period of at least 30 minutes (most 60 minutes) at 37° C. prior to assessment of activity.

The protease retention assay inhibitor/adjuncts survey was conducted on sonicated, saponin-lysed, or viable HL-60 and/or U937 using Gly-Phe-AFC at 100 μM final concentration as described previously. The protease release assay inhibitor/adjuncts survey was conducted on sonicated, saponin-lysed, or viable HL-60, SK-MEL-28, and/or U937 using Ala-Ala-Phe-AMC or $(Ala-Ala-Phe)_2$-Rhodamine 110.

The protease retention activity profile in the presence of various class inhibitors or adjuncts indicates that the majority of the activity observed relates to an aminopeptidase (puromycin, EDTA, and Bestatin sensitivities) (see Tables 5 and 6). This activity is ATP- and DTT-independent (no restoration of activity) as well as insensitive to halides ($Cl^-$). This activity does appear to be related to cysteine or serine protease class enzymes.

The protease release activity profile appears to be sensitive to serine protease inhibitors, but not those with selectivity for trypsin or chymotrypsin-like activities. There is no apparent requirement for thiols (strongly indicative of cysteine class) and specific inhibitors of aspartic and metallo-proteases are ineffective in controlling activity.

The enzyme responsible for protease retention activity requires a viable cell and can not be detected outside of compromised cells. Conversely, no admixed adjuncts are required to potentiate the protease release response. This allows for combining the assays in a non-toxic, non-lytic format, to detect live and dead cells based on their differential protease activities.

TABLE 5

Retention Assays with Gly-Phe-AFC and HL-60 and/or U937

| Inhibitor/Adjunct | Target Class | Effect | Comments |
|---|---|---|---|
| Puromycin | Aminopeptidase | Inhibition | Very modest |
| EDTA | Metallo | Inhibition | Also reduces viability |
| DTT | Cysteine | Augments | Very slightly in lysate |
| NaCl | Aminopeptidases | No inhib | Insensitivity |
| 1,10 Phenanthroline | Metallo | No inhib | to 100 uM |
| Bestatin | Aminopeptidase | Inhibition | Strong |
| 3,4 Diisocoumarin | Serine | Inhibition(?) | Kills cells |
| Phosphoramidon | Metallo | No inhib | to 100 uM |
| E-64 | Cysteine | No inhib | to 100 uM |
| PMSF | Serine/Cysteine | No inhib | to 100 uM |
| ATP | ATP dependent | No effect | to 100 uM |

TABLE 6

Release Assays with Ala-Ala-Phe-AMC and HL-60, SK-MEL-28, U937

| Inhibitor/Adjunct | Target Class | Effect | Comments |
|---|---|---|---|
| Bestatin | Metallo (aminopeptidase) | No inhib | to 10 uM |
| EDTA | Metallo | No inhib | to 50 mM |
| Pepstatin | Aspartic | No inhib | to 100 uM |
| AEBSF | Serine | Inhibition | Strong |
| PMSF | Serine/Cysteine | Inhibition | Strong |
| Aprotinin | Serine (trypsin, chymo-like) | No inhib | to 100 uM |
| Leupeptin | Serine (trypsin-like) | No inhib | to 100 ug/ml |
| Antitrypsin | Serine (trypsin-like) | No inhib | to 100 ug/ml |
| FPR-CMK | Serine/Cysteine | Inhibition | Moderate |
| DTT | Cysteine | Augments | Modest improvement |
| 3,4 Diisocoumarin | Serine | Inhibition | Strong |
| E-64 | Cysteine | No inhib | to 100 uM |
| 1,10 Phenanthroline | Metallo | No inhib | to 100 uM |
| Phosphoramidon | Metallo | No inhib | to 100 uM |

K. Multiplexed Protease Release and Retention Assays

1. Jurkat Dose Response

Actively doubling Jurkat cells were seeded into 96-well plates at a cell density of 20,000 cells per well in 50 µl volumes. Serial dilutions of the apoptosis inducing ligand, rTRAIL in RPMI 1640, were added to replicate wells from 250 ng to 244 pg/ml final concentration in an additional 50 µl volume. RPMI only served as uninduced control. The plate was incubated at 37° C. in 5% $CO_2$ for a period of 4 hours. Gly-Phe-AFC and Ala-Ala-Phe-AMC were simultaneously diluted to 1 mM in RPMI and added in a $\frac{1}{10}^{th}$ volume to the plate and were incubated for an additional 30 minutes at 37° C. Resulting fluorescence was measured at Ex 360 Em 460 and Ex 405 Em 530 using the CYTOFLUOR™ II. After fluorescence measurements were completed, CellTiter-Glo® was added to wells in an equal addition and luminescence measured using the BMG FLUOstar Optima.

Figure 21A:
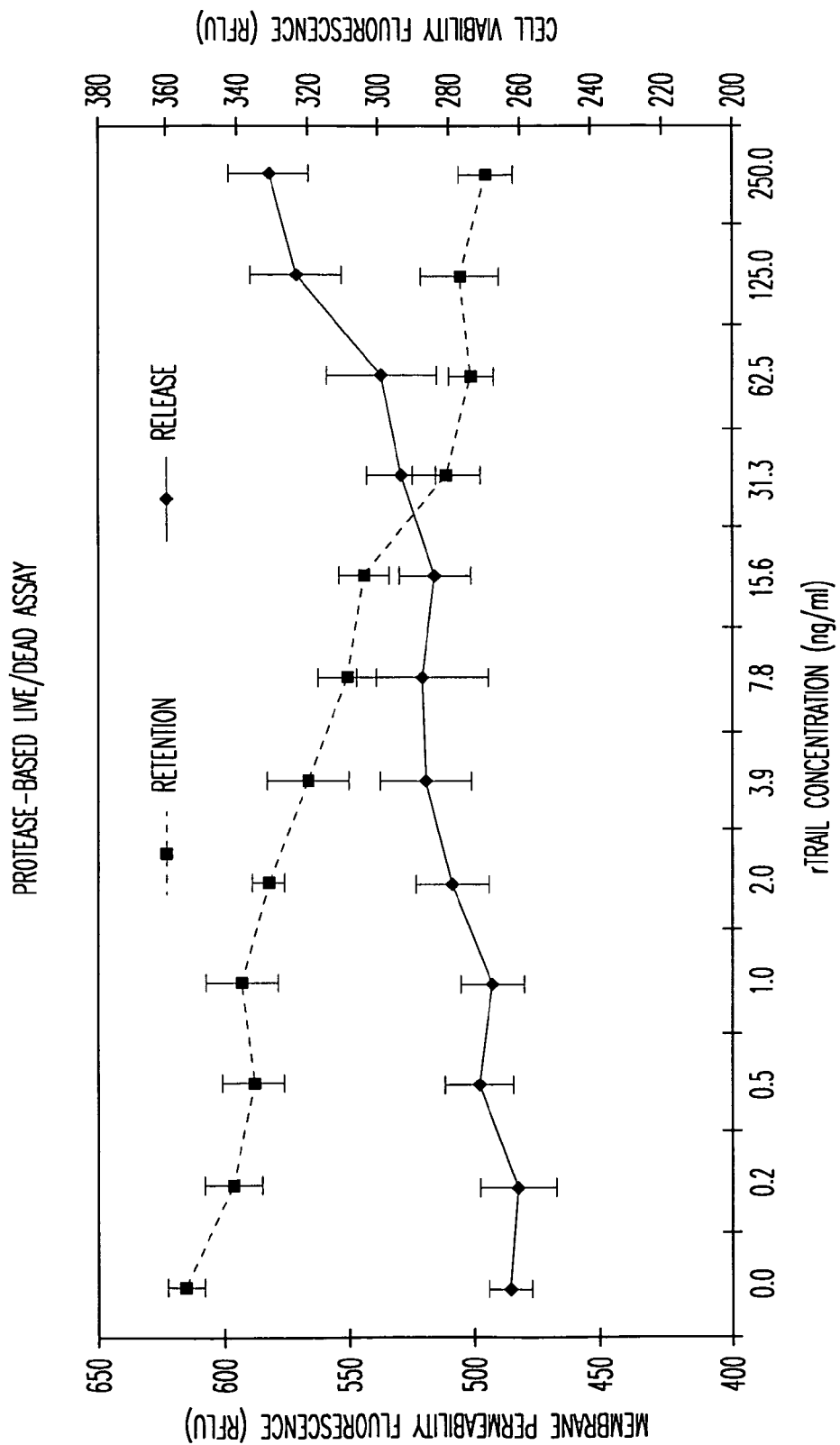
FIG. 21A. Protease based live/dead cell assay.
Figure 21B:
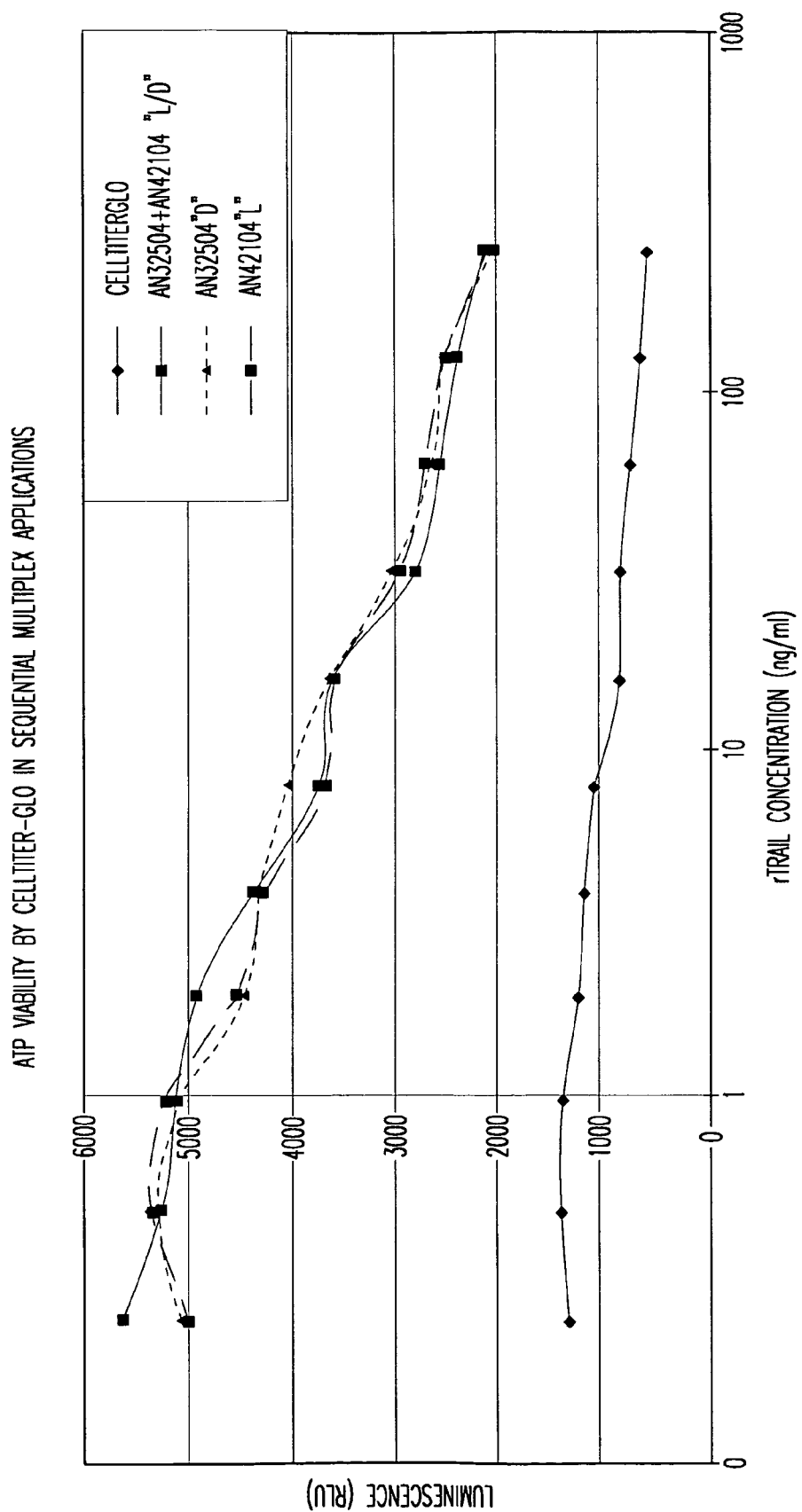
FIG. 21B. ATP viability assay in sequential multiplex applications with live, dead or live/dead cell assays.
Figure 21C:
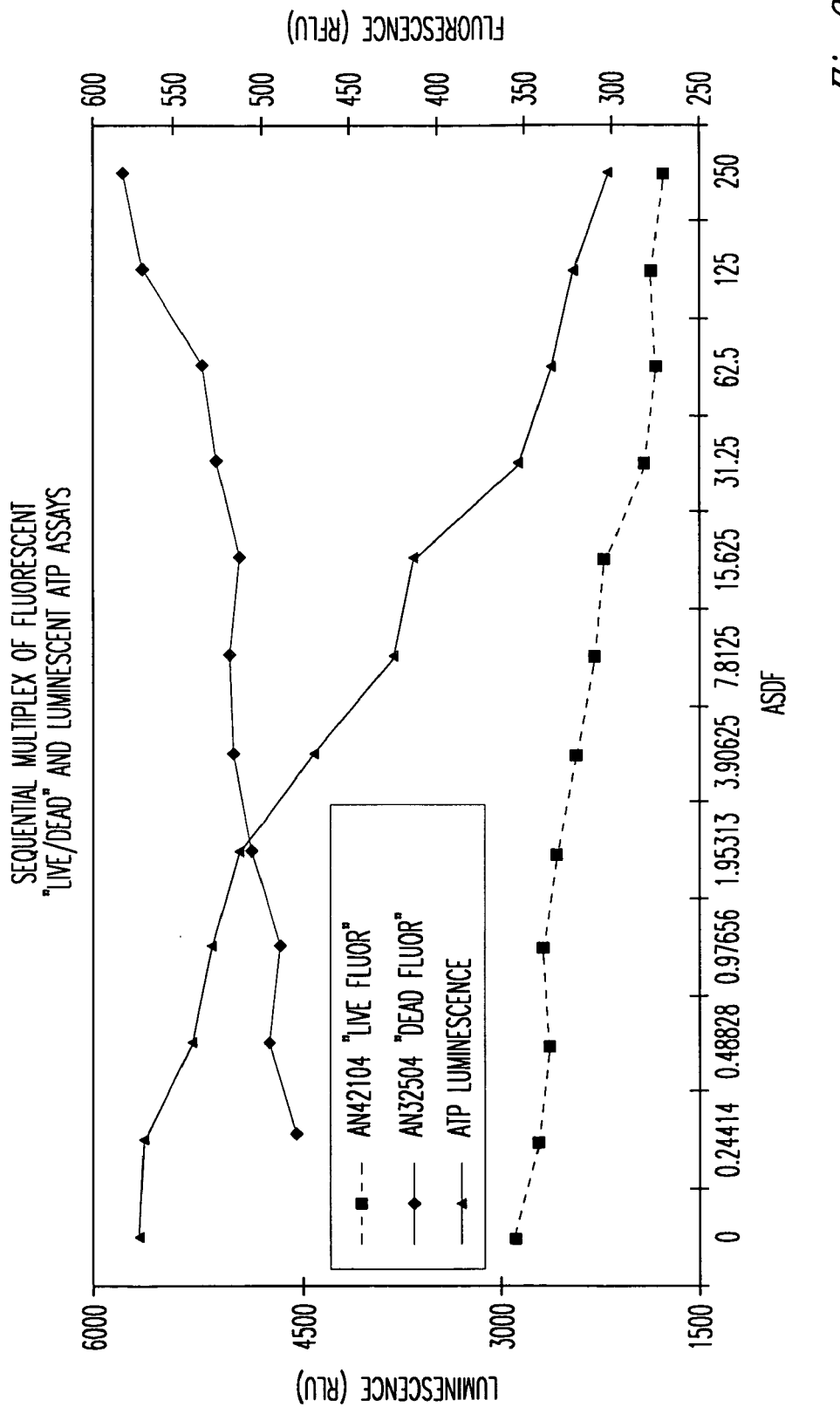
FIG. 21C. Sequential multiplex of fluorescent live or dead and luminescent ATP assays.

Two independent non-destructive surrogates of cell health (protease release and retention) were multiplexed to report population viability in a micro-titer plate format (FIG. 21). The resulting data are converse measures of the health of that cell population. This relationship allows for use of a control and provides a level of normalization. Furthermore, a third measure of viability (ATP content) can be added in a sequential multiplex format with no interference or quenching allowing for further confidence in the interpretation of the data.

2. SK-MEL-28 and ACHN Cells

SK-MEL-28 or ACHN cells were seeded into white-walled, clear bottomed 96 well plates at a density of 10,000 cells per well in 100 µl volumes and allowed to attach at 37° C. in 5% $CO_2$ for a period of 2 hours. After attachment, 50 µl of medium was carefully removed and replaced with serial dilutions of either ionomycin or staurosporine in MEM+10% FBS. Medium only served as control. The plate was incubated for an additional 5 hours. A 1 mM solution of Gly-Phe-AFC was made in MEM and added to the wells in a $\frac{1}{10}^{th}$ volume. Resulting fluorescence was measured using a CYTOFLUOR™ II. Caspase-Glo™ 3/7 reagent was then added and luminescence measure using a BMG FLUOstar Optima.

Figure 22A:
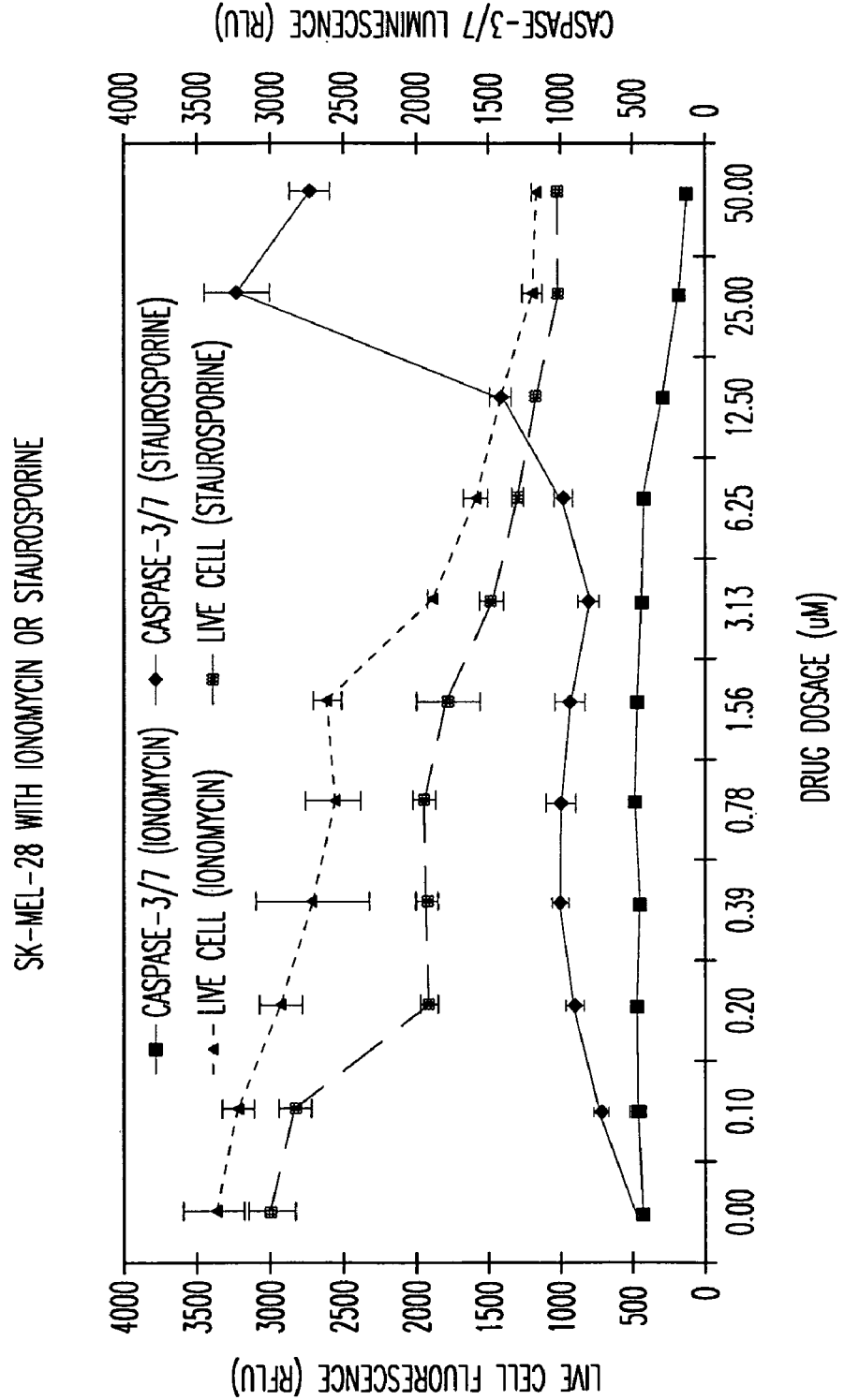
FIG. 22A. Live cell RFLU and RFLU for caspase 3/7 activity versus increasing concentrations of ionomycin or staurosporin in SK-MEL-28 cells.
Figure 22B:
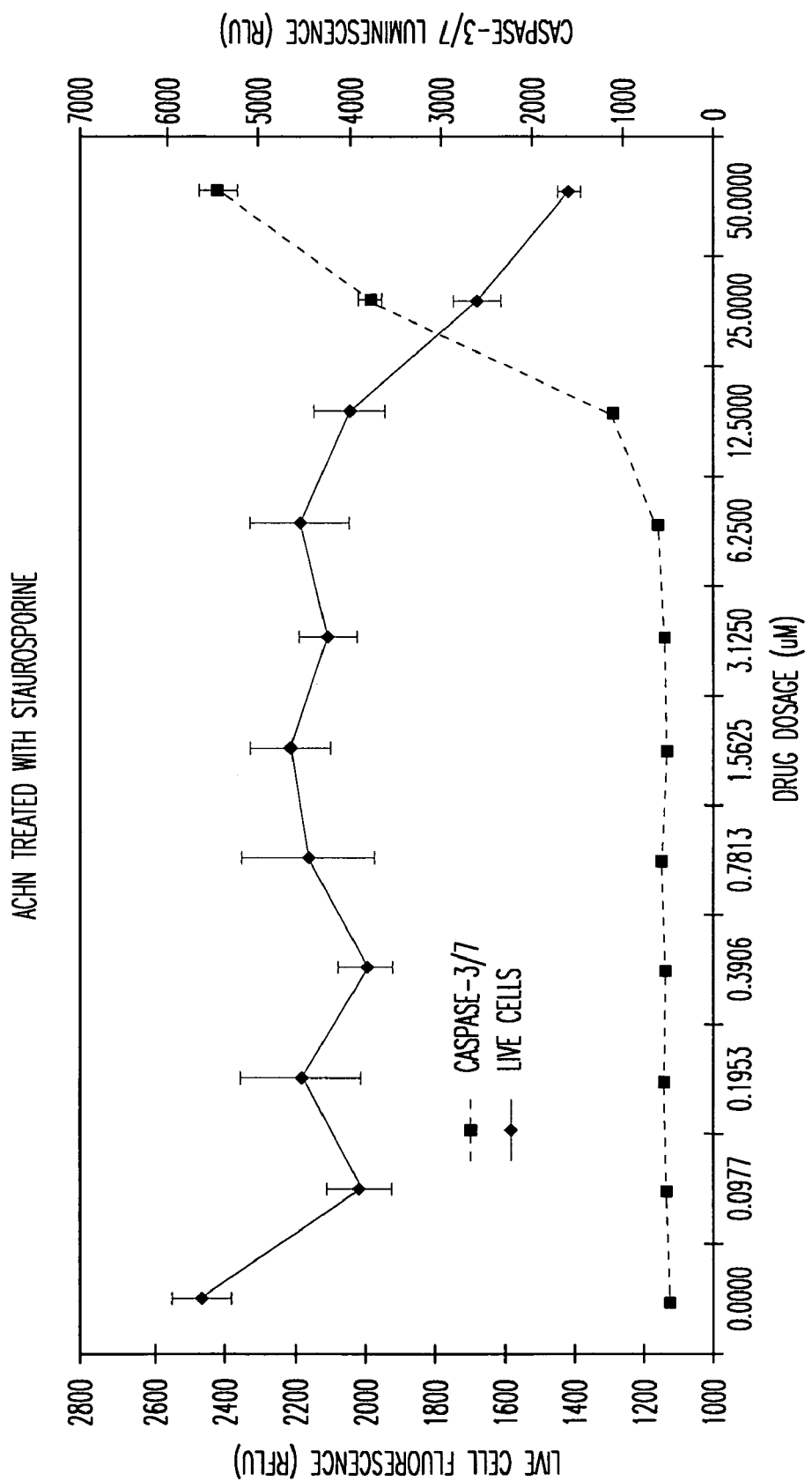
FIG. 22B. Live cell RFLU and RLU for caspase 3/7 activity versus increasing concentrations of staurosporin in ACHN cells.

The protease retention substrate reported the general viability in the well, whereas the caspase specific reagents reported specific pathways of cytotoxicity (FIG. 22). In this regard, caspase activation (and therefore apoptosis induction) is evident with staurosporine on SK-MEL-28, whereas ionomycin initates a necrotic-type profile. An apoptotic profile is also observed with staurosporine treated ACHN.

3. HeLa Cells and Tamoxifen Treatment

HeLa cells were seeded into white-walled, clear bottomed 96 well plates at a density of 10,000 cells per well in 100 µl volumes and allowed to attach at 37° C. in 5% $CO_2$ for a period of 2 hours. After attachment, 50 µl of medium was carefully removed at 24, 7, 5, 3, 1 and 0 hours of exposure time and replaced with 50 µM tamoxifen in MEM+10% FBS. Medium only served as control. A protease retention and release reagent was prepared by rehydrating a luciferin detection reagent cake with 2 ml of 10 mM Hepes, pH 7.5. The solution was then made 500 µM with both Ala-Ala-Phe-aminoluciferin and Gly-Phe-AFC. A $\frac{1}{5}^{th}$ volume of the solution was added to all wells and incubated for 15 minutes at 37° C. in the Me'Cour thermo unit. Luminescence was measured by a BMG FLUOstar Optima and fluorescence measured using a CYTOFLUOR™ II.

Figure 23:
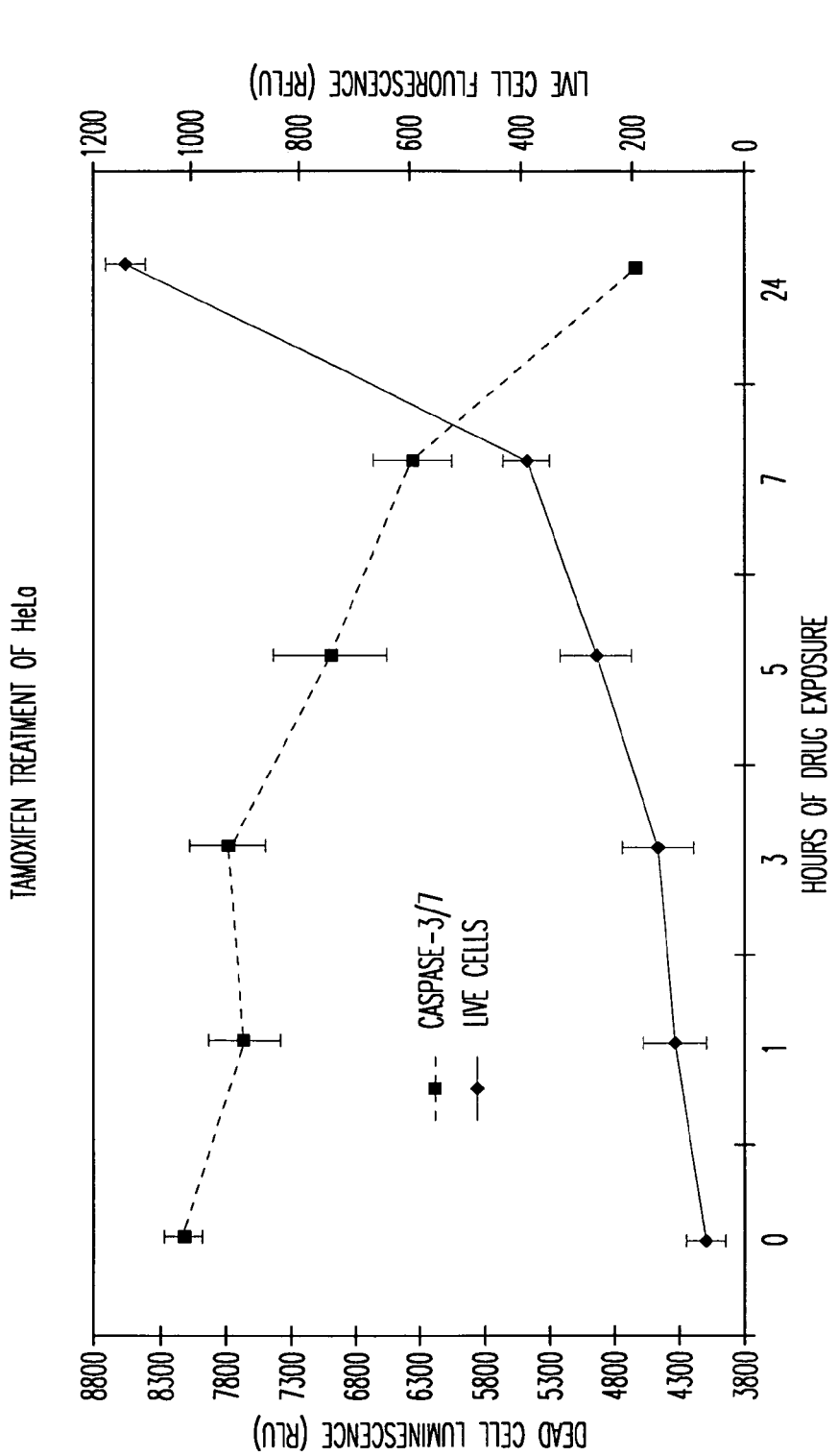
FIG. 23. Plot of dead HeLa cell luminescence and live HeLa cell fluorescence versus hours of tamoxifen treatment.

This example demonstrates that a mixed platform (fluorescence and luminescence) is possible in a configured protease retention and release assay (FIG. 23). It is notable that these reagents are non-lytic and apparently non-toxic suggesting that they are amenable to other downstream applications that are spectrally distinct such as caspase-3/7 detection by the Apo-ONE™ assay.

4. Use of a Live/Dead Protease Assay with a DNA Stain

HeLa or HepG2 cells were seeded into white-walled, clear bottomed 96 well plates at a density of 10,000 cells per well in 100 µl volumes and allowed to attach at 37° C. in 5% $CO_2$ for a period of 2 hours. After attachment, 50 µl of medium was carefully removed and replaced with serial dilutions of tamoxifen or Ionomycin in MEM+10% FBS. Medium only served as control. Incubation with the compounds was continued for an additional 5 hours. A protease retention and release reagent was prepared by rehydrating a luciferin detection reagent cake (Promega V859A) with 2 ml of 10 mM Hepes, pH 7.5. The solution was then made 500 µM with both Ala-Ala-Phe-aminoluciferin and Gly-Phe-AFC. A $\frac{1}{5}^{th}$ volume of the solution was added to all wells and incubated for 15 minutes at 37° C. in the Me'Cour thermo unit. Luminescence was measured by a BMG FLUOstar Optima and fluorescence measured using a CYTOFLUOR™ II. Next, remaining viable cells were lysed by the addition of 0.4% NP-9 detergent. After brief mixing on an orbital shaker, a 1:20 dilution of PicoGreen® (Molecular Probes) in MEM was added in an additional $\frac{1}{10}^{th}$ volume. Fluorescence associated with DNA/dye binding was measured using a CYTOFLUOR™ II at Ex. 485 Em. 530.

Figure 24A:
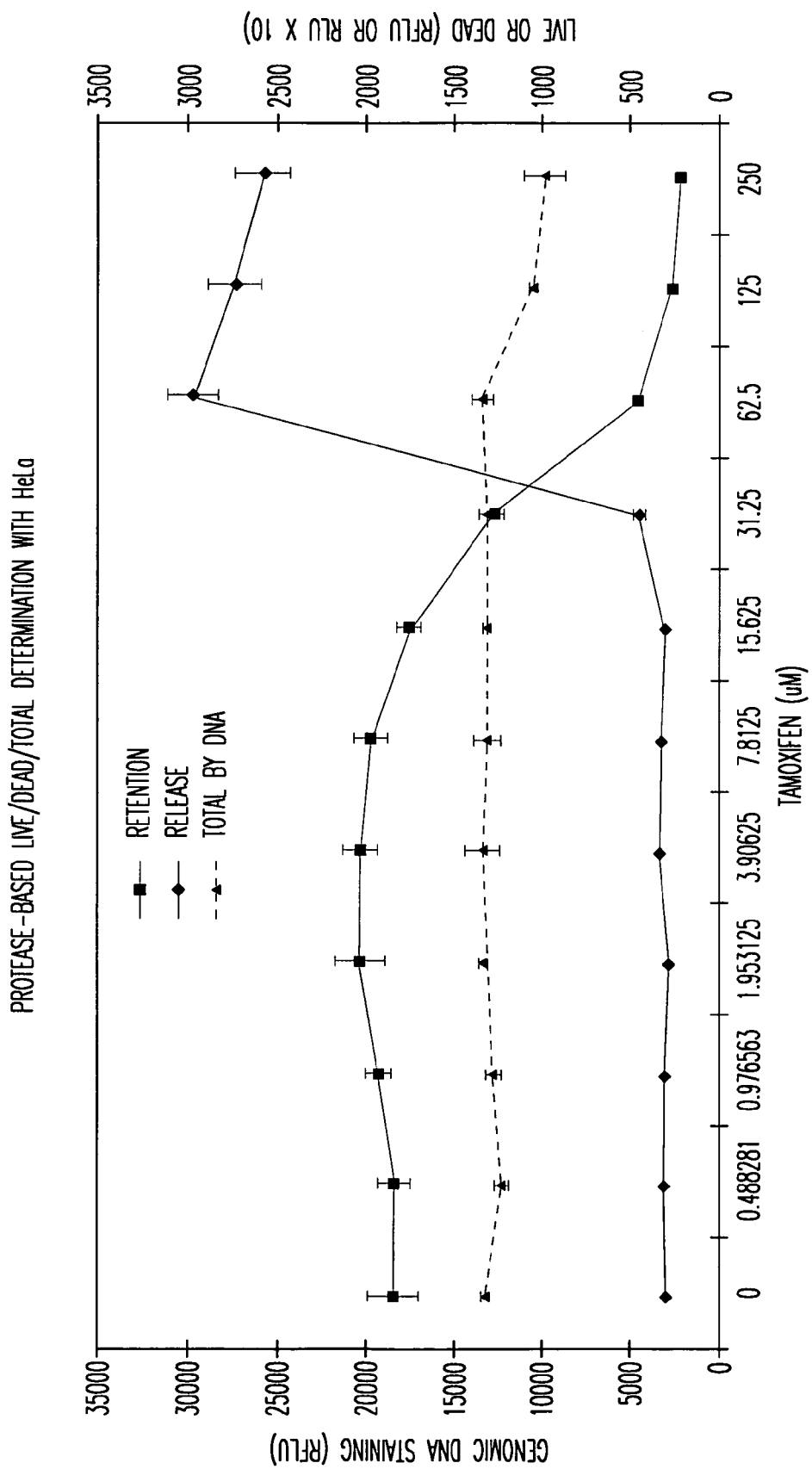
FIG. 24A. Protease based live/dead assay with HeLa cells treated with tamoxifen and stained with PicoGreen™.

This experiment not only expands the utility of protease based viability testing to two additional adherent cell types of screening favor, but incorporates a "total" measure by DNA staining (FIG. 24). Because of spectral distinctness and mixed platform readout, all measures are non-interfering and non-quenching.

Discussion

Both drug discovery and primary research efforts continue to utilize increasingly sophisticated cell model systems. The obligate need to measure cell number and viability in these in vitro systems after experimental manipulation is well appreciated. This requirement is necessary to verify the validity of measures and normalize these responses within the context of complex biological systems.

Unfortunately, current chemistries for defining cellular viability and cytotoxicity have not kept pace with the new methodologies and techniques of biological inquiry and have therefore limited experimental options. For instance, the emergence of assay multiplexing, i.e., combination assays in the same well, have necessitated the requirement for compatible and spectrally distinct assay combinations without significant reductions in assay performance. This mandate is particularly important in regards to coupling general complimentary measures of cell health with a more specific event such as caspase activation or reporter gene modulation.

The aforementioned methodology for measurement of cell viability and/or cytotoxicity reporters that are compatible with many downstream assay applications. This is accomplished either by distinct fluorophores with divergent excitation and emission spectra or by integrating other reporter platforms such as luminescence. It is noteworthy that this is accomplished in a non-lytic and presumably non-toxic environment allowing for flexibility in assay windows for endpoint determinations. Furthermore, this technology is sufficiently sensitive and cost effective to accommodate throughput, miniaturization and automation. A comparison of advantages offered by various assays is provided in Table 7.

TABLE 7

| Assay Attributes | Protease Release and Retention | Dye Exclusion (Trypan Blue) | Resazurin Reduction | LDH Release | Profluorecein and Propidium Iodide | Radiological Incorporation Or Release | ATP |
|---|---|---|---|---|---|---|---|
| Homogeneous | yes | yes | yes | yes | yes/no | no | yes |
| Non-Destructive | yes | yes | yes | yes | yes | yes | no |
| Reagent Stable in Culture | yes | yes | yes | yes | no | yes | N/A |
| Environment Non-toxic, easy disposal | yes | yes | yes | yes | no | no | yes |
| Non-color quenching | yes | no | no | no | yes | yes | yes |
| Fluorescence | yes | no | yes | yes | yes | no | no |
| Luminescence | yes | no | no | no | no | no | yes |
| Platform Choice | yes | no | no | no | no | no | no |
| Compatible w Endpoint Multiplexes | yes | yes | yes | yes | yes* (If spectrally distinct) | no | no |
| Ratiometric normalization of response | yes | no | no | no | yes | no | no |

In conclusion to date, the balance of published effort in the study of mammalian proteases has revolved primarily around those either easily purified, secreted, or both. Whereas the information provided from these studies has provided insight into proteolytic mechanism, structure and function, little is known about other proteases other than what has been speculated from proteomic prediction. Simply stated, much work needs to be conducted on the function, regulation, sub-cellular distribution, abundance, and importance of intracellular proteases.

Increasing evidence suggest that an number of cytosolic proteases are involved in mechanisms of cellular homeostasis. Although proteosomes are clearly involved in the liberation of cytosolic peptides, several findings suggest a role for other conserved cytosolic proteases (Vititsky et al., 1997; Constam et al., 1995).

The individual protease assays and the protease based live/dead cell assays described herein are more flexible for multiplexing due to spectral distinctness, allowing for assay complementarity or other endpoint assay combinations, e.g., AMC, AFC, R110, cresyl violet or luminescence, no dye quenching, no restrictive volumes, no retroengineering of assay chemistry, short incubation times, similar or better practical sensitivitites (percent change in cell viability in a screening environment), no downstream interference with DNA binding assays, and no need for washing or centrifugation, e.g., homogeneous assays. Moreover, the data from a protease based live/dead assay can be normalized irrespective of cell number when used in a ratio (cytotoxicity index), and the cell/compound contact window can be extended to account for differences in compound action kinetics, e.g., when coupled to other assays such as DNA intercalation (the potential results of primary or secondary necrosis can be identified), and DNA intercalation and caspase activity may identify cell cycle drug responsiveness, e.g., in a heterogeneous population in a well. Further, the substrates for proteases may be relatively simple, e.g., di or tri-peptides, are coupled to fluors or luminogenic substrates by well known chemistries, nontoxic and/or nonmutagenic, stable, and can be provided in various formats, e.g., in DMSO or dry.

REFRENCES

Balow et al., J. Biol. Chem., 261:2409 (1986).
Bond et al., Ann. Rev. Biochem., 56:333 (1987).
Bronstein et al. (In: Bioluminescence and Chemiluminescence: Molecular Reporting with Photons, pp. 451-457 (1996).
Constam et al., J. Biol. Chem., 270:26931 (1995).
Cook et al., Anal. Biochem., 179:1 (1989).
DeJager et al., Clin. Dial. Lab. Immunolo., 10:133 (2003).
Doughty et al., Biochem. Cell Biol., 64:772 (1986).
Femandes-Alnemri et al., PNAS USA, 93:7464 (1996).
Gazi et al., Luminescent, 17:106 (2002).
Geier et al., Science, 283:978 (1999).
Glas et al., Nature, 392:618 (1998).
Haunstetter et al., Circ. Res., 82:1111 (1998).
Liu et al., Luminescence, 15:45 (2000).
Masuda-Nishimura et al., Lett. Appl. Microbio., 30:130 (2000).
Miska and Geiger, J. Clin. Chem. Clin. Biochem., 25:23 (1989).
Monsees et al., Anal. Biochem., 221:329 (1994).
Monsees et al., J. Biolum. Chemilum., 10:213 (1995).
Myers, J. Immunol. Methods, 212:99 (1998).
Nicholson et al., Nature, 376:37 (1995).
Nolkrantz et al., Anal. Chem., 7:4300 (2002).
Page, Encyclopedia of Life Sciences-Nature Publishing Group 1-3 (2001).
Qazi et al., Luminescence, 17:106 (2002).
Renn et al., J. Biol. Chem., 273:19173 (1998).
Riss et al., Assay and Drug Development Technologies, 2:1 (2004).
Silk et al., Gut, 11:870 (1976).
Syntichaki et al., Nature Reviews, 4:672 (2003).
Tewari et al., Cell, 81:801 (1995).
Thomberry et al., Nature, 356:768 (1992).
Tomkinson, Trends Biochem. Sci., 24:355 (1999).
Tomkinson et al., Eur. J. Biochem., 269:1438 (2002).
Tran et al., Archives of Biochemistry and Biophysics, 403: 160 (2002).

Vitnitsky et al., *J. Immunol.* 159:554 (1997).

Yamamoto et al., *Forensic Science International*, 113:143 (2000).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method to detect live and/or dead cells in a sample, comprising:
    a) contacting a sample comprising cells suspected of having one or more proteases with a peptide substrate for a first nonsecreted protease and a peptide substrate for a second nonsecreted protease, wherein a reaction with one of the substrates mediated by one of the proteases yields a fluorogenic product and a reaction with the other substrate mediated by the other protease yields a luminogenic or a fluorogenic product, wherein one of the substrates is substantially cell membrane permeant and the other substrate is substantially cell membrane impermeant, wherein if both reactions yield fluorogenic products, the fluorophores on the two substrates are spectrally distinct, and wherein the substantially cell membrane permeant substrate is capable of detecting or determining the number or presence of live cells in the sample and the substantially cell membrane impermeant substrate is capable of detecting or determining the number or presence of dead cells in the sample as a result of protease activity released into the extracellular environment due to loss of membrane integrity; and
    b) detecting or determining fluorescence and/or luminescence in the sample, thereby detecting or determining the number or presence of live and/or dead cells in the sample.

2. The method of claim 1 wherein a reaction mediated by each protease yields a fluorogenic product.

3. The method of claim 1 wherein a reaction mediated by one protease yields a luminogenic product and a reaction mediated by the other protease yields a fluorogenic product.

4. The method of claim 1 wherein the substantially cell permeant substrate is a substrate for a protease associated with a proteasome, an aminopeptidase or a cathepsin.

5. The method of claim 1 wherein the substantially cell impermeant substrate is a substrate for a tripeptidyl peptidase or calpain.

6. The method of claim 1 wherein the sample comprises mammalian cells.

7. The method of claim 1 wherein the two substrates are combined before contact with the sample.

8. The method of claim 3 wherein fluorescence and luminescence are detected or determined sequentially.

9. The method of claim 2 wherein the fluorescence of each fluorogenic product is detected or determined simultaneously.

10. The method of claim 1 further comprising contacting the sample with one or more agents suspected of altering the number of live and/or dead cells prior to contact with the substrates.

11. A method to detect live and/or dead cells and at least one other molecule in a sample comprising cells, comprising:
   a) contacting a sample comprising cells suspected of having one or more proteases with a peptide substrate for a first nonsecreted protease and a peptide substrate for a second nonsecreted protease, wherein a reaction with one of the substrates mediated by one of the proteases yields a fluorogenic product and a reaction with the other substrate mediated by the other protease yields a luminogenic or a fluorogenic product, wherein one of the substrates is substantially cell membrane permeant and the other substrate is substantially cell membrane impermeant, wherein if both reactions yield fluorogenic products, the fluorophores on the two substrates are spectrally distinct, and wherein the substantially cell membrane permeant substrate is capable of detecting or determining the number or presence of live cells in the sample and the substantially cell membrane impermeant substrate is capable of detecting or determining the number or presence of dead cells in the sample as a result of protease activity released into the extracellular environment due to loss of membrane integrity; and
   b) detecting or determining fluorescence and/or luminescence, thereby detecting or determining the number or presence of live and/or dead cells, and the presence or amount of at least one molecule, in the sample.

12. The method of claim 11 wherein the molecule is DNA.

13. The method of claim 11 wherein the molecule is an enzyme.

14. The method of claim 11 wherein the molecule is ATP.

15. The method of claim 11 wherein the sample is subjected to conditions that lyse cells prior to detecting or determining the presence or amount of the molecule.

16. The method of claim 1 or 11 wherein one of the substrates comprises Gly-Phe-AFC.

17. The method of claim 1 or 11 wherein one of the substrates comprises (Ala-Ala-Phe)$_2$-R110.

18. The method of claim 1 or 11 wherein one of the substrates comprises Gly-Phe-AMC.

19. The method of claim 1 or 11 wherein one of the substrates comprises Ala-Ala-Phe-AMC or Ala-Ala-Phe-aminoluciferin.

* * * * *